United States Patent
Minskoff

(10) Patent No.: US 10,420,867 B2
(45) Date of Patent: Sep. 24, 2019

(54) LIQUID-GAS SEPARATOR

(71) Applicant: CONMED Corporation, Utica, NY (US)

(72) Inventor: Noah Mark Minskoff, Palo Alto, CA (US)

(73) Assignee: CONMED CORPORATION, Utica, NY (US)

( * ) Notice: Subject to any disclaimer, the term of this patent is extended or adjusted under 35 U.S.C. 154(b) by 302 days.

(21) Appl. No.: 15/296,894

(22) Filed: Oct. 18, 2016

(65) Prior Publication Data

US 2017/0224887 A1 Aug. 10, 2017

Related U.S. Application Data

(60) Provisional application No. 62/257,214, filed on Nov. 18, 2015, provisional application No. 62/243,417, filed on Oct. 19, 2015.

(51) Int. Cl.
*B01D 45/16* (2006.01)
*A61M 1/00* (2006.01)
*B01D 19/00* (2006.01)

(52) U.S. Cl.
CPC ....... *A61M 1/0056* (2013.01); *B01D 19/0036* (2013.01); *B01D 19/0042* (2013.01); *B01D 19/0094* (2013.01); *B01D 45/16* (2013.01); *A61M 2205/7509* (2013.01); *A61M 2205/7518* (2013.01); *A61M 2206/16* (2013.01)

(58) Field of Classification Search
CPC ............... B01D 45/12; B01D 45/16
USPC ...................... 55/424, 426, 459.1
See application file for complete search history.

(56) References Cited

U.S. PATENT DOCUMENTS

| | | | |
|---|---|---|---|
| 2,033,471 | A | 3/1936 | Keenan |
| 3,893,830 | A | 7/1975 | Petersen et al. |
| 4,179,273 | A | 12/1979 | Montusi |
| 4,490,331 | A | 12/1984 | Steg, Jr. |
| 4,655,754 | A | 4/1987 | Richmond et al. |
| 4,767,417 | A | 8/1988 | Boehringer et al. |
| 4,865,633 | A | 9/1989 | Stevenson |
| 5,824,212 | A | 10/1998 | Brockhoff |
| 6,073,775 | A | 6/2000 | Liu |
| 6,228,151 | B1 | 5/2001 | Conrad et al. |
| 6,228,260 | B1 | 5/2001 | Conrad et al. |
| 6,270,544 | B1 | 8/2001 | Mencher et al. |
| 6,425,931 | B1 | 7/2002 | Croggon |

(Continued)

FOREIGN PATENT DOCUMENTS

| CN | 204092667 U | 1/2015 |
|---|---|---|
| EP | 1066115 B1 | 7/2004 |

(Continued)

OTHER PUBLICATIONS

PCT/US2016/057547 International Search Report and Written Opinion dated Dec. 19, 2016.

*Primary Examiner* — Robert Hopkins
(74) *Attorney, Agent, or Firm* — Frederick J M Price; Bond, Schoeneck & King, PLLC

(57) ABSTRACT

A system for separating a flow of matter is shown and described. The system includes one or more flow separation devices, one or more surgical instruments, and one or more suction sources. In some embodiments, the flow of matter comprises biological material. In some embodiments, the flow of matter comprises surgical waste.

17 Claims, 39 Drawing Sheets

(56) References Cited

U.S. PATENT DOCUMENTS

| | | |
|---|---|---|
| 6,475,256 B2 | 11/2002 | Matsubara et al. |
| 6,533,834 B2 | 3/2003 | Conrad et al. |
| 6,827,862 B1 | 12/2004 | Brockhoff et al. |
| 7,434,694 B1 | 10/2008 | Elvin |
| 7,517,387 B2 | 4/2009 | Chevallet et al. |
| 7,615,088 B2 | 11/2009 | Benedictus et al. |
| 7,632,416 B2 | 12/2009 | Levitt |
| 7,637,991 B2 | 12/2009 | Gomiciaga-Pereda et al. |
| 7,749,292 B2 | 7/2010 | Pan et al. |
| 7,824,457 B2 | 11/2010 | Witter |
| 7,896,169 B2 | 3/2011 | Levitt et al. |
| 7,909,910 B2 | 3/2011 | Benner |
| 7,922,794 B2 | 4/2011 | Morphey |
| 7,941,895 B2 | 5/2011 | Conrad |
| 7,967,883 B2 | 6/2011 | Spain |
| 7,996,957 B2 | 8/2011 | Kah et al. |
| 8,034,140 B2 | 10/2011 | Conrad |
| 8,052,781 B2 | 11/2011 | Hunter et al. |
| 8,117,713 B2 | 2/2012 | Kasper et al. |
| 8,176,596 B2 | 5/2012 | Conrad |
| 8,201,697 B2 | 6/2012 | Levitt et al. |
| 8,250,702 B2 | 8/2012 | Conrad |
| 8,286,805 B2 | 10/2012 | Hopper |
| 8,361,179 B2 * | 1/2013 | Guerry .................. B01D 45/16 55/337 |
| 8,393,050 B2 | 3/2013 | Witter |
| 8,529,772 B2 | 9/2013 | Hopper |
| 8,640,303 B2 | 2/2014 | Conrad |
| 8,667,640 B2 | 3/2014 | Conrad |
| 8,701,896 B2 | 4/2014 | Levitt et al. |
| 8,707,511 B2 | 4/2014 | Horne |
| 8,707,512 B2 | 4/2014 | Horne |
| 8,726,461 B2 | 5/2014 | Makarov et al. |
| 8,806,708 B2 | 8/2014 | Sutton et al. |
| 8,826,492 B2 | 9/2014 | Dyson et al. |
| 8,898,857 B2 | 12/2014 | Conrad |
| 8,997,310 B2 | 4/2015 | Davidshofer et al. |
| 9,044,125 B2 | 6/2015 | Follows |
| 9,085,478 B2 | 7/2015 | England et al. |
| 9,119,511 B2 | 9/2015 | Kah, Jr. et al. |
| 9,125,535 B2 | 9/2015 | Witter et al. |
| 9,155,437 B2 | 10/2015 | Williams et al. |
| 9,204,771 B2 | 12/2015 | Gammack |
| 9,282,863 B2 | 3/2016 | Follows |
| 2003/0150198 A1 | 8/2003 | Illingworth et al. |
| 2007/0175189 A1 | 8/2007 | Gomiciaga-Pereda et al. |
| 2009/0205161 A1 | 8/2009 | Conrad |
| 2010/0313380 A1 | 12/2010 | Pan et al. |
| 2012/0284952 A1 | 11/2012 | Horne |
| 2013/0305483 A1 | 11/2013 | Dyson et al. |
| 2013/0305484 A1 | 11/2013 | Dyson et al. |
| 2013/0327726 A1 | 12/2013 | Hopper |
| 2014/0144319 A1 | 5/2014 | Paoluccio et al. |
| 2014/0352268 A1 | 12/2014 | Wilson |
| 2015/0037695 A1 | 2/2015 | Ward et al. |
| 2015/0121651 A1 | 5/2015 | Conrad |
| 2015/0143784 A1 | 5/2015 | Piedrahita et al. |
| 2015/0230679 A1 | 8/2015 | Henderson |
| 2015/0238980 A1 | 8/2015 | Chivilikhin et al. |
| 2016/0113461 A1 | 4/2016 | Rukavina et al. |
| 2016/0113462 A1 | 4/2016 | Khalil et al. |
| 2016/0114087 A1 | 4/2016 | Minskoff et al. |

FOREIGN PATENT DOCUMENTS

| | | |
|---|---|---|
| EP | 1849512 A1 | 10/2007 |
| EP | 1748848 B1 | 10/2008 |
| EP | 1669119 B1 | 12/2008 |
| EP | 1441833 B1 | 4/2009 |
| EP | 1653838 B1 | 9/2012 |
| EP | 1938733 B1 | 5/2013 |
| EP | 2626139 B1 | 12/2014 |
| EP | 2699137 B1 | 3/2015 |
| EP | 2706900 B1 | 3/2015 |
| EP | 2707143 B1 | 6/2015 |
| EP | 2707144 B1 | 6/2015 |
| EP | 2896341 A2 | 7/2015 |
| EP | 2706899 B1 | 8/2015 |
| EP | 2736623 B1 | 11/2015 |
| WO | WO-9949978 A2 | 10/1999 |
| WO | WO-03002227 A1 | 1/2003 |
| WO | WO-2005011460 A1 | 2/2005 |
| WO | WO-2005110608 A1 | 11/2005 |
| WO | WO-2007009193 A1 | 1/2007 |
| WO | WO-2008012579 A1 | 1/2008 |
| WO | WO-2008042444 A2 | 4/2008 |
| WO | WO-2008070974 A1 | 6/2008 |
| WO | WO-2008109081 A1 | 9/2008 |
| WO | WO-2008147862 A1 | 12/2008 |
| WO | WO-2009026611 A1 | 3/2009 |
| WO | WO-2009076774 A1 | 6/2009 |
| WO | WO-2010042694 A1 | 4/2010 |
| WO | WO-2012127242 A2 | 9/2012 |
| WO | WO-2012153093 A1 | 11/2012 |
| WO | WO-2012153094 A1 | 11/2012 |
| WO | WO-2012153095 A1 | 11/2012 |
| WO | WO-2012153096 A1 | 11/2012 |
| WO | WO-2012153097 A1 | 11/2012 |
| WO | WO-2012153098 A1 | 11/2012 |
| WO | WO-2012153099 A1 | 11/2012 |
| WO | WO-2013171461 A1 | 11/2013 |
| WO | WO-2015123538 A1 | 8/2015 |
| WO | WO-2016065146 A1 | 4/2016 |
| WO | WO-2016065148 A2 | 4/2016 |

* cited by examiner

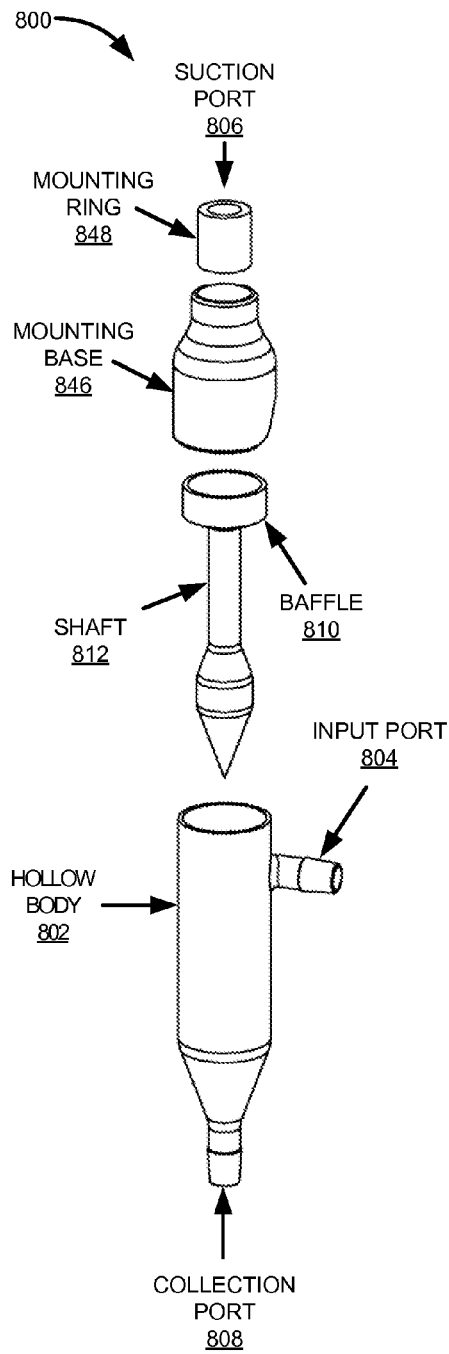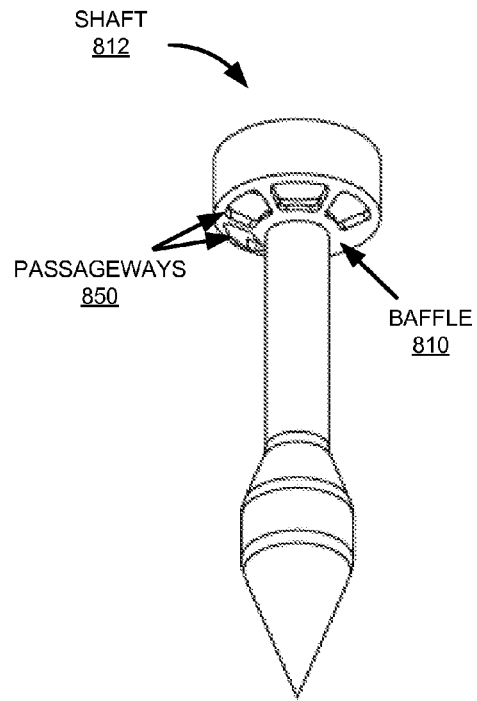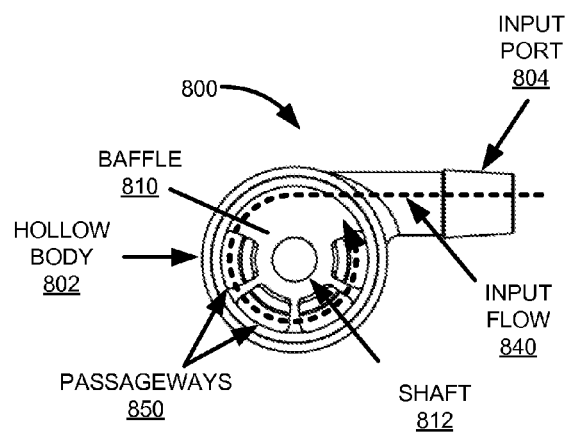
FIGURE 8A
FIGURE 8B
FIGURE 8C

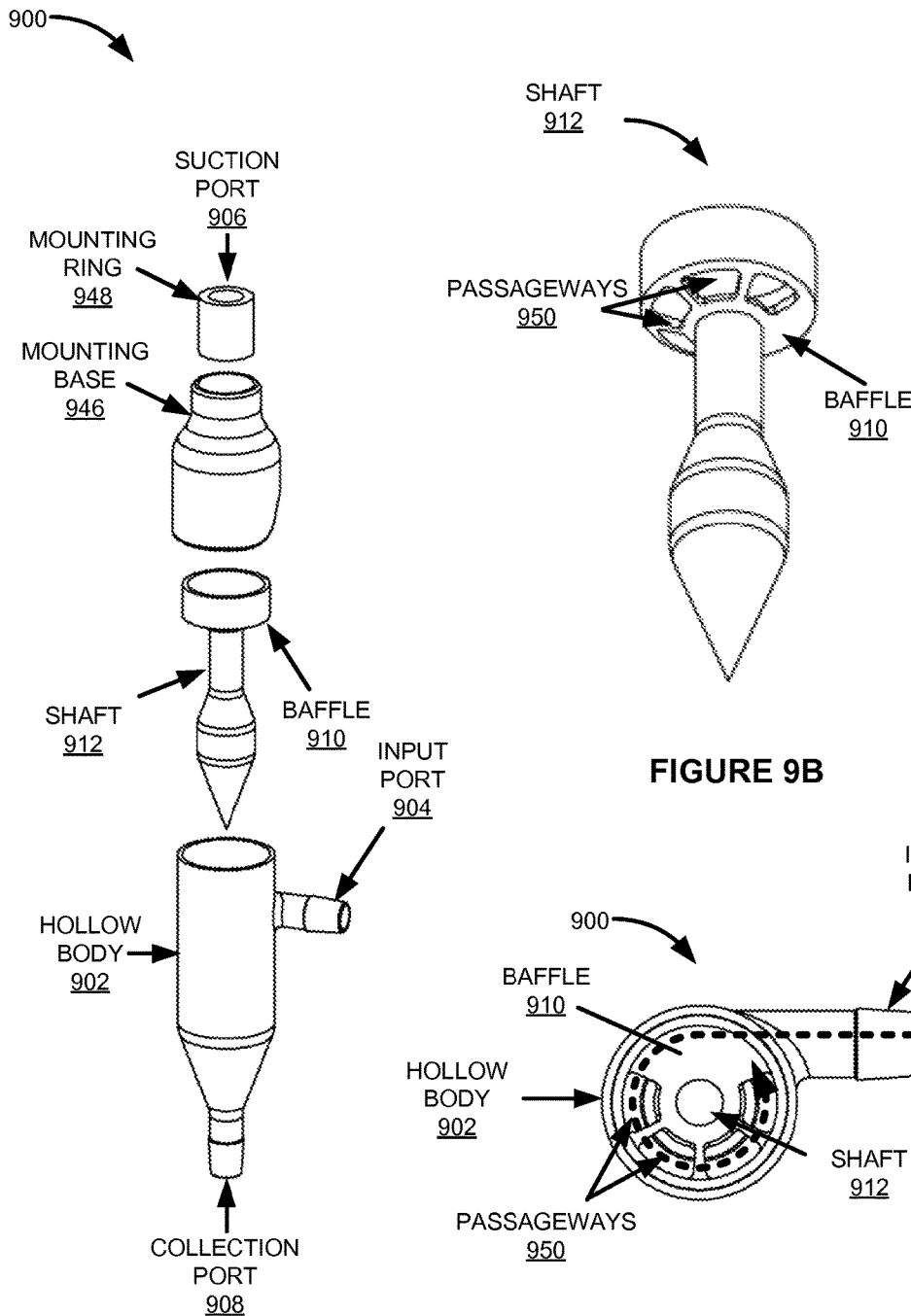

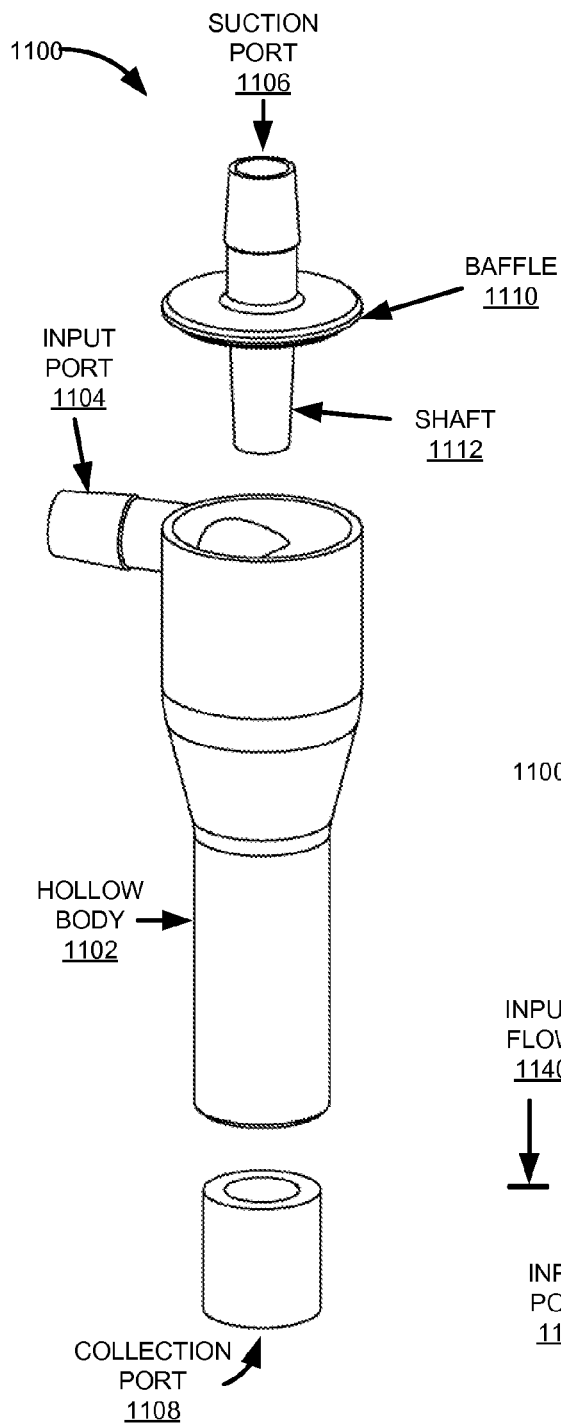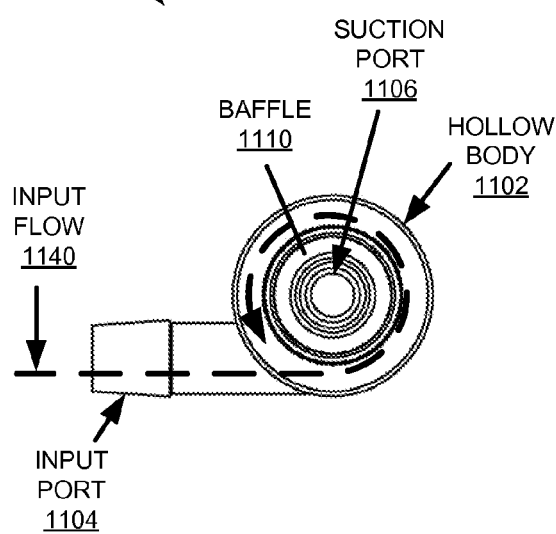
FIGURE 11A
FIGURE 11B

2000

2100
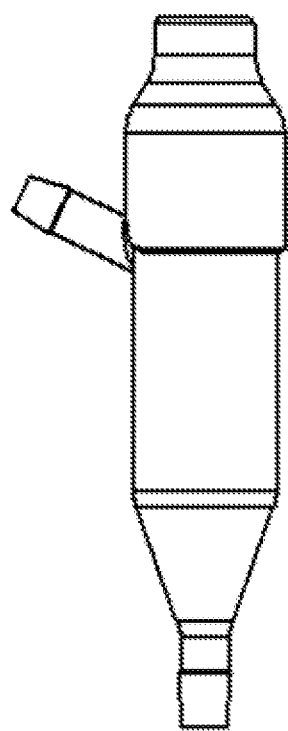
2100
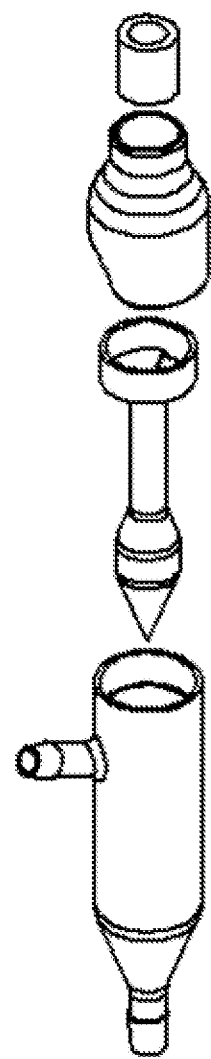
FIGURE 21A
FIGURE 21B

2200

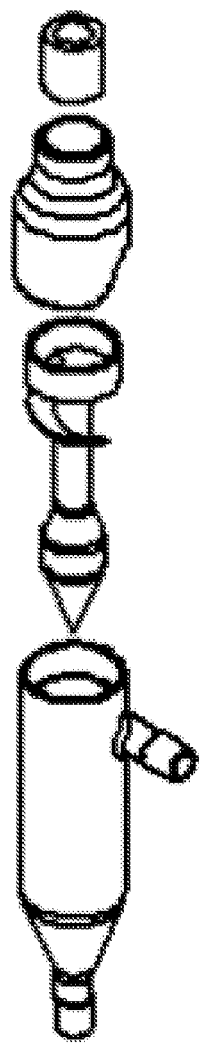
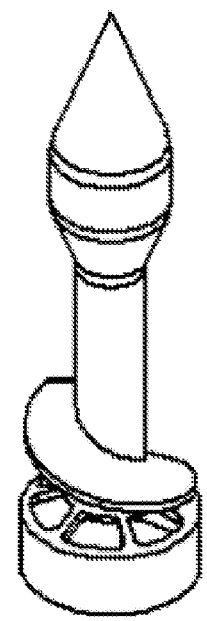
FIGURE 23B
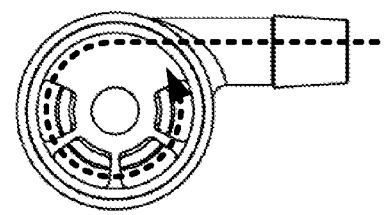
FIGURE 23A　　　　FIGURE 23C

2300

LIQUID-GAS SEPARATOR

CROSS REFERENCE

This application claims priority to U.S. provisional application 62/243,417, filed on Oct. 19, 2015; U.S. provisional application 62/257,214, filed on Nov. 18, 2015; each of which is entirely incorporated herein by reference.

BACKGROUND

Suction products suctioned from a field may comprise mixtures of solids, liquids, and gases.

SUMMARY

Described herein are devices, systems, and methods for suctioning a flow of matter from a field, such as a surgical field.

An aspect of the present disclosure provides a system for separation a flow of matter. The system comprises a flow separation device, a surgical instrument, and a suction source. The flow separation device comprises (a) a hollow body comprising a first end, a second end, and an inner volume therebetween; (b) a suction port disposed at the first end; (c) a collection port disposed at the second end; (d) an input port disposed between the first end and the second end and fluidically connected to the inner volume; (e) one or more baffles disposed within the inner volume between the first end and the second end; and (f) a shaft disposed within the inner volume. In some embodiments, the input port is configured to receive a flow of matter comprising a gas, a liquid, a solid, or combination thereof. In some embodiments, the shaft is configured to direct the flow of matter received into the hollow body. In some embodiments, at least a portion of a liquid of the flow of matter exits the hollow body from a port different than a port from which at least a portion of a gas of the flow of matter exits.

In some embodiments, the shaft directs at least a portion of the flow of matter in a cyclonic pattern along an inner surface of the hollow body. In some embodiments, the gas exits the suction port and the liquid exits the collection port. In some embodiments, the one or more baffles are configured to prevent the flow of matter from passing directly from the input port to the suction port without first traversing at least a portion of the circumference of the inner surface. In some embodiments, the one or more baffles comprise a plurality of openings configured to receive at least a portion of the flow of matter. In some embodiments, the plurality of openings is distal to the input port. In some embodiments, the one or more baffles comprise a tapered section or comprise a plurality of cylindrical sections having different diameters. In some embodiments, the second end comprises a conical shape. In some embodiments, the hollow body comprises a cylindrical shape. In some embodiments, the flow of matter comprises surgical waste. In some embodiments, the flow of matter comprises biological material.

In some embodiments, the input port is proximal to the suction port and distal from the collection port. In some embodiments, the suction port is configured to couple to the suction source. In some embodiments, the suction source is a passive suction source. In some embodiments, the collection port is configured to couple to a collection container. In some embodiments, the flow separation device is attachable or formed therein a collection container. In some embodiments, the one or more baffles aids in the separation of gas, of liquid, or a combination thereof from the flow of matter.

In some embodiments, the input port forms an angle relative to a central axis of the hollow body that is less than 90 degrees. In some embodiments, the angled input port enhances entry of the flow of matter into the input port, enhances a cyclonic pattern of flow along an inner surface of the hollow body, or a combination thereof.

In some embodiments, the flow separation device enhances a suction capacity of the surgical instrument operatively coupled to the input port. In some embodiments, the suction capacity is increased at least about 1.25 fold compared to a surgical instrument not operatively coupled to the flow separation device.

In some embodiments, the flow separation device is disposable. In some embodiments, the flow separation device further comprises one or more filters. In some embodiments, the one or more filters are disposed adjacent to the collection port. In some embodiments, a pore size of the one or more filters is less than about 1 micron. In some embodiments, the one or more filters collect one or more solids.

In some embodiments, the one or more solids are a bacterium, a bacterial fragment, a bacterial particle, a virus, a viral fragment, a viral particle, or any combination thereof. In some embodiments, the flow separation device further comprises one or more positively charged matrices, one or more negatively charged matrices, or any combination thereof. In some embodiments, the one or more positively charged matrices, one or more negatively charged matrices, or any combination thereof are operatively connected to the suction port. In some embodiments, the flow separation device is operatively coupled to one or more surgical instruments, one or more suctioning devices, one or more suction sources, one or more canisters, one or more filtration units, one or more charged matrices, or any combination thereof.

Another aspect of the present disclosure provides a flow separation device. In some embodiments, the flow separation device comprises: (a) a separator body having a cylindrical cavity having a cylindrical wall and first cylindrical cavity end and a second cylindrical cavity end, configured to operate with the first cylindrical cavity end up; (b) a conical cavity having a narrow end and a wide end, the wide end mated to the second cylindrical cavity end; (c) an input port disposed in the cylindrical cavity wall, configured to receive a flow of matter; (d) an suction port mated to the first cylindrical cavity end and configured to couple to a vacuum source; (e) an collection port mated to the narrow end of the conical cavity and configured to couple to a waste deposit; (f) a baffle disposed between the input port and the suction port, configured to prevent the flow of matter from passing directly from the input port to the suction port without first traversing at least a portion of a circumference of an interior of the cylindrical wall; and (g) a cylindrical shaft disposed within a center of the cylindrical cavity and configured to direct the flow of matter within the cylindrical cavity.

In some embodiments, the input port is located off-axis of an axis defined by the longitudinal center of the separator body. In some embodiments, the input port is located closer to the first cylindrical end than the second cylindrical end. In some embodiments, the suction source comprises a vacuum pump.

In some embodiments, the suction source comprises a positive pressure operated suction generator that utilizes a Coanda effect. In some embodiments, the suction source comprises a positive pressure operated suction generator that utilizes a Venturi effect.

In some embodiments, the baffle comprises a plurality of openings to allow passage of the flow of matter, comprising separated portions thereof, out of the suction port. In some embodiments, the baffle comprises a solid surface located proximal to the input port and distal to the plurality of openings, configured to prevent the flow of matter, comprising separated portions thereof, from passing directly from the input port to the suction port without first traversing at least a portion of a circumference of the cylindrical cavity wall.

In some embodiments, the baffle is integral to the cylindrical shaft. In some embodiments, the cylindrical shaft comprises a plurality of conic sections each comprising a wide end and a narrow end of varying diameters and a plurality of cylindrical sections of varying diameter configured to direct the flow of matter within the cylindrical cavity. In some embodiments, the separator is further configured to allow passage of the flow of matter, unseparated, from the input port to the suction port when the flow of matter is no longer able to be expelled out of the collection port.

Another aspect of the present disclosure provides a method of operating a separator. In some embodiments, the method comprises: (a) providing a separator comprising: a separator body comprising: (i) a cylindrical cavity having a cylindrical wall and first cylindrical cavity end and a second cylindrical cavity end, configured to operate with the first cylindrical cavity end up; (ii) a conical cavity having a narrow end and a wide end, the wide end mated to the second cylindrical cavity end; (iii) an input port disposed in the cylindrical cavity wall configured to receive a flow of matter; (iv) an suction port mated to the first cylindrical cavity end and configured to couple to a vacuum source; (v) a collection port mated to the narrow end of the conical cavity and configured to couple to a waste deposit; (vi) a baffle disposed between the input port and the suction port, configured to prevent the flow of matter from passing directly from the input port to the suction port without first traversing at least a portion of a circumference of an interior of the cylindrical wall; and (vii) a cylindrical shaft disposed within a center of the cylindrical cavity and configured to direct the flow of matter within the cylindrical cavity, (b) attaching the suction port to the suction source; (c) mating the collection port to a waste deposit; (d) activating the suction source thereby creating the flow of matter into the input port; (e) expelling portions of the flow of matter out of the collection port; and (f) pulling portions of the flow of matter out of the suction port.

In some embodiments, the method further comprises locating the input port off-axis of an axis defined by a longitudinal center of the separator body. In some embodiments, the method further comprises locating the input port closer to the first cylindrical end than the second cylindrical end. In some embodiments, the method further comprises providing the suction source using a vacuum pump.

In some embodiments, the method further comprises providing the suction source using a positive pressure operated suction generator that utilizes a Coanda effect. In some embodiments, the method further comprises providing the suction source using a positive pressure operated suction generator that utilizes a Venturi effect.

In some embodiments, the method further comprises providing the baffle with a plurality of openings allowing passage of the flow of matter, comprising separated portions thereof, out of the suction port. In some embodiments, the method further comprises providing the baffle a solid surface located proximal to the input port and distal to the opening, thereby preventing the flow of matter, comprising separated portions thereof, from passing directly from the input port to the suction port without first traversing at least a portion of a circumference of the cylindrical cavity wall.

In some embodiments, the method further comprises integrating the baffle to the cylindrical shaft. In some embodiments, the method further comprises providing the cylindrical shaft a plurality of conic sections each comprising a wide end and a narrow end of varying diameters and a plurality of cylindrical sections of varying diameter thereby directing the flow of matter along the cylindrical cavity wall. In some embodiments, the method further comprises allowing passage of the flow of matter, unseparated, from the input port to the suction port when the flow of matter is no longer expelling out of the collection port. In some embodiments, the method further comprises providing the suction source using a vacuum pump. In some embodiments, the method further comprises providing the suction source using a positive pressure operated suction device that utilizes a Coanda effect. In some embodiments, the method further comprises coupling the separator to a canister.

Another aspect of the present disclosure provides a system of flow separators. In some embodiments, the system of flow separators comprises: (a) one or more separators, each comprising: a separator body comprising: (i) a cylindrical cavity having a cylindrical wall and first cylindrical cavity end and a second cylindrical cavity end, configured to operate with the first cylindrical cavity end up; (ii) a conical cavity having a narrow end and a wide end, the wide end mated to the second cylindrical cavity end; (iii) an input port disposed in the cylindrical cavity wall, configured to receive a flow of matter; an suction port mated to the first cylindrical cavity end and configured to couple to a vacuum source; (iv) an collection port mated to the narrow end of the conical cavity and configured to couple to a waste deposit; (v) a baffle disposed between the input port and the suction port, configured to prevent the flow of matter from passing directly from the input port to the suction port without first traversing at least a portion of a circumference of the interior of the cylindrical wall; and (vi) a cylindrical shaft disposed within the center of the cylindrical cavity and configured to direct the flow within the cylindrical cavity; and (b) one or more canisters configured to couple to an associated separator.

In some embodiments, the suction port of one separator is coupled to the input port of another separator. In some embodiments, the one or more separators are configured to discontinue filling a first canister when the first canister has reached a pre-determined volume and allow the flow of matter, unseparated, to pass through the input port and out of the output port of a first separator to the input port of a second separator coupled to a canister that is not filled to a pre-determined capacity.

Another aspect of the present disclosure provides a method of operating a separator system. In some embodiments, the system comprises: (a) providing one or more separators, each comprising: a separator body comprising: (i) a cylindrical cavity having a cylindrical wall and first cylindrical cavity end and a second cylindrical cavity end, configured to operate with the first cylindrical cavity end up; (ii) a conical cavity having a narrow end and a wide end, the wide end mated to the second cylindrical cavity end; (iii) an input port disposed in the cylindrical cavity wall, configured to receive a flow of matter; (iv) an suction port mated to the first cylindrical cavity end and configured to couple to a vacuum source; (v) an collection port mated to the narrow end of the conical cavity and configured to couple to a waste deposit; (vi) a baffle disposed between the input port and the suction port, configured to prevent the flow of matter from passing directly from the input port to the suction port without first traversing at least a portion of the circumference of the interior of the cylindrical wall; and (vii) a cylindrical shaft disposed within the center of the cylindrical cavity and configured to direct the flow of matter within the cylindrical cavity; (b) coupling the suction port of one separator to the input port of another separator, forming a series of separators; (c) attaching the suction port of a last separator in the series of separators to the suction source; (d) activating the suction source thereby creating a flow of matter through the series of separators; (e) receiving the flow of matter into the input port of a first separator in the series of separators; (f) pulling gas out of the suction port of the first separator while an associated canister is filled below a pre-determined capacity; expelling portions of the flow of matter out of the collection port of the first separator until an associated canister is filled to a pre-determined limit; (g) passing the flow of matter from the input port out of the suction port of the first separator to an input port of a second separator in the series of separators coupled to a canister that is not filled to a predetermined limit; receiving the flow of matter into the input port of the second separator; (h) pulling gas out of the suction port of the second separator while an associated canister is filled below a pre-determined capacity; and (i) expelling portions of the flow of matter out of the collection port of the second separator until an associated canister is filled to a pre-determined limit.

In some embodiments, the method further comprises providing the suction source using a vacuum pump. In some embodiments, the method further comprises providing the suction source using a positive pressure operated suction generator that utilizes a Coanda effect.

Another aspect of the present disclosure provides a liquid-gas flow separator. In some embodiments, the separator comprises: (a) a cylindrical cavity comprising a cylindrical cavity wall, a first cylindrical cavity end, and a second cylindrical cavity end, the separator configured to operate with the first cylindrical cavity end being up; (b) a suction port to be coupled to a suction source, the suction port being in the first cylindrical cavity end; (c) a conical cavity, the conical cavity comprising a wide end and a narrow end, the wide end being mated to the second cylindrical cavity end; (d) a collection port at the narrow end of the conical cavity; (e) an input port to receive a flow of matter comprising a mixture of liquid and gas, the input port being in the cylindrical cavity wall, the flow of matter induced into the separator by the suction source, the input port configured to direct liquids in the flow the matter to cling to the cylindrical cavity wall; (f) a baffle disposed between the input port and the suction port, the baffle configured to prevent liquids in the flow of matter from being pulled directly from the input port to the suction port without traversing at least a first portion of a circumference of the cylindrical cavity wall, the baffle configured to allow gasses in the flow of matter to separate from the liquids in the flow of matter and be pulled out of the separator via the suction port; and a cylindrical central member disposed within the cylindrical cavity, the central member disposed to form an annular cavity between the cylindrical central member and the cylindrical cavity wall, the liquids in the flow of matter pass through the annular cavity before dropping out the collection port.

In some embodiments, the flow of matter further comprises solids, the solids in the flow of matter pass through the annular cavity before dropping out the collection port. In some embodiments, the baffle comprises a plurality of openings to allow the gasses in the flow of matter to be pulled out of the separator via the suction port. In some embodiments, the baffle comprises a solid portion that prevents liquids in the flow of matter from being pulled directly from the input port to the suction port, the solid portion corresponding to at least the first portion of the circumference.

In some embodiments, the central member comprises a tapered section disposed in the conical cavity. In some embodiments, the central member comprises a plurality of cylindrical sections comprising different diameters.

In some embodiments, a plurality of cylindrical sections includes a first section that defines a first portion of the annular cavity and a second section that defines a second portion of the annular cavity. In some embodiments, the first portion is disposed between the baffle and the second portion, the second portion is disposed between the first portion and the conical cavity. In some embodiments, the central member further comprises a tapered section disposed in the conical cavity thereby forming a hollow cone shaped cavity, the hollow cone shaped cavity disposed between the second portion and the second port.

Another aspect of the present disclosure provides a method of operating a liquid-gas flow separator. In some embodiments, the method comprises: (a) providing a cylindrical cavity having a cylindrical cavity wall, a first cylindrical cavity end, and a second cylindrical cavity end, and operating the separator with the first cylindrical cavity end being up; (b) coupling a suction port to a suction source, the suction port being in the first cylindrical cavity end; (c) providing a conical cavity, the conical cavity having a wide end and a narrow end, and mating the wide end to the second cylindrical cavity end; (d) providing a collection port at the narrow end of the conical cavity; (e) receiving a flow comprising a mixture of liquid and gas at a input port, the input port being in the cylindrical cavity wall, and inducing the flow into the separator by the suction source, directing liquids in the flow to cling to the cylindrical cavity wall by configuring the input port; (f) providing a baffle disposed between the input port and the suction port, thereby preventing liquids in the flow from being pulled directly from the input port to the suction port without traversing at least a first portion of a circumference of the cylindrical cavity wall, and allowing gasses in the flow to separate from the liquids in the flow and pulling the gasses out of the separator via the suction port; and (g) providing a cylindrical central member disposed within the cylindrical cavity, disposing the central member to form an annular cavity between the central member and the cylindrical cavity wall, and passing the liquids in the flow through the annular cavity before dropping out the collection port.

In some embodiments, the method further comprises providing a flow further comprising solids and passing the solids in the flow through the annular cavity before dropping out the collection port. In some embodiments, the method further comprises providing the baffle comprising a plurality of openings to allow the gasses in the flow to be pulled out of the separator via the suction port. In some embodiments, the method further comprises preventing liquids in the flow from being pulled directly from the input port to the suction port by providing the baffle comprising a solid portion, the solid portion corresponding to at least the first portion of the circumference.

In some embodiments, the method further comprises providing the central member comprising a tapered section disposed in the conical cavity. In some embodiments, the method further comprises providing the central member comprising a plurality of cylindrical sections comprising different diameters. In some embodiments, the method further comprises providing a plurality of cylindrical sections comprising a first section defining a first portion of the annular cavity and a second section defining a second portion of the annular cavity.

In some embodiments, the method further comprises disposing the first portion between the baffle and the second portion and disposing the second portion between the first portion and the conical cavity. In some embodiments, the method further comprises providing the central member a tapered section disposed in the conical cavity thereby forming a hollow cone shaped cavity and disposing the hollow cone shaped cavity between the second portion and the collection port.

Another aspect of the present disclosure provides a flow separator. In some embodiments, the flow separator comprises: (a) a cylindrical cavity comprising a cylindrical wall comprising a first end and a second end, the first end disposed in an upward position, and means for directing a flow of matter along a circumference of the cylindrical cavity wall; (b) an input port mated to the cylindrical cavity wall, and means for receiving the flow of matter and directing the flow of matter into the cylindrical cavity; (c) an suction port mated to the first end of the cylindrical cavity, and means for coupling the separator to a suction source; (d) the suction port comprising means for expelling at least gasses out of the separator; (e) a conical cavity comprising a wide end and a narrow end and a conical cavity wall, the wide end mated to the second end of the cylindrical cavity, and a means for directing the flow of matter to create a flow within the cylindrical cavity whereby gasses are directed out of the suction port and at least liquids are directed out of narrow end of the conical cavity; (f) an collection port mated to the narrow end of the conical cavity, and a means for expelling at least liquids for collection; (g) a baffle disposed between the input port and the first end of the cylindrical cavity, and means for preventing liquids and/or solids from passing from the input port to the suction port without first traversing at least a portion of the circumference of the cylindrical cavity wall; and (h) a cylindrical central member disposed concentrically within the cylindrical cavity forming an annular cavity between the cylindrical central member and the cylindrical cavity wall to allow passage of at least liquids, and means for expelling at least liquids out of the collection port for collection.

In some embodiments, the flow of matter comprises one or more of liquids, solids and gasses, and means for the liquids and/or solids to pass through the annular cavity and out of the collection port.

In some embodiments, the baffle comprises a plurality of openings, and means for allowing matter to pass through the baffle and out the suction port after traversing at least a portion of the circumference of the cylindrical cavity wall. In some embodiments, the baffle comprises a solid portion disposed proximally to the input port, and means for preventing liquids and/or solids in the flow of matter from being pulled directly from the input port to the suction port before traversing at least a portion of a circumference of the cylindrical cavity wall.

In some embodiments, the central member comprises a tapered section disposed in the conical cavity, and means for directing the flow of matter within the separator. In some embodiments, the central member comprises a plurality of cylindrical sections comprising different diameters, and means for directing the flow of matter within the separator.

In some embodiments, a plurality of cylindrical sections include a first section that defines a first portion of the annular cavity and a second section that defines a second portion of the annular cavity, and means for directing the flow of matter within the separator. In some embodiments, the first portion is disposed between the baffle and the second portion, the second portion is disposed between the first portion and the conical cavity, and means for directing the flow of matter within the separator. In some embodiments, the central member further comprises a tapered section disposed in the conical cavity thereby forming a hollow cone shaped cavity, the hollow cone shaped cavity disposed between the second portion and the collection port, and means for directing the flow of matter through the hollow cone shaped cavity.

Another aspect of the present disclosure provides a system of liquid-gas separators. In some embodiments, the system comprises: (a) one or more separators comprising: (i) a cylindrical cavity comprising a cylindrical wall comprising a first end and a second end, the first end disposed in an upward position, and means for directing a flow of matter along the circumference of the cylindrical cavity wall; (ii) an input port mated to the cylindrical cavity wall, and means for receiving the flow of matter and directing the flow of matter into the cylindrical cavity; (iii) an suction port mated to the first end of the cylindrical cavity, and means for coupling the separator to a suction source; (iv) the suction port comprising means for expelling at least gasses out of the separator; (v) a conical cavity comprising a wide end and a narrow end and a conical cavity wall, the wide end mated to the second end of the cylindrical cavity, and a means for directing the flow of matter to create a flow within the cylindrical cavity whereby gasses are directed out of the suction port and at least liquids are directed out of narrow end of the conical cavity; (vi) an collection port mated to the narrow end of the conical cavity, and a means for expelling at least liquids for collection; (vii) a baffle disposed between the input port and the first end of the cylindrical cavity, and means for preventing liquids and/or solids from passing from the input port to the suction port without first traversing at least a portion of the circumference of the cylindrical cavity wall; and (viii) a cylindrical central member disposed concentrically within the cylindrical cavity forming an annular cavity between the cylindrical central member and the cylindrical cavity wall to allow passage of at least liquids, and means for expelling at least liquids out of the collection port for collection; (b) one or more canisters each mated to a corresponding separator, and a means for coupling to the separator and collecting at least a portion of the flow of matter from the collection port; and (c) a suction source, and a means for providing suction to the suction port.

In some embodiments, the flow of matter comprises one or more of liquids, solids and gasses, and means for the liquids and/or solids to pass through the annular cavity and out of the collection port. In some embodiments, the baffle comprises a plurality of openings, and means for allowing matter to pass through the baffle and out the suction port after traversing at least a portion of the circumference of the cylindrical cavity wall. In some embodiments, the baffle comprises a solid portion disposed proximally to the input port, and means for preventing liquids and/or solids in the flow from being pulled directly from the input port to the suction port before traversing at least a portion of the circumference of the cylindrical cavity wall.

In some embodiments, the central member comprises a tapered section disposed in the conical cavity, and means for directing the flow of matter within the separator. In some embodiments, the central member comprises a plurality of cylindrical sections comprising different diameters, and means for directing the flow of matter within the separator.

In some embodiments, a plurality of cylindrical sections include a first section that defines a first portion of the annular cavity and a second section that defines a second portion of the annular cavity, and means for directing the flow of matter within the separator. In some embodiments, the first portion is disposed between the baffle and the second portion, the second portion is disposed between the first portion and the conical cavity, and means for directing the flow of matter within the separator. In some embodiments, the central member further comprises a tapered section disposed in the conical cavity thereby forming a hollow cone shaped cavity, the hollow cone shaped cavity disposed between the second portion and the second port, and means for directing the flow of matter through the hollow cone shaped cavity. In some embodiments, the suction port of a first separator is coupled to the input port of a second separator, and means for providing suction to the first separator through the second separator.

In some embodiments, the system further comprises a means for allowing the flow of matter to pass from the input port to the suction port of the first separator, when the canister corresponding to the first separator is filled to a capacity, to the second separator and collecting at least a portion of the flow of matter in the canister corresponding to the second separator. In some embodiments, the suction source comprises a vacuum pump, and means for providing vacuum to the suction port.

In some embodiments, the suction source comprises a means for generating suction based on a Coanda effect. In some embodiments, the suction source comprises a means for generating suction based on a Venturi effect.

Another aspect of the present disclosure provides a separator for use in a medical environment. In some embodiments, the separator comprise: (a) a cylindrical cavity having a cylindrical cavity wall, a first cylindrical cavity end, and a second cylindrical cavity end, the separator configured to operate with the first cylindrical cavity end being up; (b) an suction port to be coupled to an operating room suction source, the suction port being in the first cylindrical cavity end; (c) a conical cavity, the conical cavity having a wide end and a narrow end, the wide end being mated to the second cylindrical cavity end; (d) an collection port at the narrow end of the conical cavity; (e) an input port to receive a flow comprising a mixture of liquid and gas, the input port being in the cylindrical cavity wall, the flow to be induced into the separator by the suction source, the input port configured to direct liquids in the flow to cling to the cylindrical cavity wall; (f) a baffle disposed between the input port and the suction port, the baffle to prevent liquids in the flow from being pulled directly from the input port to the suction port without traversing at least a first portion of a circumference of the cylindrical cavity wall, the baffle to allow gasses in the flow to separate from the liquids in the flow and be pulled out of the separator via the suction port; and (g) a cylindrical central member disposed within the cylindrical cavity, the central member disposed to form an annular cavity between the central member and the cylindrical cavity wall, the liquids in the flow to pass through the annular cavity before dropping out the collection port.

In some embodiments, the flow further comprises solids, the solids in the flow to pass through the annular cavity before dropping out the second port. In some embodiments, the liquids include intracellular fluids and extracellular fluids. In some embodiments, the liquids include blood. In some embodiments, the gas comprises smoke generated from electrosurgical tools comprising a bovie, harmonic scalpel, electrosurgical pencil and laser.

In some embodiments, the baffle comprises a plurality of openings to allow the gasses in the flow be pulled out of the separator via the first port. In some embodiments, the baffle comprises a solid portion that prevents liquids in the flow from being pulled directly from the collection port to the first port, the solid portion corresponding to at least the first portion of the circumference.

In some embodiments, the central member comprises a tapered section disposed in the conical cavity. In some embodiments, the central member comprises a plurality of cylindrical sections comprising different diameters.

In some embodiments, a plurality of cylindrical sections includes a first section that defines a first portion of the annular cavity and a second section that defines a second portion of the annular cavity. In some embodiments, the first portion is disposed between the baffle and the second portion, the second portion is disposed between the first portion and the conical cavity. In some embodiments, the central member further comprises a tapered section disposed in the conical cavity thereby forming a hollow cone shaped cavity, the hollow cone shaped cavity disposed between the second portion and the second port.

Another aspect of the present disclosure provides a method of operating a separator in a medical environment. In some embodiments, the method comprises: (a) providing one or more fluid separators, wherein a fluid separator comprises: (i) a cylindrical cavity comprising a cylindrical cavity wall, a first cylindrical cavity end, and a second cylindrical cavity end, the fluid separator configured to operate with the first cylindrical cavity end being up; (ii) an suction port operatively coupled to a suction source, the suction port being in the first cylindrical cavity end; (iii) a conical cavity, the conical cavity comprising a wide end and a narrow end, the wide end mated to the second cylindrical cavity end; (iv) an collection port at the narrow end of the conical cavity; (v) an input port to receive a flow comprising a mixture of liquid and gas, the input port being in the cylindrical cavity wall, the flow to be induced into the separator by the suction source, the input port configured to direct liquids in the flow to cling to the cylindrical cavity wall; (vi) a baffle disposed between the input port and the suction port, the baffle to prevent liquids in the flow from being pulled directly from the input port to the suction port without traversing at least a first portion of a circumference of the cylindrical cavity wall, the baffle to allow gasses in the flow to separate from the liquids in the flow and be pulled out of the separator via the suction port; and (vii) a cylindrical central member disposed within the cylindrical cavity, the central member disposed to form an annular cavity between the central member and the cylindrical cavity wall, the liquids in the flow to pass through the annular cavity before dropping out the collection port; (b) attaching the one or more separators each to an associated waste deposit; (c) attaching the suction port to a suction source; (d) activating the suction source, thereby creating flow through the one or more separators; (e) directing the flow using the cylindrical cavity and cylindrical central member to separate element comprising the flow; (f) ejecting liquids and/or solids from the collection port that have been separated from the flow; and (g) pulling the gas out of the suction port using the suction source. In some embodiments, the method further comprises providing a canister as the waste deposit.

In some embodiments, attaching the suction port to a suction source comprises attaching the suction port of a first separator to the input port of a second separator that is attached to a suction source. In some embodiments, the method further comprises attaching the input port of a separator to a suction device. In some embodiments, the method further comprises attaching the suction device to a surgical instrument.

In some embodiments, the method further comprises operating the one or more separators in series by coupling the suction port of one separator to the input port of another separator, coupling the suction port of the last separator in the series of separators to the suction source and receiving the flow at the input of the first separator in the series of separators. In some embodiments, the method further comprises receiving matter into the input port of a first separator in a series of separators via the suction source applied to the suction port of a last separator in the series of separators, pulling gas out of the suction port of another separator in the series of separators while an associated canister is filled below a pre-determined capacity expelling portions of the flow out of the collection port of another separator in the series of separators until an associated canister is filled to a pre-determined limit. In some embodiments, the method further comprises passing the flow, unseparated, from the input port out of the suction port of the first separator in the series of separators when the flow is no longer ejecting from the collection port of the first separator to the input port of another separator ejecting the flow, or portions thereof, out of the collection port.

Another aspect of the present disclosure provides a system for separating a flow of matter. In some embodiments, the system comprises: (a) a flow separation device comprising: (i) a hollow body comprising a first end, a second end, and an inner volume therebetween; (ii) a suction port disposed at the first end; (iii) a collection port disposed at the second end; (iv) an input port disposed between the first end and the second end and in fluid communication with the inner volume; (v) one or more baffles disposed within the inner volume between the first end and the second end; and (vi) a shaft disposed within the inner volume, (b) a surgical instrument; and (c) a suction source; wherein the input port is configured to receive the flow of matter from the surgical instrument, the flow of matter comprising a gas, a liquid, a solid, or any combination thereof, wherein the shaft is configured to direct the flow of matter received into the hollow body, and wherein at least a portion of a liquid of the flow of matter exits the hollow body from a port different than a port from which at least a portion of a gas of the flow of matter exits.

In some embodiments, the shaft directs at least a portion of the flow of matter in a cyclonic pattern along an inner surface of the hollow body. In some embodiments, the gas exits the suction port and the liquid exits the collection port.

In some embodiments, the one or more baffles are configured to prevent the flow of matter from passing directly from the input port to the suction port without first traversing at least a portion of a circumference of an inner surface of the hollow body. In some embodiments, the one or more baffles comprise a plurality of openings configured to receive at least a portion of the flow of matter. In some embodiments, the plurality of openings is distal to the input port. In some embodiments, the one or more baffles comprise a tapered section or comprise a plurality of cylindrical sections comprising different diameters.

In some embodiments, the second end comprises a conical shape. In some embodiments, the hollow body comprises a cylindrical shape. In some embodiments, the flow of matter comprises surgical waste. In some embodiments, the flow of matter comprises biological material.

In some embodiments, the input port is proximal to the suction port and distal from the collection port. In some embodiments, the suction port is configured to couple to the suction source. In some embodiments, the suction source is a passive suction source.

In some embodiments, the collection port is configured to couple to a collection container. In some embodiments, the flow separation device is attachable or formed therein a collection container. In some embodiments, the one or more baffles aids in the separation of gas, of liquid, or a combination thereof from the flow of matter.

In some embodiments, the input port forms an angle relative to a central axis of the hollow body that is less than 90 degrees forming an angled input port. In some embodiments, the angled input port enhances entry of the flow of matter into the angled input port, enhances a cyclonic pattern of flow along an inner surface of the hollow body, or a combination thereof.

In some embodiments, the flow separation device enhances a suction capacity of the surgical instrument operatively coupled to the input port. In some embodiments, the suction capacity is increased at least about 1.25 fold compared to a surgical instrument not operatively coupled to a flow separation device. In some embodiments, the flow separation device is disposable.

In some embodiments, the system further comprises one or more filters. In some embodiments, the one or more filters are disposed adjacent to the collection port. In some embodiments, a pore size of the one or more filters is less than about 1 micron. In some embodiments, the one or more filters collect one or more solids. In some embodiments, the one or more solids are a bacterium, a bacterial fragment, a bacterial particle, a virus, a viral fragment, a viral particle, or any combination thereof In some embodiments, the system further comprises one or more positively charged matrices, one or more negatively charged matrices, or any combination thereof In some embodiments, the one or more positively charged matrices, the one or more negatively charged matrices, or any combination thereof are operatively connected to the suction port. In some embodiments, the flow separation device is operatively coupled to one or more surgical instruments, one or more suctioning devices, one or more suction sources, one or more canisters, one or more filtration units, one or more charged matrices, or any combination thereof.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the subject matter described herein are set forth with particularity in the appended claims. A better understanding of the features and advantages of the present subject matter will be obtained by reference to the following detailed description that sets forth illustrative embodiments, in which the principles of the subject matter described herein are utilized, and the accompanying drawings of which:

FIG. 8A is an exploded-view diagram illustrating a separator.

FIG. 8B is a diagram illustrating a shaft (such as a vortex element).

FIG. 8C is a top-view diagram illustrating the operation of a separator.

FIG. 9A is an exploded-view diagram illustrating a separator.

FIG. 9B is a diagram illustrating a shaft (such as a vortex element).

FIG. 9C is a top-view diagram illustrating the operation of a separator.

FIG. 11A is an exploded-view diagram illustrating a separator.

FIG. 11B is a top-view diagram illustrating the operation of a separator.

FIG. 21A-B are diagrams illustrating a flow separation device with an angled input port.

FIG. 23A-C are diagrams illustrating a helical baffle.

FIG. 23C is a diagram illustrating a flow path into the input port of the flow separation device.

DETAILED DESCRIPTION

While various embodiments have been shown and described herein, it will be obvious to those skilled in the art that such embodiments are provided by way of example only. Numerous variations, changes, and substitutions may occur to those skilled in the art without departing from the subject matter described herein. It should be understood that various alternatives to the embodiments of the subject matter described herein is employed.

Figure 1:
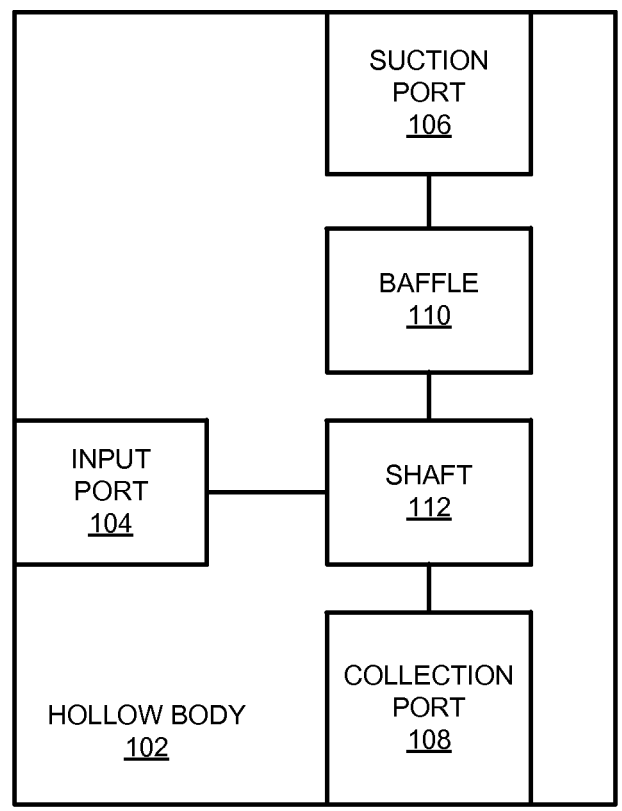
FIG. 1 is a block diagram illustrating a separator.

FIG. 1 is a block diagram illustrating separator 100. In operation, separator 100 is configured to separate liquids, solids and gasses in a flow of matter. Separator 100 ejects liquids and/or solids separated from the flow of matter out collection port 108 while suctioning at least gasses separated from the flow of matter out suction port 106. Separator 100 is operated by suction received from a suction source. It should be understood that the terms "suction" and "vacuum" as used herein refer to a pressure below the surrounding ambient air pressure.

In some embodiments, separator 100 comprises hollow body 102, input port 104, suction port 106, collection port 108, baffle 110, and shaft 112.

In some embodiments, hollow body 102 comprises a cylindrical wall defining a cylindrical cavity. Other hollow body 102 shapes are suitable for use with the separator 100 including conical shapes and ovoid cylindrical shapes. The hollow body 102 wall may include a first cavity end and a second cavity end. The cavity of hollow body 102 may have a wide end and a narrow end. Hollow body 102 is constructed of a single solid wall that is formed into the hollow body 102 shape, or alternatively, a first wide end of hollow body 102 is mated to a second narrow end of hollow body 102 to form a single hollow body 102 having a narrow section and wide section. In some embodiments, hollow body 102 is configured to operate in an orientation with the first cavity end up. Hollow body 102 is configured to be oriented in operation to allow gravity to pull at least liquid and solids separated from a flow of matter out collection port 108, while gasses separated from the flow of matter are pulled by suction out of suction port 106.

Input port 104 is configured to receive a flow of matter. In some embodiments, input port 104 is integral to hollow body 102. Input port 104 is disposed in the cylindrical cavity wall. Input port 104 is located off-axis from an axis defined by the longitudinal center of the cylindrical cavity.

Input port 104 is configured and positioned to direct a flow of matter received into the hollow body 102 along the internal cavity wall of the hollow body 102. Because, in some embodiments, the hollow body 102 comprises a cylindrical, spherical, or ovoid cylindrical shape, the flow generated within the cavity of the hollow body 102 comprises and essentially cyclonic flow pattern.

By directing the flow of matter along the internal cavity wall of the hollow body 102, forming a cyclonic flow pattern, liquids, solids, and gasses will tend to cling to the wall of the internal cavity wall of hollow body 102 due to the effects of centripetal forces.

A flow of matter is induced into separator 100 by suction received from suction port 106 by a suction or vacuum source. In some embodiments, suction port 106 further comprises a check valve mechanism (not shown in FIG. 1) to, for example, prevent the flow of solids or liquids through suction port 106.

Suction port 106 is configured to couple to a suction source. In certain embodiments, the suction source may include, for example, a vacuum pump, aspirator, and/or a positive pressure operated suction source—such as suction sources that take advantage of Venturi or Coanda effect. Suction from a suction source is transferred from suction port 106 to input port 104. Suction port 106 is disposed near the first cavity end of the hollow body 102. Suction port 106 provides suction received from a suction source for operating separator 100 and may further comprise a check valve. In some embodiments, suction port 106 includes fittings configured to attach tubing. For example, barbed or quick-disconnect type fittings are used to couple tubing to suction port 106. The tubing is, for example, used to couple suction port 106 to a suction source or to an input port 104 of another separator.

Collection port 108 is configured to expel at least liquids and/or solids. Collection port 108 is disposed at the narrow end of the conical cavity of hollow body 102. In some embodiments, collection port 108 is configured to couple to a canister. A canister is used to collect and measure matter received from separator 100. A canister may also be used for the safe collection, transportation and disposal of waste received from separator 100. In some embodiments, collection port 108 is coupled to tubing or piping to direct matter to a waste drain. In some embodiments, collection port 108 may include a mounting ring configured to form a seal between collection port 108 to tubing or a canister.

Baffle 110 is disposed between input port 104 and suction port 106. Baffle 110 is configured to facilitate a cyclonic flow of matter within the hollow cavity 100 by preventing liquids and/or solids in the flow from being pulled directly from input port 104 to suction port 106 without traversing at least a first portion of a circumference of the cylindrical wall of hollow body 102. In some embodiments, baffle 110 includes openings configured to allow at least gasses in a flow of matter to separate from liquids and/or solids that are included in the flow. One or more gasses are pulled through baffle 110 and out suction port 106. In some embodiments, baffle 110 includes a solid surface located proximal to input port 104. The solid surface included in baffle 110 is used to prevent liquids and/or solids in the flow from being pulled directly from input port 104 to suction port 106 by allowing time for gravity to act on the liquids and/or solids before they reach an opening in baffle 110. In some embodiments, a baffle 110 comprises both a solid surface portion and a portion with an opening. In these embodiments, the solid surface portion of the baffle 110 is positioned relative to the input port 104 in such a way that gravity acts on a liquid and/or solid within the cyclonic flow before a suction force through suction port 106 draws the liquid and/or solid out of the opening portion of the baffle 110. The solid surface portion of the baffle 110 is thus configured to prevent suction of liquid and/or solid matter out of suction port 106 while allowing time for gravity to act on the liquids and/or solids as they traverse the solid surface of baffle 110. The effect of gravity within the cavity of the hollow body 102 on liquids and/or solids causes them to generally descend (within the input flow) towards collection port 108 and thereby not be suctioned out of the suction port 106.

Shaft 112 is configured to direct a flow of matter in a cyclonic flow. The cyclonic flow along with gravity cause liquids and solids to separate from gasses included in the flow of matter. In some embodiments, shaft 112 includes a member disposed within the cylindrical cavity of hollow body 102. The member of shaft 112 is positioned within the cavity of hollow body 102 so that the cavity of hollow body 102 surrounding the central member of shaft 112 comprises an annular cavity shape between shaft 112 and hollow body 102 cavity wall.

Shaft 112 is configured to direct liquids and/or solids that are in the flow so that they pass through the annular cavity between the shaft 112 and hollow body 102 cavity wall before dropping out collection port 108. In some embodiments, shaft 112 includes a tapered section or conical end disposed in the cavity of hollow body 102. In some embodiments, shaft 112 includes a plurality of sections having different diameters. The plurality of sections, for example, include a first cylindrical section that defines a first portion of the annular section of the cavity the hollow body 102 and a second section that defines a second portion of the annular cavity. Tapered and cylindrical sections of shaft 112 are configured to direct the flow within hollow body 102 in a cyclonic flow pattern. In some embodiment, baffle 110 is integral to shaft 112.

Figure 2A:
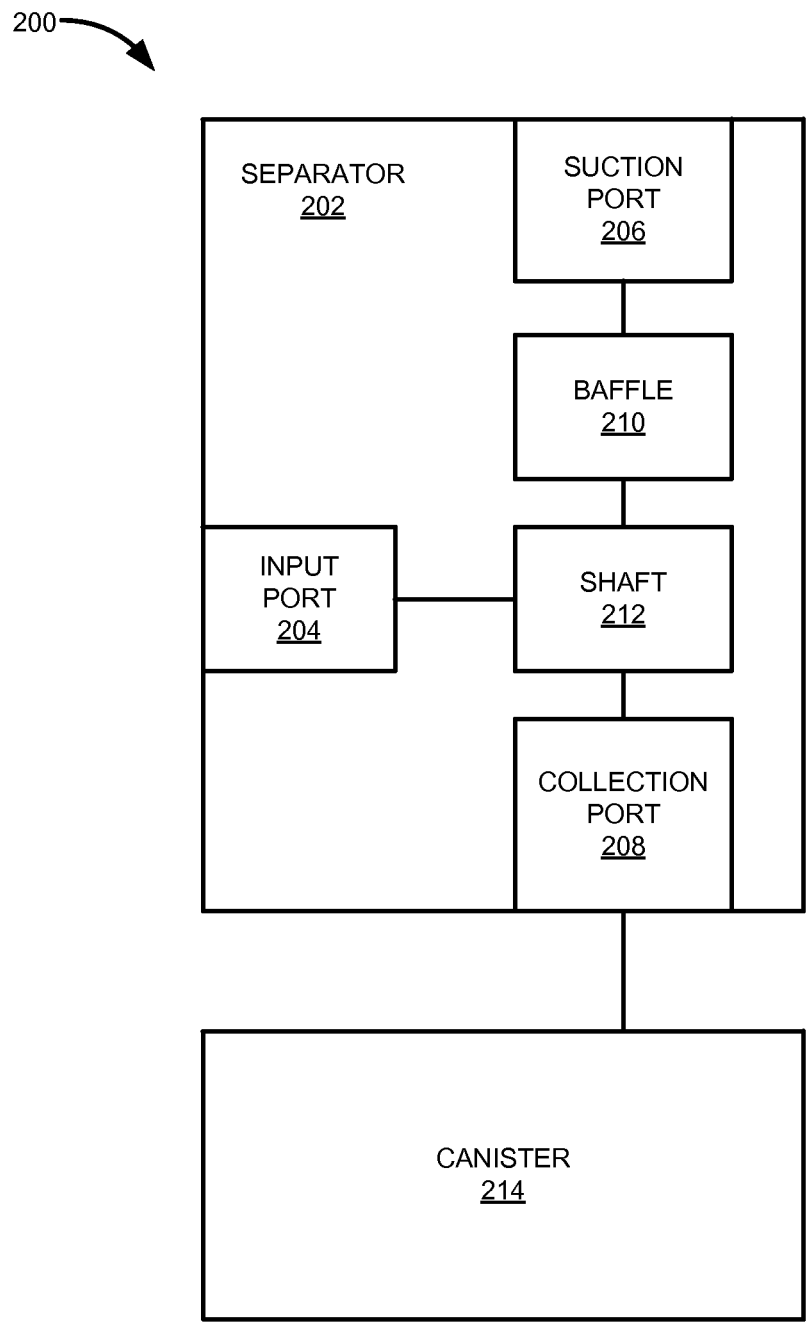
FIG. 2A is a block diagram illustrating a separator and canister system.

FIG. 2A is a block diagram illustrating separator and canister system 200. Separator 202 is an example of separator 100; however, separator 202 may include alternative configurations and methods of operation. Separator and canister system 200 may include separator 202 and canister 214.

In some embodiments, separator 202 comprises input port 204, suction port 206, collection port 208, baffle 210 and shaft 212.

In some embodiments, separator 202 comprises a generally cylindrical cavity and a cavity wall. Non-limiting examples of other suitable cavity shapes for separator 202 include spherical and ovoid cylindrical shapes.

Separator 202 is configured to generate a vortex flow within the cavity of separator 202. The cavity of separator 202 includes a first end and a second cavity end. In some embodiments, the cavity is configured to have a wide end and a narrow end. The wide end is coupled to the second end of the generally cavity. In some embodiments, the separator 202 is configured to operate with the first end positioned upwards.

Input port 204 is configured to direct a flow of matter into separator 202. Input port 204 also directs the flow of matter towards shaft 212. The flow of matter may include liquids, solids and gasses, including combinations thereof in varying ratios. Some constituents of the flow of matter may include surgical byproducts. A flow of matter is induced into input port 204 by suction received from a suction source. In some embodiments, input port 204 is integral to separator 202. Input port 204 is disposed in the cavity wall near the first end of the generally cylindrical cavity of separator 202. Input port 204 is disposed off-axis from an axis defined by the longitudinal center of the generally cylindrical cavity of the body. In an embodiment, input port 204 may include fittings such as, barbed or quick-disconnect type fittings, for coupling input port 204 to a suction tip or surgical device. In some embodiments, input port 204 is configured and positioned to generate a vortex of flow within the cavity of the separator 202.

Suction port 206 is configured to couple to a suction source. In certain embodiments, the suction source may include a vacuum pump, aspirator, and/or a positive pressure operated suction source—such as suction sources that take advantage of Venturi or Coanda effect. Suction from a suction source is transferred from suction port 206 to input port 204. Suction port 206 is disposed near the first cylindrical cavity end. Suction port 206 provides suction received from a suction source for operating separator and canister system 200. In some embodiments, suction port 206 may include fittings configured to attach tubing. For example, barbed or quick-disconnect type fittings are used to couple tubing to suction port 206. The tubing is used to couple suction port 206 to a suction source or to an input port 204 of another separator.

Collection port 208 is configured to expel at least liquids and/or solids separated from a flow of matter received at input port 204. Collection port 208 is disposed at the narrow end of the conical cavity of the hollow body of separator 202. Collection port 208 is configured to couple separator 202 to canister 214. In some embodiments, collection port 208 includes a mounting ring configured to form a seal when separator 202 is coupled to canister 214, tubing, piping or some other element configured to dispose of at least liquids and/or solids. In some embodiments, collection port 208 may include fittings, such as barbed or quick disconnect type fittings for, for coupling collection port 208 to canister 214 or tubing.

Baffle 210 is configured to allow gasses to be pulled out suction port 206 from liquids and/or solids in a flow of matter received at input port 204. Baffle 210 is configured to prevent liquids or solids in a flow of matter received at input port 204 from being pulled directly from input port 204 to suction port 206 without traversing at least a first portion of a circumference of separator 202. Baffle 210 is disposed between input port 204 and suction port 206. In an embodiment, baffle 210 includes a plurality of openings to allow at least the gasses in a flow of matter to be pulled out suction port 206. In an embodiment, baffle 210 includes a solid surface located proximal to input port 204. The solid surface is configured to prevent liquids and/or solids in a flow of matter from being pulled directly from input port 204 to suction port 206 without first traversing at least a portion of separator 202 as described with reference to FIG. 1.

Shaft 212 is configured to form an annular cavity between shaft 212 and separator 202 within the cavity of separator 202. In some embodiments, shaft 212 includes a cylindrical central member disposed within the generally cylindrical cavity of separator 202. Shaft 212 is configured to generate a vortex flow within separator 202. The vortex flow and gravity cause liquids and/or solids in a flow of matter received at input port 204 to separate from gasses. Liquids and gases within the matter flow are expelled out suction port 206. In an embodiment, shaft 212 may include a tapered section disposed near the conical cavity of separator 202. In some embodiments, shaft 212 may include a plurality of cylindrical sections having different diameters. In some embodiments, the plurality of cylindrical sections may include a first section that defines a first portion of the annular cavity and a second section that defines a second portion of the annular cavity. In some embodiments, baffle 210 is integral to shaft 212.

Canister 214 is configured to receive waste from separator 202. The waste may include at least liquids and/or solids separated from a flow of matter received at input port 204. Canister 214 is used to measure the amount of liquids and/or solids separated from the flow of matter received at input port 204. Canister 214 is configured to permit the safe collection, transportation and disposal of waste. In some embodiments, canister 214 may include a valve configured to activate when canister 214 is filled to a pre-determined volume. The valve is used to prevent waste from leaving canister 214 during transportation. In some embodiments, canister 214 may include a commercially available canister.

Figure 2B:
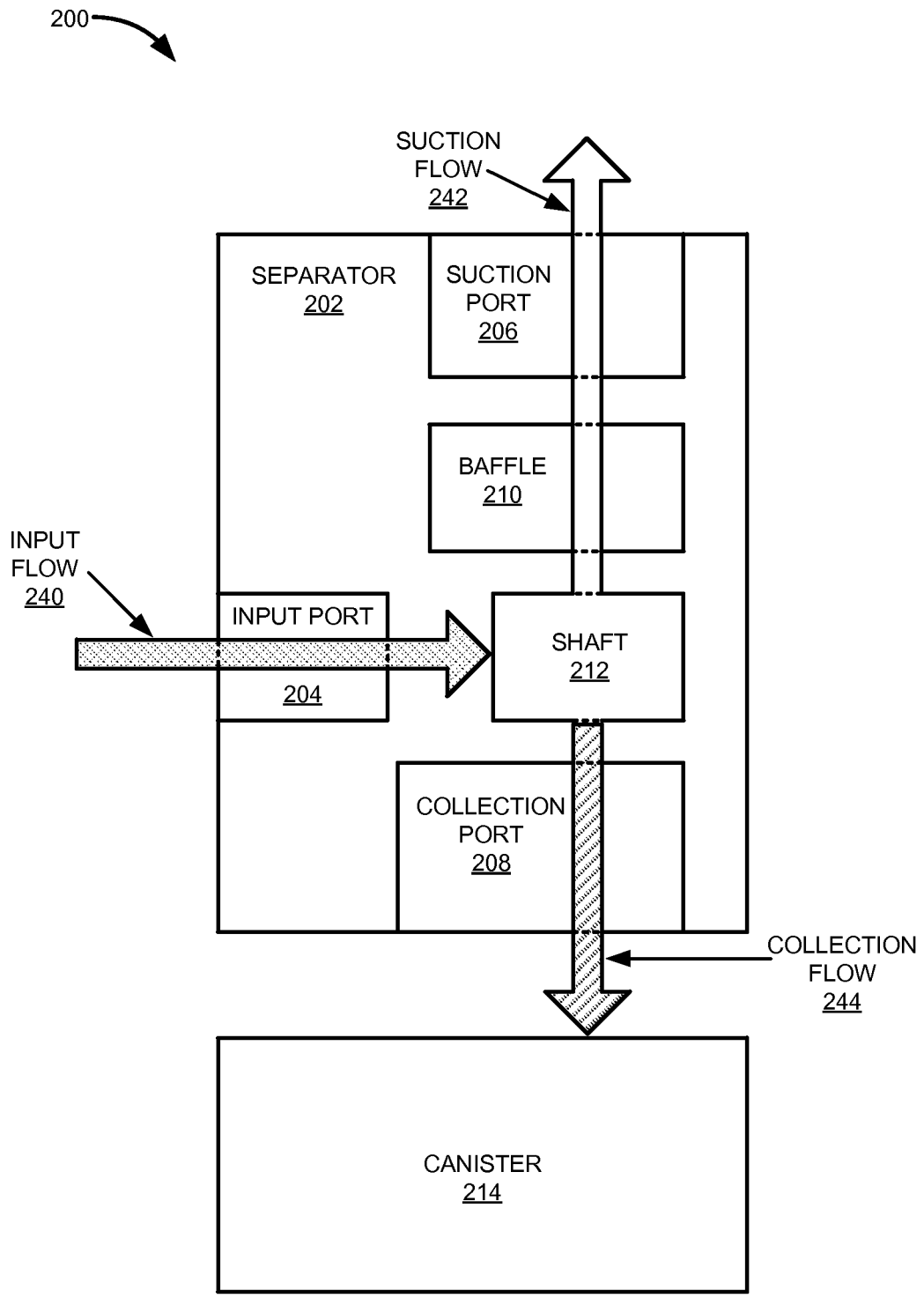
FIG. 2B is a diagram illustrating the operation of a separator and canister system.

FIG. 2B is a diagram illustrating the operation of separator and canister system 200. In addition to the elements illustrated in FIG. 2A, FIG. 2B includes input flow 240, suction flow 242 and collection flow 244.

In operation, a suction source is coupled to suction port 206 to generate suction flow 242. The suction source may include a vacuum pump, aspirator or a Coanda based suction generator. Suction flow 242 generates a flow within separator 202. Suction flow 242 induces input flow 240 to enter input port 204. Input flow 240 may include liquids, solids, and gasses, including combinations thereof in varying ratios. Some constituents of input flow 240 may include surgical byproducts. Suction flow 242 may generate a cyclonic or vortex flow within separator 202 in order to separate liquids, solids and gasses from input flow 240.

Shaft 212 in conjunction with separator 202 is configured to generate a cyclonic or vortex flow from input flow 240 using suction flow 242. Baffle 210 may prevent input flow 240 from passing directly from input port 204 to suction port 206 without first traversing at least a portion of separator 202. The cyclonic flow, along with gravity, separates collection flow 244 and suction flow 242 from input flow 240. One or more gasses are separated from input flow 240 is pulled out suction port 206 as suction flow 242.

Suction flow 242 is directed out of separator 202 by suction port 206. Suction port 206 is configured to exhaust at least suction flow 242 from separator 202. In some methods of operation, suction port 206 expels input flow 240, unseparated, out of suction port 206.

Collection flow 244 is directed out of collection port 208. Collection port 208 is configured to expel at least collection flow 244 from separator 202. Collection port 208 is configured to direct collection flow 244 to canister 214.

In some embodiments, canister 214 is connected to a suction source (not shown). The suction transferred to canister 214 from the suction source provides an additional pull on the fluid and solid matter in separator 202 (i.e. in addition to gravity) to facilitate separation of liquid and solid matter (drawn into canister 214) from gas (drawn out through suction port 206).

Figure 3:
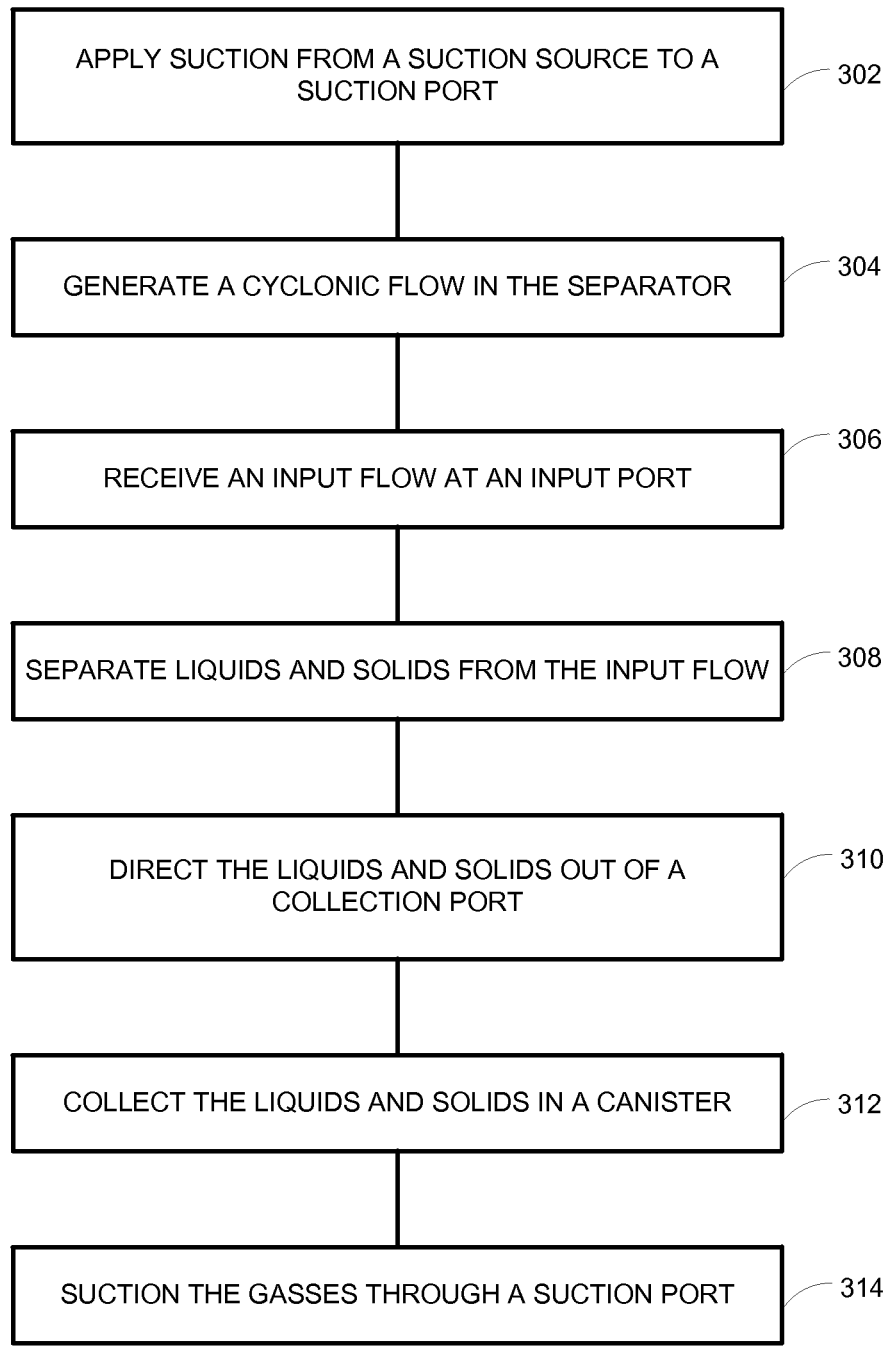
FIG. 3 is a diagram illustrating a method of operating a separator and canister system.

FIG. 3 is a diagram illustrating a method of operating a separator and canister system. The steps illustrated in FIG. 3 is performed by, for example, one or more elements of separator and canister system 200.

In a step 302, a suction source is applied to a suction port. In some embodiments, said suction port is part of a separator system as described herein. In some embodiments, a user connects a suction port to a suction source that comprises an air amplifier based on a Coanda or Venturi effect. In some embodiments, the suction is applied to a suction port of a device configured to separate suctioned matter that was suctioned from a surgical field during a surgical procedure. As applied but not limited to canister system 200, a separator 202 includes suction port 206. Suction port 206 is configured to couple to a suction source capable of providing suction flow 242. A suction source is configured to apply suction flow 242.

In a step 304 a cyclonic or vortex flow is generated by a separator such, as for example, separator 100 or separator 200. A cyclonic or vortex flow is generated from a suction flow applied to a suction port of a separator. In some embodiments, a cyclonic or vortex suction flow is generated when air within the separator is suctioned through the suction port as a result of an application of a suction flow. A shaft within the separator cavity is configured to create a cyclonic flow within the separator, and air within the separator cavity that is suctioned out with the initial application of suction to the separator is drawn around the shaft to form a cyclonic or vortex flow. In some embodiments, the shaft further comprises a conical head that further promotes cyclonic flow. In some embodiments, the cyclonic or vortex flow of suction causes matter comprising a solid, a liquid, a gas, or a combination thereof to be drawn into the separator in a cyclonic or vortex input flow. In some embodiments, the position of the input port further aids in generating a cyclonic or vortex flow of an input flow. In some embodiments, the inlet port is positioned towards the upper portion of the separator. In some embodiments, the inlet port is positioned at an angle such that it directs an inflow essentially directly against an interior wall surface of the separator cavity. As applied but not limited to system 200, separator 202 is configured to generate, from suction flow 242, a cyclonic flow of matter that is received via input port 204.

In a step 306, an input flow is received via an input port. Suction flow generates suction at an input port. Suction flow is at a pressure below an ambient air pressure. Therefore, a suction flow causes input flow which is at around ambient pressure to be received at an input port of the separator device. In some embodiments, the input flow comprises a solid, liquid, a gas, or a combination thereof. In some embodiments, the input flow travels in a cyclone or vortex flow pattern within the separator. As applied but not limited to system 200, input port 204 is configured to receive input flow 240. Suction flow 242 generates suction at input port 204. Suction flow 242 is at a pressure below an ambient air pressure. Therefore, suction flow 242 causes input flow 240 to be received at input port 204.

In a step 308, the components of an input flow comprising a mixture of a solid and/or a liquid with a gas are separated. For example, a separator is configured to separate a solid and/or liquid from a gas of an input flow by directing the heavier constituents (i.e., liquids and/or solids) of the input flow into a cyclonic flow pattern that gravity acts upon to cause these heavier constituents to exit via collection port, while the lighter constituents (i.e. gasses, smoke, aerosols) in the input flow is pulled out of separator by the suction at the suction port. Thus, a collection flow that is released from the separator via a collection port includes at least liquids and/or solids. As applied but not limited to system 200, separator 202 is configured to separate collection flow 244 from input flow 240 by directing the heavier constituents (i.e., liquids and solids) of input flow 240 into a cyclonic flow pattern that gravity acts upon to cause these heavier constituents to exit via collection port 208, while the lighter constituents (i.e. gasses, smoke, aerosols) in input flow 240 are pulled out of separator 202 by the suction at suction port 206. Thus, collection flow 244 includes at least liquids and/or solids.

In a step 310, the separated solid and/or liquid from the input flow are directed into a collection port. For example, a collection port is configured to receive the heavier constituents and direct them to a canister. Liquids and/or solids are collected in a canister. For example, a canister is configured to receive a collection flow (which may include liquids and/or solids) from collection port. As applied but not limited to system 200, collection port 208 is configured to receive the heavier constituents and direct them to collection canister 214.

In a step 312, the separated solid and/or liquid is collected in a collection canister. As applied but not limited to system 200, collection canister 214 is configured to receive collection flow 244 (which may include liquids and solids) from collection port 208.

In a step 314, gasses are suctioned through a suction port. For example, a suction flow may include gasses drawn out of an input flow. Suction port is configured to allow suction flow to be suctioned through suction port. In some embodiments, a separator further comprises a baffle that prevents liquids and/or solids within an input flow to be suctioned from the suction port by the suction flow. As applied but not limited to system 200, suction flow 242 may include gasses. Suction port 206 is configured to allow suction flow 242 to be suctioned through suction port 206.

Figure 4A:
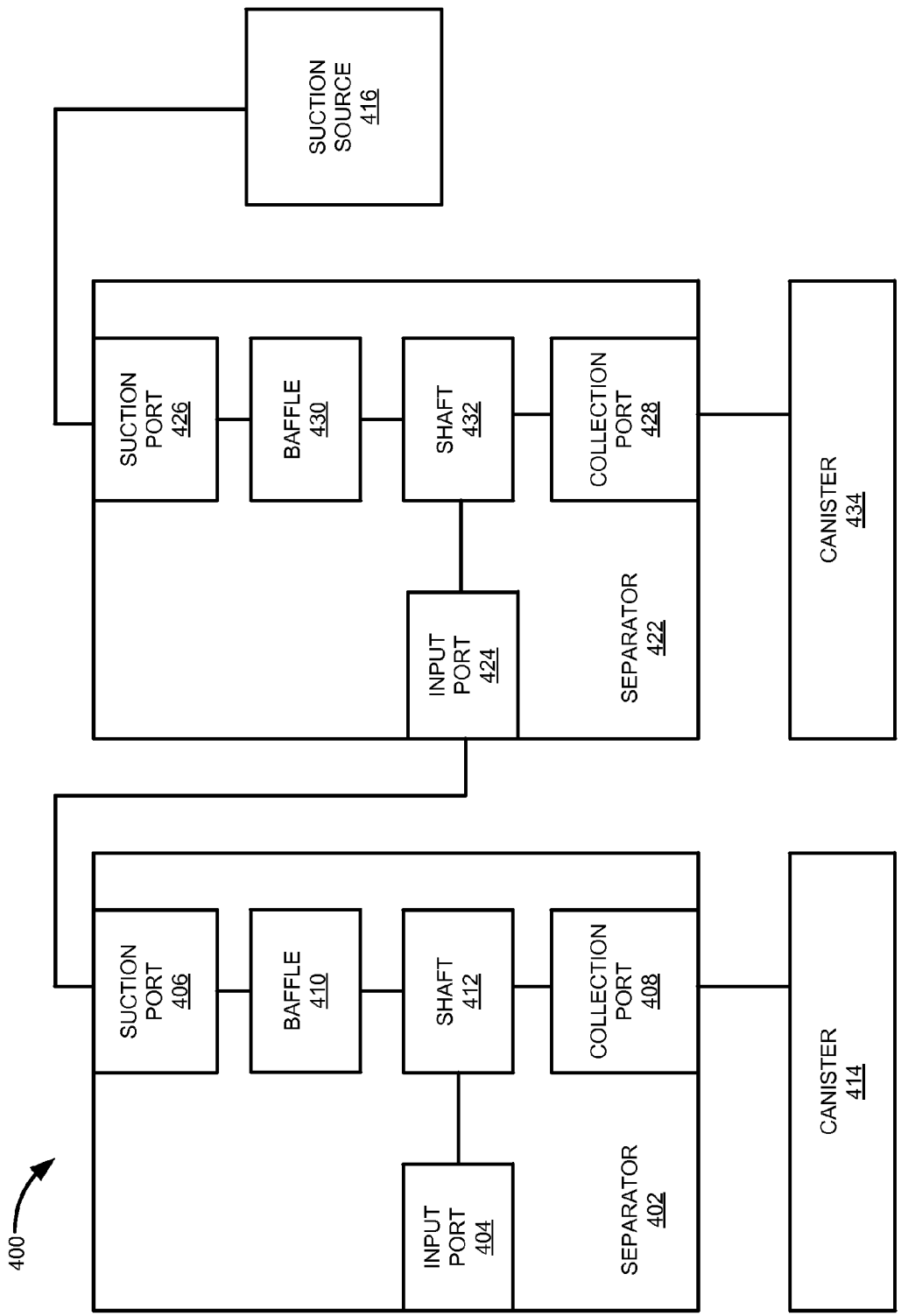
FIG. 4A is a block diagram illustrating a separator system.

FIG. 4A is a block diagram illustrating separator system 400. In this embodiment, one or more separator systems are aligned in series. As shown, separator 402 and separator 422 are examples of separator 202; however separator 402 and separator 422 may include alternative configurations and methods of operation.

In some embodiments, separator system 400 may, for example, include separator 402, canister 414, separator 422, canister 434 and suction source 416.

Separator 402 is configured to generate a vortex flow within the cavity of separator 402. The cavity of separator 402 includes a first end and a second cavity end. In some embodiments, the cavity is configured to have a wide end and a narrow end. The wide end is coupled to the second end of the generally cavity. In some embodiments, the separator 402 is configured to operate with the first end positioned upwards.

Input port 404 is configured to direct a flow of matter into separator 402. Input port 404 directs the flow of matter towards shaft 412. The flow of matter may include liquids, solids and gasses, including combinations thereof in varying ratios. Some constituents of the flow of matter may include surgical byproducts. A flow of matter is induced into input port 404 by suction received from a suction source. In some embodiments, input port 404 is integral to separator 402. Input port 404 is disposed in the cavity wall near the first end of the generally cylindrical cavity of separator 402. Input port 404 is disposed off-axis from an axis defined by the longitudinal center of the generally cylindrical cavity of the body. In an embodiment, input port 404 may include fittings such as, barbed or quick-disconnect type fittings, for coupling input port 404 to a suction tip or surgical device. In some embodiments, input port 404 is configured and positioned to generate a vortex of flow within the cavity of the separator 402.

Suction port 406 is configured to couple to a suction source. In certain embodiments, the suction source may include a vacuum pump, aspirator, and/or a positive pressure operated suction source—such as suction sources that take advantage of Venturi or Coanda effect. Suction from a suction source is transferred from suction port 406 to input port 204. Suction port 406 is disposed near the first cylindrical cavity end. Suction port 406 may provide suction received from a suction source for operating separator and canister system 400. In some embodiments, suction port 406 may include fittings configured to attach tubing. For example, barbed or quick-disconnect type fittings are used to couple tubing to suction port 406. The tubing is used to couple suction port 406 to a suction source or to an input port 404 of another separator.

Collection port 408 is configured to expel at least liquids and/or solids separated from a flow of matter received at input port 404. Collection port 408 is disposed at the narrow end of the conical cavity of the hollow body of separator 402. Collection port 408 is configured to couple separator 402 to canister 414. In some embodiments, collection port 408 includes a mounting ring configured to form a seal when separator 402 is coupled to canister 414, tubing, piping or some other element configured to dispose of at least liquids and/or solids. In some embodiments, collection port 408 may include fittings, such as barbed or quick disconnect type fittings for, for coupling collection port 408 to canister 414 or tubing.

Baffle 410 is configured to allow gasses to be pulled out suction port 406 from liquids and/or solids in a flow of matter received at input port 404. Baffle 410 is configured to prevent liquids or solids in a flow of matter received at input port 404 from being pulled directly from input port 404 to suction port 406 without traversing at least a first portion of a circumference of separator 402. Baffle 410 is disposed between input port 404 and suction port 406. In some embodiments, baffle 410 includes a plurality of openings to allow at least the gasses in a flow of matter to be pulled out suction port 406. In some embodiments, baffle 410 includes a solid surface located proximal to input port 404. The solid surface is configured to prevent liquids and/or solids in a flow of matter from being pulled directly from input port 404 to suction port 406 without first traversing at least a portion of separator 402 as described with reference to FIG. 1.

Shaft 412 is configured to form an annular cavity between shaft 412 and separator 402 within the cavity of separator 402. In some embodiments, shaft 412 includes a cylindrical central member disposed within the generally cylindrical cavity of separator 402. Shaft 412 is configured to generate a vortex flow within separator 402. The vortex flow and gravity cause liquids and/or solids in a flow of matter received at input port 404 to separate from gasses. Liquids and gases within the matter flow are expelled out suction port 406. In an embodiment, shaft 412 includes a tapered section disposed near the conical cavity of separator 402. In some embodiments, shaft 412 includes a plurality of cylindrical sections having different diameters. In some embodiments, the plurality of cylindrical sections includes a first section that defines a first portion of the annular cavity and a second section that defines a second portion of the annular cavity. In some embodiments, baffle 410 is integral to shaft 412.

Canister 414 is configured to receive waste from separator 402. The waste may include at least liquids and/or solids separated from a flow of matter received at input port 404. Canister 414 is used to measure the amount of liquids and/or solids separated from the flow of matter received at input port 404. Canister 414 is configured to permit the safe collection, transportation and disposal of waste. In some embodiments, canister 414 may include a valve configured to activate when canister 414 is filled to a pre-determined volume. The valve is used to prevent waste from leaving canister 414 during transportation. In some embodiments, canister 414 may include a commercially available canister.

Separator 422 may include similar configurations and methods of operation as separator 402. For the sake of brevity, separator 422 will not be described further. Likewise collection canister 434 may include similar configurations and methods of operation as collection canister 414. For the sake of brevity, collection canister 434 will not be described further.

Separator system 400 includes suction source 416. Suction source 416 may be any device configured to generate a pressure below an ambient air pressure. Suction source 416 may include a vacuum pump, aspirator or Coanda based positive pressure operated suction source.

Figure 4B:
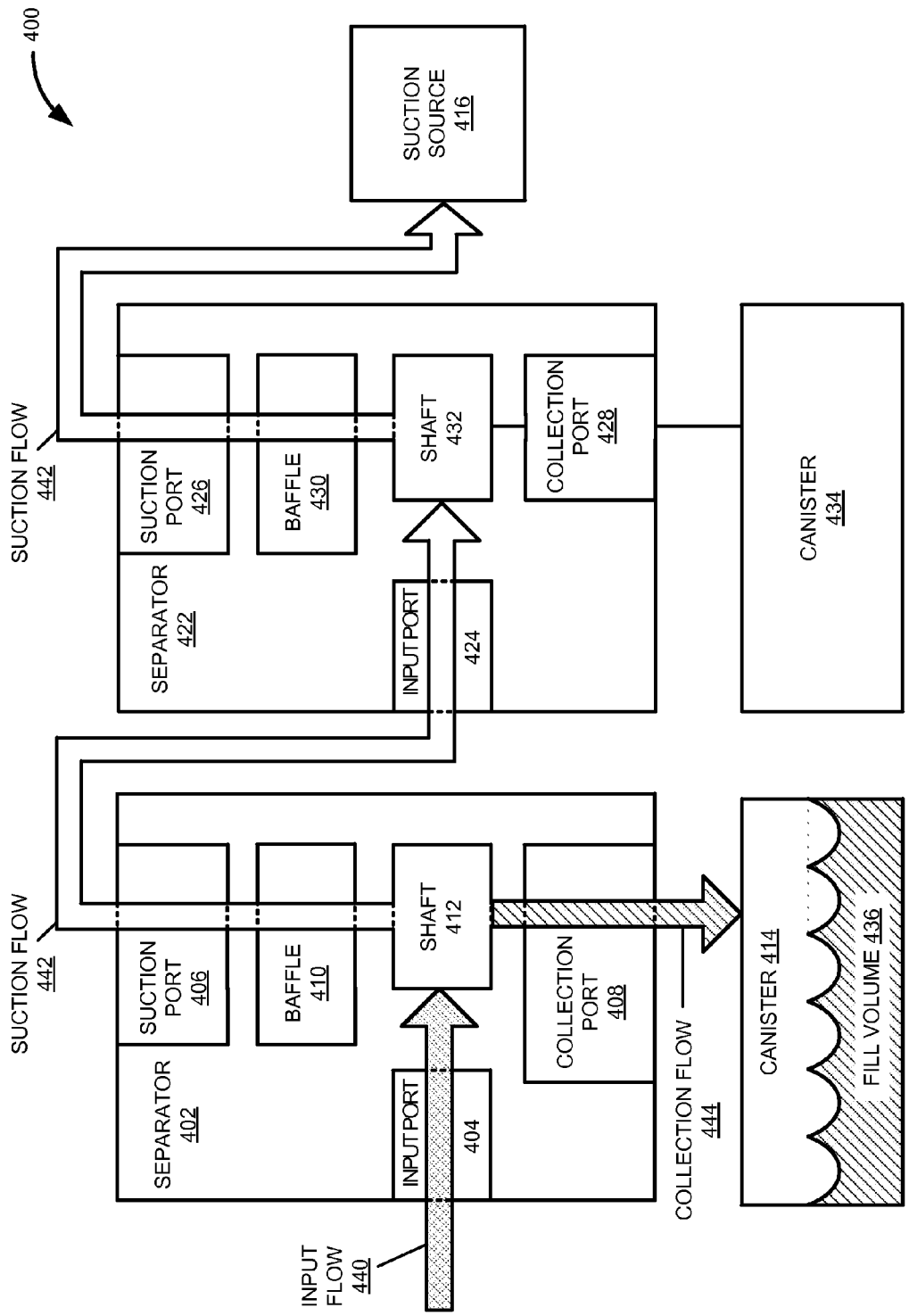
FIG. 4B is a block diagram illustrating the operation of a separator system.

FIG. 4B is a block diagram illustrating an exemplary operation of separator system 400 in a first mode. Separators 402, 422 are configured to direct input flow 440 directly from input port 404 out suction port 406 when canister 414 reaches a predetermined fill volume. As illustrated in FIG. 4B, canister 414 may not have reached a predetermined fill volume. Fill volume 436 is less than the predetermined fill volume.

In operation, suction source 416 supplies suction flow 442 to suction port 426. Separator 422 is configured to transfer suction flow 442 to separator 402. Suction flow 442 creates a pressure near input port 404 that is below an ambient air pressure. The ambient air pressure overcomes the pressure of suction flow 442 thereby inducing input flow 440 into input port 404. Input port 404 is configured to receive input flow 440. Input flow 440 comprises liquids, gasses and solids, including combinations thereof in varying ratios. Input flow 440 may include surgical byproducts. Shaft 412, in combination with an interior cavity of separator 402, creates a cyclonic flow within separator 402 from suction flow 442. The cyclonic flow and gravity causes collection flow 444 to separate from input flow 440. Collection flow 444 comprises at least liquids and/or solids. Collection flow 444 is expelled from collection port 408. Collection port 408 is configured to direct collection flow 444 to canister 444.

Fill volume 436 represents a volume of collection flow 444 contained in canister 414. As illustrated in FIG. 4B, fill volume 436 may not have reached a predetermined fill volume. In this case, separator 402 operates in a first mode of operation. Separator 402 separates suction flow 442 from collection flow 444. In the first mode of operation, suction flow 442 comprises primarily gasses separated from input flow 440.

Suction flow 442 is pulled from separator 402 by suction source 416. Suction flow 442 is passed from suction port 406 to input port 424. Suction flow 442 may comprise primarily liquids and gasses. Separator 402 continues to operate in the first mode of operation until fill volume 436 reaches a predetermined volume.

In some embodiments, separator system 400 comprises a connection between canisters 414 and 434 (not shown). The connection between canisters is configured to transfer a suction force between canister 434 to canister 414 and may comprise any of the means of transmitting suction described herein including, for example, suction tubing. In this embodiment, suction generated by suction source 416 is transmitted to canister 434 of separator 442 and then through the connection between the canisters the suction is transmitted to canister 414. The suction transferred to canister 414 provides an additional pull on the fluid and solid matter in separator 402 (i.e. in addition to gravity) to facilitate separation of liquid and solid matter (drawn into canister 414) from gas (drawn out through suction port 406).

Figure 4C:
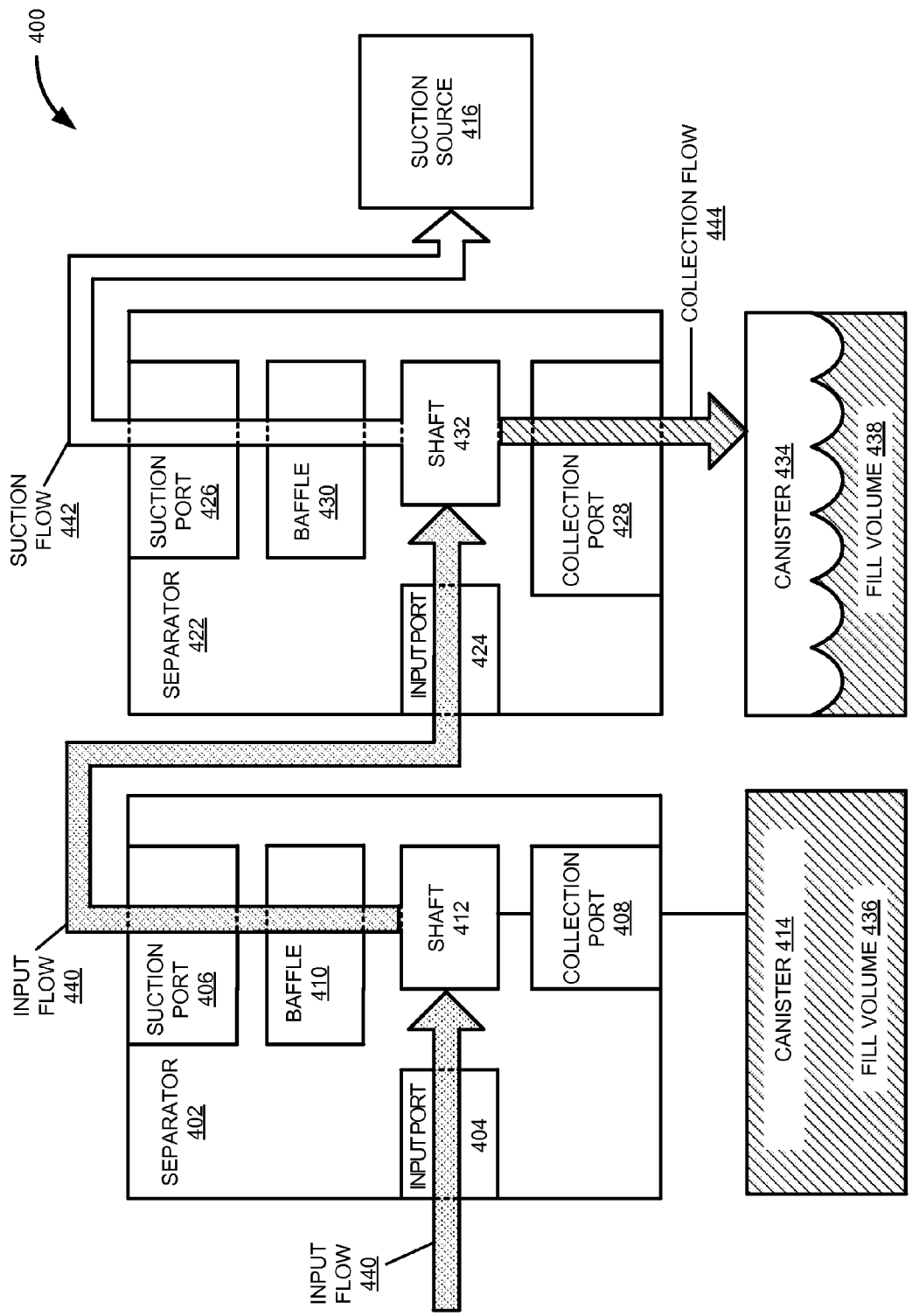
FIG. 4C is a block diagram illustrating the operation of a separator system.

FIG. 4C is a block diagram illustrating an exemplary operation of separator system 400 in a second mode. Separators 402, 422 are configured to pass input flow 440 from input ports 404, 424 to suction ports 406, 426 unseparated when canisters 414, 434 reach predetermined fill volumes. As illustrated in FIG. 4C, fill volume 436 has reached a predetermined fill volume for canister 414. In a second mode of operation, separator 402 passes input flow 440 through suction port 406 to separator 422 unseparated.

In operation, suction source 416 is configured to supply a suction flow 442 to suction port 426. Separator 422 is configured to pass suction flow 442 to separator 402. Suction flow 442 pulls input flow 440 into input port 404. Separator 402 passes input flow 440 from input port 404 to suction port 406 because fill volume 436 has reached a predetermined fill volume for canister 414. Input flow 440 is received by input port 424.

Fill volume 438, as shown, has not reached a predetermined fill volume for canister 434. Separator 422 therefore separates collection flow 444 from suction flow 442. Collection flow 444 may comprise liquids and/or solids from input flow 440. Separator 422 separates suction flow 442 from collection flow 444. Collection flow 444 is expelled out collection port 428. Collection port 428 is coupled to canister 434. Canister 434 is configured to receive collection flow 444 from collection port 428. Suction flow 442 is pulled out suction port 426 by suction source 416.

The systems, devices, and methods described herein are configured to separate a gas from a liquid at a controlled rate. The controlled rate of suction applied by a system increases when one or more flow separation devices are connected as described herein. As described herein, two or more separators in a system are connected "in series" so that suction from a suction source is transmitted from a first separator to a second separator connected to the first separator as described herein. In alternative embodiments, one or more separators are in a system connected "in parallel" such that two or more interconnected separators (connected to each other as described) are both connected to one or more suction sources.

In some embodiments, a suction transmitted through one or more separators connected in a system is greater than a suction transmitted through a single separator. For example, if a surgical suction instrument is connected to the separator system, an increased suction force is transmitted at the surgical suction instrument when it is connected to any the systems of FIG. 4A-4C than when the surgical suction instrument is connected to any of the systems of FIG. 2A-2C (i.e. greater suction experienced at the surgical suction instrument when connected to two or more separators in a system as opposed to a connection to only one separator).

When one or more flow separation devices are connected as described herein, a flow rate may be generated of at least about 1 cubic centimeter per second (cc/s), 2 cc/s, 3 cc/s, 4 cc/s, 5 cc/s, 6 cc/s, 7 cc/s, 8 cc/s, 9 cc/s, 10 cc/s, 11 cc/s, 12 cc/s, 13 cc/s, 14 cc/s, 15 cc/s, 16 cc/s, 17 cc/s, 18 cc/s, 19 cc/s, 20 cc/s, 25 cc/s, 30 cc/s, 35 cc/s, 40 cc/s, 45 cc/s, 50 cc/s, 55 cc/s, 60 cc/s, 65 cc/s, 70 cc/s, 75 cc/s, 80 cc/s, 85 cc/s, 90 cc/s, 95 cc/s, 100 cc/s or more. The system may separate gas from liquid at a rate of at least about 5 cc/s. The system may separate gas from liquid at a rate of at least about 10 cc/s. The system may separate gas from liquid at a rate of at least about 20 cc/s. The system may separate gas from liquid at a rate of at least about 30 cc/s. The system may separate gas from liquid at a rate of at least about 40 cc/s. The system may separate gas from liquid as a rate of at least about 50 cc/s.

The one or more flow separation devices as described herein may provide a separation of a flow, such as a separation of a gas and liquid in a flow at a flow rate of about 100 mmHg, 150 mmHg, 200 mmHg, 250 mmHg, 300 mmHg, 350 mmHg, 400 mmHg, 450 mmHg, 500 mmHg, or more. A separate of a flow may occur at a flow rate of at least about 150 mmHg. A separation of a flow may occur at a flow rate of at least about 200 mmHg. A separation of a flow may occur at a flow rate of at least about 250 mmHg. A separation of a flow may occur at a flow rate of at least about 300 mmHg. A separation of a flow may occur at a flow rate of at least about 350 mmHg. A separation of a flow may occur at a flow rate of at least about 400 mmHg. A separation of a flow may occur at a flow rate of at least about 500 mmHg. A separation of a flow may occur at a flow rate from about 150 mmHg to about 350 mmHg. A separation of a flow may occur at a flow rate from about 200 mmHg to about 350 mmHg.

The one or more flow separation devices as described herein may be configured to cyclone a liquid portion of a flow into an outlet port adjacent or attached to canister and to divert a gas portion of a flow through a separate outlet port such as to a filtration device. The one or more flow separation devices or one or more components of the separation device may be disposable. The one or more flow separation devices or one or more components of the separation device may be reusable.

The suction capacity of a surgical instrument operatively coupled to one or more flow separation devices may increase compared to a surgical instrument not operatively coupled. The suction capacity may increase about 1 fold, 1.25 fold, 1.5 fold, 1.75 fold, 2 fold, 2.25 fold, 2.5 fold, 2.75 fold, 3 fold, 3.25 fold, 3.5 fold, 3.75 fold, 4 fold, 4.25 fold, 4.5 fold, 4.75 fold, 5 fold, or more. The suction capacity may increase by at least about 1.25 fold. The suction capacity may increase by at least about 1.5 fold. The suction capacity may increase by at least about 1.75 fold. The suction capacity may increase by at least about 2 fold. The suction capacity may increase by at least about 2.5 fold. The suction capacity may increase by at least about 3 fold.

The suction capacity of a surgical instrument operatively coupled to one or more flow separation devices may increase compared to a surgical instrument not operatively coupled. The suction capacity may increase about 20%, 25%, 30%, 35%, 40%, 45%, 50%, 55%, 60%, 65%, 70%, 75%, 80%, 85%, 90%, 95% or more. The suction capacity may increase at least about 25%. The suction capacity may increase at least about 30%. The suction capacity may increase at least about 35%. The suction capacity may increase at least about 40%. The suction capacity may increase at least about 45%. The suction capacity may increase at least about 50%. The suction capacity may increase at least about 55%. The suction capacity may increase at least about 60%. The suction capacity may increase at least about 65%. The suction capacity may increase at least about 70%. The suction capacity may increase at least about 75%. The suction capacity may increase at least about 80%. The suction capacity may increase at least about 85%. The suction capacity may increase at least about 90%.

The suction capacity of a suction source, such as a passive suction source, operatively coupled to one or more flow separation devices may increase compared to a suction source not operatively coupled. The suction capacity may increase about 1 fold, 1.25 fold, 1.5 fold, 1.75 fold, 2 fold, 2.25 fold, 2.5 fold, 2.75 fold, 3 fold, 3.25 fold, 3.5 fold, 3.75 fold, 4 fold, 4.25 fold, 4.5 fold, 4.75 fold, 5 fold, or more. The suction capacity may increase by at least about 1.25 fold. The suction capacity may increase by at least about 1.5 fold. The suction capacity may increase by at least about 1.75 fold. The suction capacity may increase by at least about 2 fold. The suction capacity may increase by at least about 2.5 fold. The suction capacity may increase by at least about 3 fold.

The suction capacity of a suction source, such as a passive suction source, operatively coupled to one or more flow separation devices may increase compared to a suction source not operatively coupled. The suction capacity may increase about 20%, 25%, 30%, 35%, 40%, 45%, 50%, 55%, 60%, 65%, 70%, 75%, 80%, 85%, 90%, 95% or more. The suction capacity may increase at least about 25%. The suction capacity may increase at least about 30%. The suction capacity may increase at least about 35%. The suction capacity may increase at least about 40%. The suction capacity may increase at least about 45%. The suction capacity may increase at least about 50%. The suction capacity may increase at least about 55%. The suction capacity may increase at least about 60%. The suction capacity may increase at least about 65%. The suction capacity may increase at least about 70%. The suction capacity may increase at least about 75%. The suction capacity may increase at least about 80%. The suction capacity may increase at least about 85%. The suction capacity may increase at least about 90%.

Figure 5:
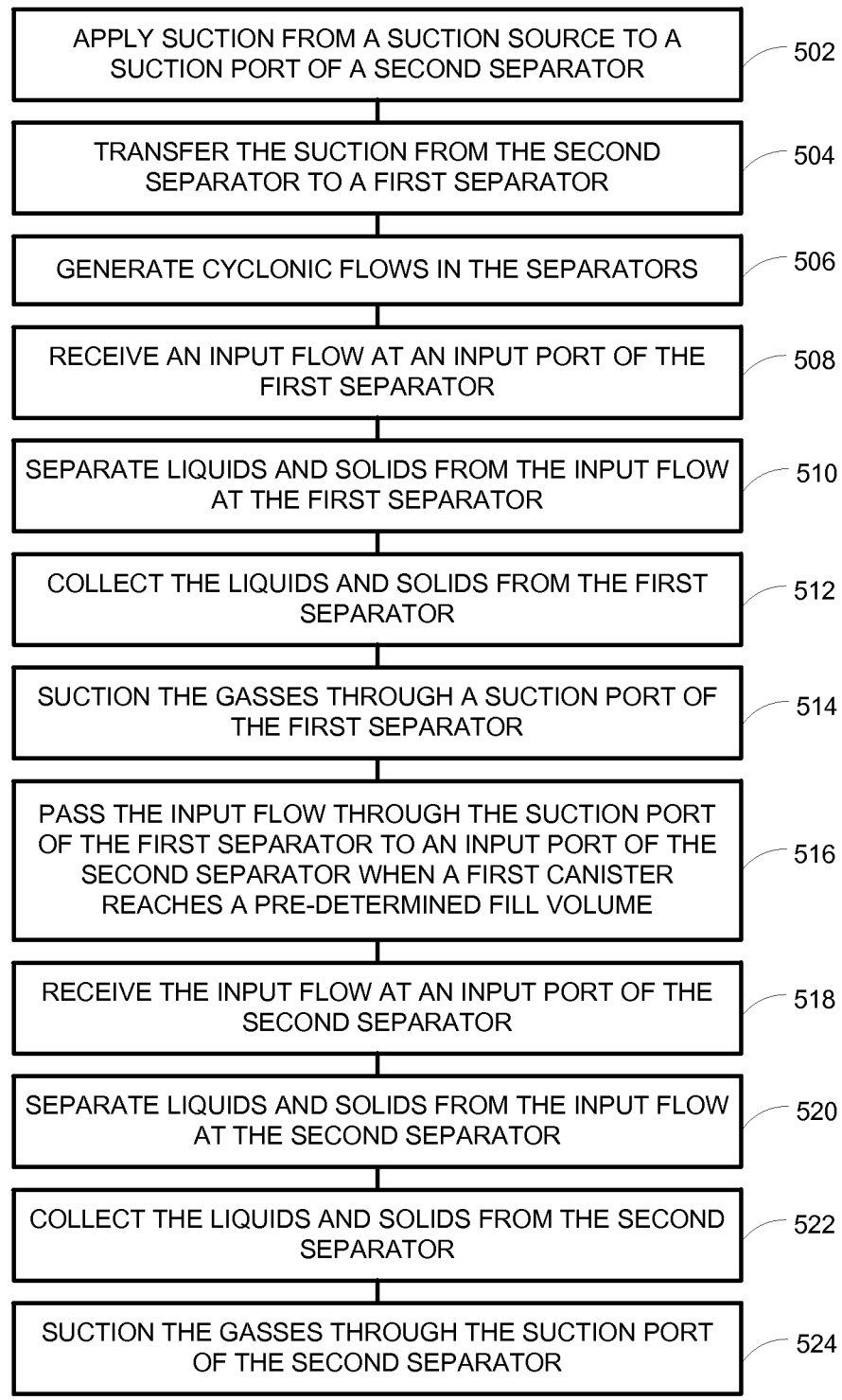
FIG. 5 is a diagram illustrating a method of operating a separator system.

FIG. 5 is a diagram illustrating an exemplary method of operating a separator system in series. The steps illustrated in FIG. 5 is performed by, for example, one or more elements of separator system 400.

In steps 502 and 504, a single suction source applies suction to a suction port of a second separator which is connected to a first separator. The first separator is connected to the second separator such that a suction flow generated within the second separator is translated to the first separator. In some embodiments, the input port of the second separator is connected to the suction port of the first separator by a suction conduit such as standard suction tubing. A suction source is directly applied to a suction port of a second separator generating a suction flow that is transmitted to the first separator. As applied but not limited to system 400, suction source 416 is configured to supply suction. Suction port 426 is configured to receive suction flow 442 from suction source 416. Separator 422 is configured to transfer suction flow 442 from input port 424 to suction port 406.

In a step 506, a cyclonic or vortex flow is generated in both separators. The first and second separators are configured, as described herein, to generate a cyclonic or vortex suction flow when a suction source is applied to both separators. As applied but not limited to system 400, separators 402, 422 are configured to generate from suction flow 442, a cyclonic flow of matter that is received via input port 404.

In a step 508, an input flow is received at an input port of the first separator. As applied but not limited to system 400, input port 404 is configured to receive input flow 440. Suction flow 442 has a pressure below an ambient air pressure. This pressure difference is configured to cause input flow 440 to flow into input port 404.

In a step 510, liquids and/or solids is separated from the input flow at the first separator as a suction flow is transmitted from the second separator. As applied but not limited to system 400, separator 402 is configured to separate suction flow 442 by directing the heavier constituents (i.e., liquids and solids) of input flow 440 into a cyclonic flow pattern that gravity acts upon to cause these heavier constituents to exit via collection port 408, while the lighter constituents (i.e., gasses, smoke, aerosols) in input flow 440 are pulled out of separator 402 by the suction at suction port 406. Thus, collection flow 444 includes at least liquids and solids.

In a step 512, liquids and/or solids from the first separator is collected. For example, as described, a collection port is configured to receive the heavier constituents and direct them to a canister. As applied but not limited to system 400, collection port 408 is configured to receive the heavier constituents and direct them to collection canister 414. Separator 402 is coupled to collection canister 414. Collection canister 414 is configured to receive collection flow 444 from collection port 408. Separator 402 is configured to expel collection flow 444 to collection canister 414 so long as fill volume 436 has not reached a predetermined level.

In a step 514 one or more gasses are suctioned through a suction port of the first separator. As applied but not limited to system 400, suction flow 442 may include gasses separated from input flow 440 by separator 402. Suction port 406 is configured to pass suction flow 442 from separator 402.

In a step 516, the input flow is passed through the suction port of the first separator to an input port of the second separator when a first canister reaches a predetermined fill volume. As applied but not limited to system 400, separator 402 is configured to pass input flow 440 from suction port 406 to input port 424 unseparated when fill volume 436 reaches a predetermined fill volume.

In a step 518, the input flow is received at an input port of a second separator. As applied but not limited to system 400, input port 424 is configured to receive input flow 440.

In a step 520, liquids and/or solids is separated from the input flow at the second separator. As applied but not limited to system 400, separator 422 is configured to separate suction flow 442 from collection flow 444. Suction flow 442 may comprise primarily gasses separated from input flow 440. Collection flow 444 may comprise primarily liquids and/or solids separated from input flow 440.

In a step 522, liquids and/or solids are collected from the second separator. As applied but not limited to system 400, separator 422 is coupled to canister 434. Canister 434 is configured to receive collection flow 444. Collection port 428 is configured to direct collection flow 444 to canister 434. As applied but not limited to system 400.

In a step 524, one or more gasses are suctioned through the suction port of the second separator. As applied but not limited to system 400, suction flow 442 may comprise primarily gasses separated from input flow 440. Separator 422 is configured to pass suction flow 442 through suction port 426.

Figure 6:
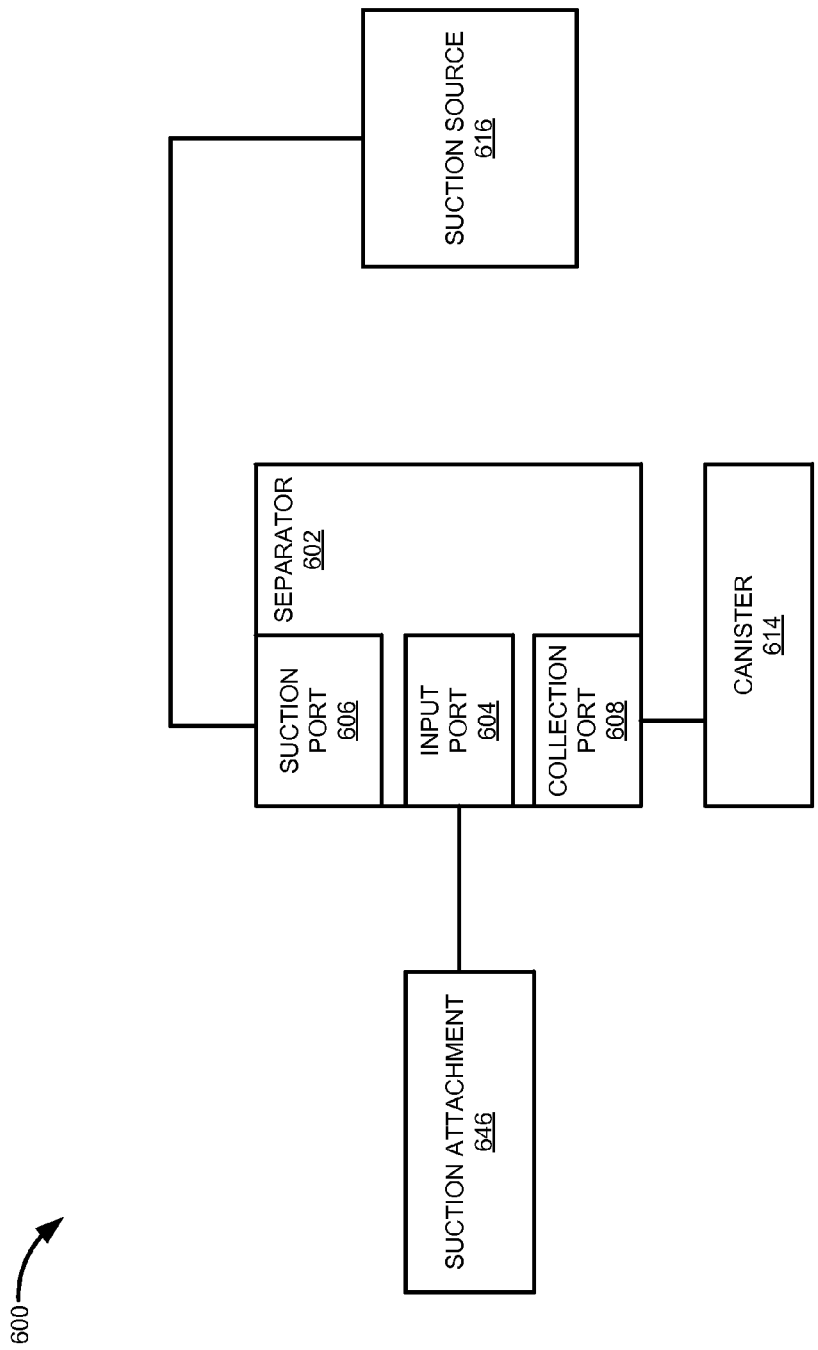
FIG. 6 is a block diagram illustrating a suction system.

FIG. 6 is a block diagram illustrating suction system 600. Suction system 600 includes separator 602, collection canister 614, suction source 616 and suction attachment 646. Separator 602 is an example of separator 100, separator 202, separator 402 and separator 422; however, separator 602 may include alternative configurations and methods of operation. Collection canister 614 is an example of collection canister 214, collection canister 414 and collection canister 434; however, collection canister 614 may include alternative configurations and methods of operation. Suction source 616 is an example of suction source 416; however, suction source 616 may include alternative configurations or methods of operation.

In some embodiments, separator 602 includes input port 604, suction port 606 and collection port 608.

In some embodiments, input port 604 is integral to a body included as part of separator 602. Input port 604 may integral to separator 602. Input port 604 is located off-axis from an axis defined by the longitudinal center of the cylindrical cavity. Input port 604 may be configured to direct a flow of matter along the cylindrical cavity wall. By directing the flow of matter along the cylindrical cavity wall, liquids and gasses may cling to the wall of the cavity due to the effects of centripetal forces. Input port 604 is configured to receive a flow of matter. The flow of matter is pulled into input port 604 by the pressure difference between the ambient air pressure and the lower pressure provided by suction source 616. In some embodiments, input port 604 may include fittings configured to attach tubing. For example, barbed or quick-disconnect type fittings may be used to couple tubing to input port 604.

Suction port 606 is configured to couple to suction source 616. In certain embodiments, suction source 616 may include a vacuum pump, aspirator, and/or a positive pressure operated suction source—such as suction sources that take advantage of Venturi or Coanda effect. Suction from suction source 616 creates suction at input port 604. Input port 604 is configured to receive a flow of matter. The flow of matter is pulled into input port 604 by the pressure difference between the ambient air pressure and the lower pressure provided by suction source 616. The flow of matter may include liquids, solids, and gasses, including combinations thereof in varying ratios. In some embodiments, input port 604 may include fittings configured to attach tubing. For example, barbed or quick-disconnect type fittings may be used to couple tubing to input port 604.

Collection port 608 is configured to expel a collection flow. The collection flow may include at least liquids and solids. Collection port 608 is disposed at the narrow end of the conical cavity of separator 602. Collection port 608 is coupled to collection canister 614. Collection canister 614 may be used to measure the matter collected from separator 602. Collection canister 614 may also be used for the safe collection, transportation, and disposal of waste received from separator 602. In some embodiments, collection port 608 may include a mounting ring configured to form a seal between collection port 608 and collection canister 614.

Suction attachment 646 is configured to couple to separator 602. Suction attachment 646 may couple to input port 604 using flexible tubing or piping to maintain maneuverability of suction attachment 646. In some embodiments, suction attachment 646 may be configured for handheld operation. In some embodiments, suction attachment 646 may be configured to couple to a surgical instrument.

In operation, suction source 616 supplies suction to suction port 606. Suction source 616 creates a cyclonic flow within separator 602. Suction attachment 646 is coupled to input port 604. Input port 604 is configured to couple to suction attachment 646. Separator 602 is configured to transfer suction from suction source 616 to suction attachment 646. Suction attachment 646 is configured to receive a flow a flow of matter. The flow of matter is pulled into suction attachment 646 by suction source 616. Separator 602 is configured to receive the flow of matter from suction attachment 646 at input port 604. Separator 602 is configured to separate liquids and solids from gasses in the flow of matter. Collection port 608 is coupled to collection canister 614. Collection port 608 directs a collection flow to collection canister. The collection flow may include at least liquids and solids. A suction flow is pulled out suction port 606 by suction from suction source 616. The suction flow may comprise primarily gasses. However, in some examples, the suction flow may comprise liquids, solids and gasses.

Figure 7:
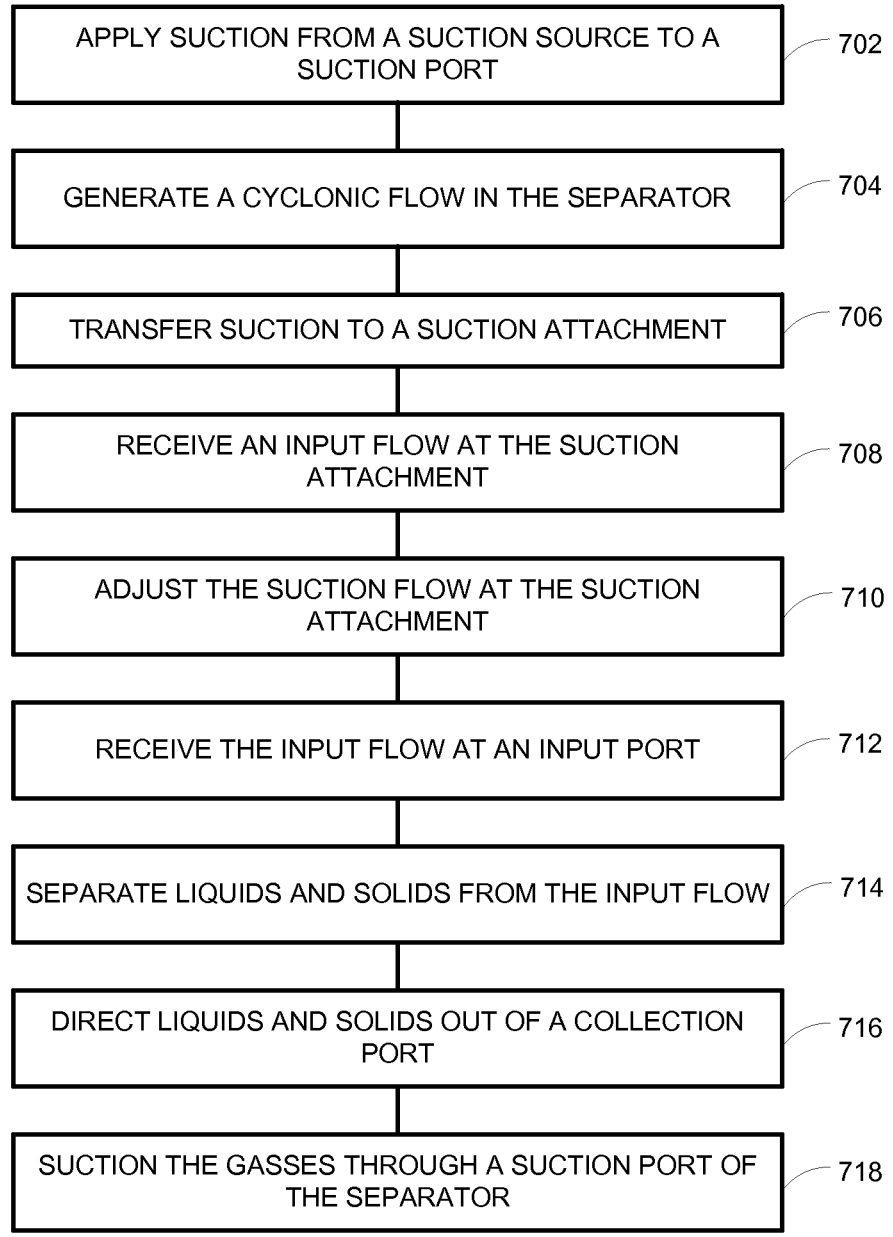
FIG. 7 is a diagram illustrating a method of operating a suction system.

FIG. 7 is a diagram illustrating a method of operating a suction system. The steps illustrated in FIG. 7 may be performed by, for example, one or more elements of suction system 600.

In a step 702, a suction source is applied to a suction port. As applied but not limited to system 600, separator 602 includes suction port 606. Suction port 606 is configured to couple to suction source 616. Suction source 616 may be configured to apply a suction flow to separator 602.

In a step 704, cyclonic flow is generated in a separator. As applied but not limited to system 600, separator 602 is configured to generate, from a suction flow, a cyclonic flow of matter that is received via input port 604.

In a step 706, suction is transferred to a suction attachment. As applied but not limited to system 600, separator 602 is configured to transfer suction from suction source 616 to suction attachment 646.

In a step 708, an input flow is received at the suction attachment. As applied but not limited to system 600, suction attachment 646 is configured to receive an input flow created by suction source 616.

In a step 710, suction flow is adjusted at the suction attachment. As applied but not limited to system 600, suction attachment 646 may be configured to adjust suction delivered at suction attachment 646. Suction source 616 may be configured to maintain a consistent suction supply. Separator 602 continues to function while suction is adjusted by suction attachment 646.

In a step 712, an input flow is received at an input port. As applied but not limited to system 600, input port 604 is coupled to suction attachment 646. Input port 604 is configured to receive an input flow from suction attachment 646.

In a step 714, liquids and solids are separated from the input flow. As applied but not limited to system 600, separator 602 is configured to separate a collection flow from the input flow by directing the heavier constituents (i.e., liquids and solids) of the input flow into a cyclonic flow pattern that gravity acts upon to cause these heavier constituents to exit via collection port 608, while the lighter constituents (i.e., gasses, smoke, aerosols) in the input flow are pulled out of separator 602 by the suction at suction port 606.

In a step 716, liquids and solids are directed out of a collection port. As applied but not limited to system 600, collection port 608 is configured to receive the heavier constituents and direct them to collection canister 614. Gases are suctioned through a suction port of the separator (718). For example, separator 602 is configured to separate gasses from the input flow received at input port 604. Suction source 616 is configured to suction at least gasses separated from the input flow from suction port 606.

FIG. 8A is an exploded-view diagram illustrating separator 800. Separator 800 is an example of separator 100, separator 202, separator 402, separator 422 and separator 602; however, separator 800 may include alternative configurations and methods of operation.

In some embodiments, separator 800 includes body 802, input port 804, suction port 806, collection port 808, baffle 810, vortex element 812, mounting base 846 and mounting ring 848.

Body 802 includes a cylindrical wall defining a cylindrical cavity. The cylindrical wall includes a first cylindrical cavity end and a second cylindrical cavity end. Body 802 also forms a conical cavity. The conical cavity has a wide end and a narrow end. The wide end is mated to the second cylindrical cavity end of body 802. In some embodiments, body 802 is configured to operate with the first cylindrical cavity end up. Body 802 is configured to allow gravity to pull at least liquid and solids separated from a flow of matter out collection port 808, while gasses separated from the flow of matter are pulled by suction out of suction port 806.

Input port 804 is configured to receive a flow of matter. The flow of matter may be induced into separator 800 via suction port 806 by a suction or vacuum source. Input port 804 is configured to direct a flow of matter along the cylindrical cavity wall. By directing the flow of matter along the cylindrical cavity wall, liquids and gasses may cling to the wall of the cavity due to the effects of centripetal forces. Input port 804 is integral to body 802. Input port 804 is disposed in the cylindrical cavity wall of body 802. Input port 804 is located off-axis from an axis defined by the longitudinal center of the cylindrical cavity.

Suction port 806 is configured to couple to suction source 816. In certain embodiments, suction source 816 may include a vacuum pump, aspirator, and/or a positive pressure operated suction source—such as suction sources that take advantage of Venturi or Coanda effect. Suction from suction source 816 creates suction at input port 804. Input port 804 is configured to receive a flow of matter. The flow of matter is pulled into input port 804 by the pressure difference between the ambient air pressure and the lower pressure provided by suction source 816. The flow of matter may include liquids, solids, and gasses, including combinations thereof in varying ratios. In some embodiments, input port 804 may include fittings configured to attach tubing. For example, barbed or quick-disconnect type fittings may be used to couple tubing to input port 804.

Collection port 808 is configured to expel a collection flow. The collection flow may comprise at least liquids and solids. Collection port 808 is disposed at the narrow end of the conical cavity of body 802. In an embodiment, collection port 808 may be configured to couple to a collection canister. A collection canister may be used to measure the matter collected from separator 800. A collection canister may also be used for the safe collection and disposal of waste received from separator 800. In some embodiments, collection port 808 may be coupled to tubing or piping to direct matter to a waste drain. In some embodiments, collection port 808 may include mounting ring 848 configured to form a seal between collection port 808 to tubing or a collection canister.

Baffle 810 is configured to prevent liquids or solids in the flow from being pulled directly from input port 804 to suction port 806 without traversing at least a first portion of a circumference of the cylindrical wall of separator body 802. Baffle 810 is disposed between input port 804 and suction port 806. Baffle 810 includes passageways configured to allow at least gasses in a flow of matter to separate from liquids and solids that maybe included in the flow. Gasses may be pulled through baffle 810 and out suction port 806. Baffle 810 includes a solid surface located proximal to input port 804 configured to direct the flow to traverse at least a first portion of a circumference of the cylindrical wall of body 802. The solid surface included in baffle 810 may to prevent liquids and solids in the flow from being pulled directly from input port 804 to suction port 806 by allowing time for gravity to act on the liquids and solids before they reach an opening in baffle 810. By allowing time for gravity to act on the liquids and solids as they traverse the solid surface of baffle 810, the liquids and solids can descend towards collection port 808 and thereby not be suctioned out of the suction port 806.

Vortex element 812 is configured to allow a collection flow to pass through the annular cavity before dropping out collection port 808. The collection flow may comprise at least liquids and solids. Vortex element 812 includes a cylindrical central member disposed within the cylindrical cavity of body 802. The cylindrical central member forms an annular cavity between vortex element 812 and body 802. Vortex element 812 includes a tapered section disposed in the conical cavity of body 802. Vortex element 812 includes a plurality of cylindrical sections having different diameters. The plurality of cylindrical sections includes a first section that defines a first portion of the annular cavity and a second section that defines a second portion of the annular cavity. The tapered and cylindrical sections may be configured to direct the flow within body 802 in a cyclonic flow pattern. Baffle 810 is integral to vortex element 812.

Mounting base 846 is configured to allow separator 800 to be assembled. Mounting base 846 is configured to couple to body 802. Mounting base 846 is configured to couple to mounting ring 848.

Mounting ring 848 is configured to operate as a seal for suction port 806. Mounting ring 848 may be made from a flexible material that forms a seal between separator 800 and a coupling to a suction source.

FIG. 8B is a diagram illustrating vortex element 800. Vortex element 812 is configured to form an annular cavity between vortex element 812 and body 802. Vortex element 812 is configured to generate a vortex flow within body 802. The vortex flow and gravity may cause liquids and solids in a flow of matter received at input port 804 to separate from gasses. Vortex element 812 includes a cylindrical central member disposed within the generally cylindrical cavity of body 802. Vortex element 812 includes a tapered section disposed near the conical cavity of body 802. Vortex element 812 includes a plurality of cylindrical sections having different diameters. The plurality of cylindrical sections includes a first section that defines a first portion of the annular cavity and a second section that defines a second portion of the annular cavity. Baffle 810 is integral to vortex element 812.

Vortex element 812 includes baffle 810. Baffle 810 is configured to prevent liquids or solids in the flow from being pulled directly from input port 804 to suction port 806 without traversing at least a first portion of a circumference of the cylindrical wall of separator body 802. Baffle 810 is disposed between input port 804 and suction port 806. Baffle 810 includes passageways configured to allow at least gasses in a flow of matter to separate from liquids and solids that maybe included in the flow. Gasses may be pulled through baffle 810 and out suction port 806. Baffle 810 includes a solid surface located proximal to input port 804 configured to direct the flow to traverse at least a first portion of a circumference of the cylindrical wall of body 802. The solid surface included in baffle 810 may to prevent liquids and solids in the flow from being pulled directly from input port 804 to suction port 806 by allowing time for gravity to act on the liquids and solids before they reach an opening in baffle 810. By allowing time for gravity to act on the liquids and solids as they traverse the solid surface of baffle 810, the liquids and solids can descend towards collection port 808 and thereby not be suctioned out of the suction port 806.

FIG. 8C is a top-view diagram illustrating the operation of separator 800. In operation, a suction source coupled to suction port 806 induces input flow 840 within separator

800. Input flow 840 enters separator 800 through input port 804. Baffle 810 includes passageways 850 configured to allow at least gasses to exit separator 800 via collection port 808. Baffle 810 does not include passageways 850 immediately proximal to input port 804 forcing input flow 840 to traverse at least a first portion of a circumference of the interior of body 802.

Figure 8D:
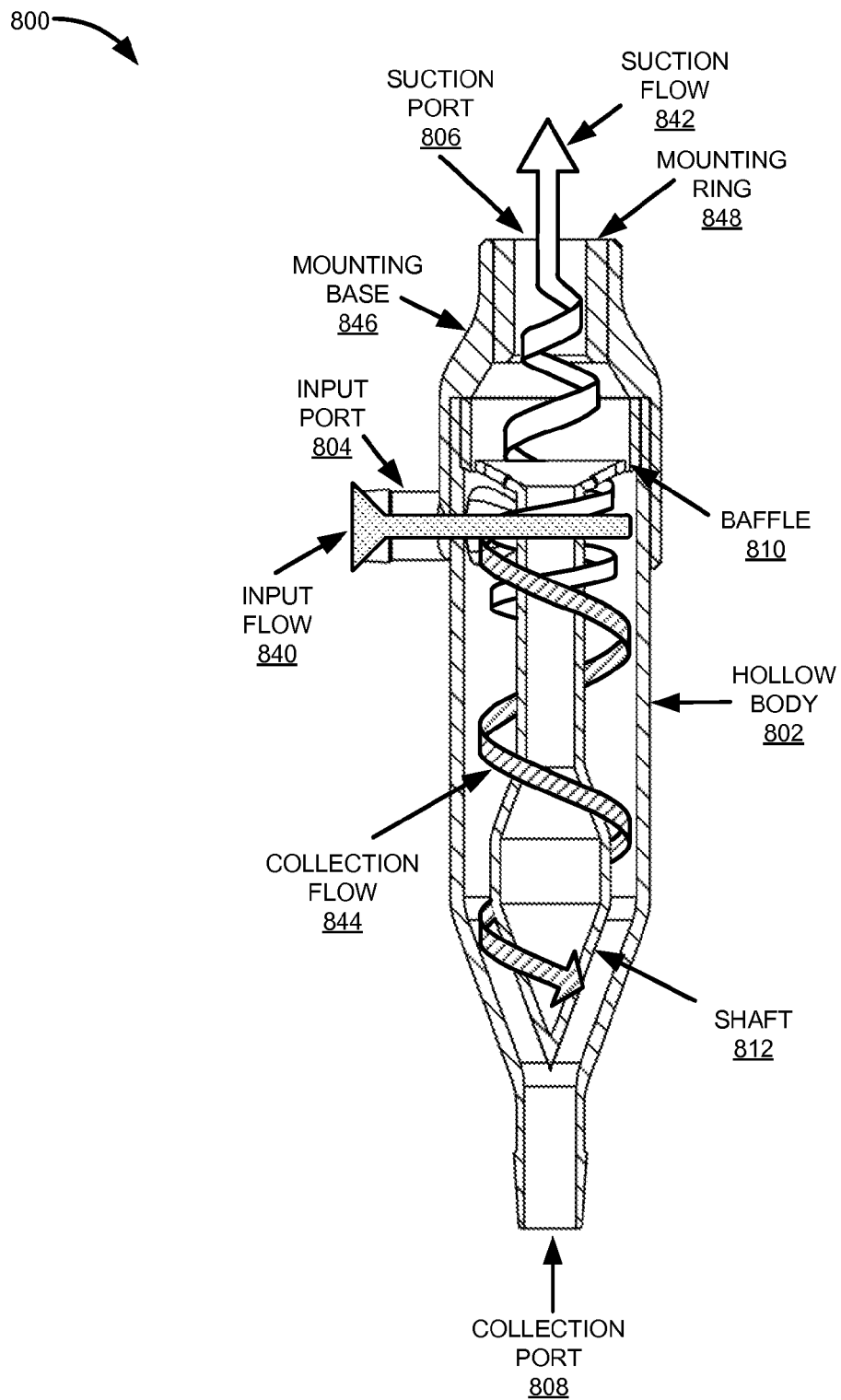
FIG. 8D is a cross-section diagram illustrating the operation of a separator.

FIG. 8D is a cross-section diagram illustrating the operation of separator 800. Separator 800 includes body 802, input port 804, suction port 806, collection port 808, baffle 810, vortex element 812, mounting base 846 and mounting ring 848. The elements in FIG. 8D have been previously described.

In operation, a suction supply is coupled to suction port 806. Suction port 806 is configured to transfer suction from a suction source to input port 804. Suction from a suction source induces input flow 840 to enter input port 804. Baffle 810 includes passageways 850 configured to allow at least gasses included in input flow 840 to exit separator 800 via suction port 806. Baffle 810 includes a solid surface immediately proximal to input port 804 forcing input flow 840 to traverse at least a first portion of the interior of body 802. Vortex element 812 forms an annular opening between vortex element 812 and the interior cavity of body 802. A combination of cyclonic flow generated by separator 800 and gravity cause collection flow 844 to separate out of input flow 840. Collection flow 844 may include at least liquids and solids separated from input flow 840. Collection flow 844 is expelled out collection port 808. Separator 800 is configured to separate suction flow 842 from input flow 840. Suction flow 842 is pulled out suction port 806 by a suction source.

FIG. 9A is an exploded-view diagram illustrating separator 900. Separator 900 is an example of separator 100, separator 202, separator 402, separator 422 and separator 602; however, separator 900 may include alternative configurations and methods of operation.

In some embodiments, separator 900 includes body 902, input port 904, suction port 906, collection port 908, baffle 910, vortex element 912, mounting base 946 and mounting ring 948.

Body 902 includes a cylindrical wall defining a cylindrical cavity. The cylindrical wall includes a first cylindrical cavity end and a second cylindrical cavity end. Body 902 also forms a conical cavity. The conical cavity has a wide end and a narrow end. The wide end is mated to the second cylindrical cavity end of body 902. In some embodiments, body 902 is configured to operate with the first cylindrical cavity end up. Body 902 is configured to allow gravity to pull at least liquid and solids separated from a flow of matter out collection port 908, while gasses separated from the flow of matter are pulled by suction out of suction port 906.

Input port 904 is configured to receive a flow of matter. The flow of matter may be induced into separator 900 via suction port 906 by a suction or vacuum source. Input port 904 is configured to direct a flow of matter along the cylindrical cavity wall of body 902. By directing the flow of matter along the cylindrical cavity wall, liquids and gasses may cling to the wall of the cavity due to the effects of centripetal forces. Input port 904 is integral to body 902. Input port 904 is disposed in the cylindrical cavity wall. Input port 904 is located off-axis from an axis defined by the longitudinal center of the cylindrical cavity.

Suction port 906 is configured to couple to a suction source. In certain embodiments, the suction source may include a vacuum pump, aspirator, and/or a positive pressure operated suction source—such as suction sources that take advantage of Venturi or Coanda effect. Suction from a suction source is transferred from suction port 906 to input port 904. Input port 904 is configured to receive a flow of matter. The flow of matter is pulled into input port 904 by the pressure difference between the ambient air pressure the lower pressure provided by the suction source. The flow of matter may include liquids, solids, and gasses, including combinations thereof in varying ratios. Suction port 906 is disposed near the first cylindrical cavity end. Suction port 906 provides suction received from a suction source for operating separator 900. In some embodiments, suction port 906 may include fittings configured to attach tubing. For example, barbed or quick-disconnect type fittings may be used to couple tubing to suction port 906. The tubing may be used to couple suction port 906 to a suction source or to an input port 904 of another separator.

Collection port 908 is configured to expel a collection flow. The collection flow may comprise at least liquids and solids. Collection port 908 is disposed at the narrow end of the conical cavity of body 902. In an embodiment, collection port 908 may be configured to couple to a collection canister. A collection canister may be used to measure the matter collected from separator 900. A collection canister may also be used for the safe collection, transportation and disposal of waste received from separator 900. In some embodiments, collection port 908 may be coupled to tubing or piping to direct matter to a waste drain. In some embodiments, collection port 908 may include a mounting ring 948 configured to form a seal between collection port 908 to tubing or a collection canister.

Baffle 910 is configured to prevent liquids or solids in the flow from being pulled directly from input port 904 to suction port 906 without traversing at least a first portion of a circumference of the cylindrical wall of separator body 902. Baffle 910 is disposed between input port 904 and suction port 906. Baffle 910 includes passageways 950 configured to allow at least gasses in a flow of matter to separate from liquids and solids that maybe included in the flow. Gasses may be pulled through baffle 910 and out suction port 906. Baffle 910 includes a solid surface located proximal to input port 904 configured to direct the flow to traverse at least a first portion of a circumference of the cylindrical wall of body 902. The solid surface included in baffle 910 may prevent liquids and solids in the flow from being pulled directly from input port 904 to suction port 906 by allowing time for gravity to act on the liquids and solids before they reach an opening in baffle 910. By allowing time for gravity to act on the liquids and solids as they traverse the solid surface of baffle 910, the liquids and solids can descend towards collection port 908 and thereby not be suctioned out of the suction port 906.

Vortex element 912 is configured to form an annular cavity between vortex element 912 and body 902. Vortex element 912 is configured to generate a vortex flow within body 902. The vortex flow and gravity may cause liquids and solids in a flow of matter received at input port 904 to separate from gasses. Liquids and gases may be expelled out collection port 908. Vortex element 912 includes a cylindrical central member disposed within the generally cylindrical cavity of body 902. Vortex element 912 includes a tapered section disposed near the conical cavity of body 902. Vortex element 912 includes a plurality of cylindrical sections having different diameters. The plurality of cylindrical sections includes a first section that defines a first portion of the annular cavity and a second section that defines a second portion of the annular cavity. Baffle 910 is integral to vortex element 912.

Mounting base 946 is configured to allow separator 900 to be assembled. Mounting base 946 is configured to couple to body 902. Mounting base 946 is configured to couple to mounting ring 948.

Mounting ring 948 is configured to operate as a seal for suction port 906. Mounting ring 948 may be made from a flexible material that forms a seal between separator 900 and a coupling to a suction source.

FIG. 9B is a diagram illustrating vortex element 912. Separator 900 includes vortex element 912. Vortex element 912 is configured to form an annular cavity between vortex element 912 and body 902. Vortex element 912 is configured to generate a vortex flow within body 902. The vortex flow and gravity may cause liquids and solids in a flow of matter received at input port 904 to separate from gasses. Liquids and gases may be expelled out collection port 908. Vortex element 912 includes a cylindrical central member disposed within the generally cylindrical cavity of body 902. Vortex element 912 includes a tapered section disposed near the conical cavity of body 902. Vortex element 912 includes a plurality of cylindrical sections having different diameters. The plurality of cylindrical sections includes a first section that defines a first portion of the annular cavity and a second section that defines a second portion of the annular cavity. Baffle 910 is integral to vortex element 912.

Vortex element 912 includes baffle 910. Baffle 910 is configured to prevent liquids or solids in the flow from being pulled directly from input port 904 to suction port 906 without traversing at least a first portion of a circumference of the cylindrical wall of separator body 902. Baffle 910 is disposed between input port 904 and suction port 906. Baffle 910 includes passageways 950 configured to allow at least gasses in a flow of matter to separate from liquids and solids that maybe included in the flow. Gasses may be pulled through baffle 910 and out suction port 906. Baffle 910 includes a solid surface located proximal to input port 904 configured to direct the flow to traverse at least a first portion of a circumference of the cylindrical wall of body 902. The solid surface included in baffle 910 may prevent liquids and solids in the flow from being pulled directly from input port 904 to suction port 906 by allowing time for gravity to act on the liquids and solids before they reach an opening in baffle 910. By allowing time for gravity to act on the liquids and solids as they traverse the solid surface of baffle 910, the liquids and solids can descend towards collection port 908 and thereby not be suctioned out of the suction port 906.

FIG. 9C is a top-view diagram illustrating the operation of separator 900. In operation, a suction source coupled to suction port 906 induces input flow 940 within separator 900. Input flow 940 enters separator 900 through input port 904. Baffle 910 includes passageways 950 configured to allow at least gasses to exit separator 900 via suction port 906. Baffle 910 does not include passageways 950 immediately proximal to input port 904 forcing input flow 940 to traverse at least a first portion of a circumference of the interior of body 902.

Figure 9D:
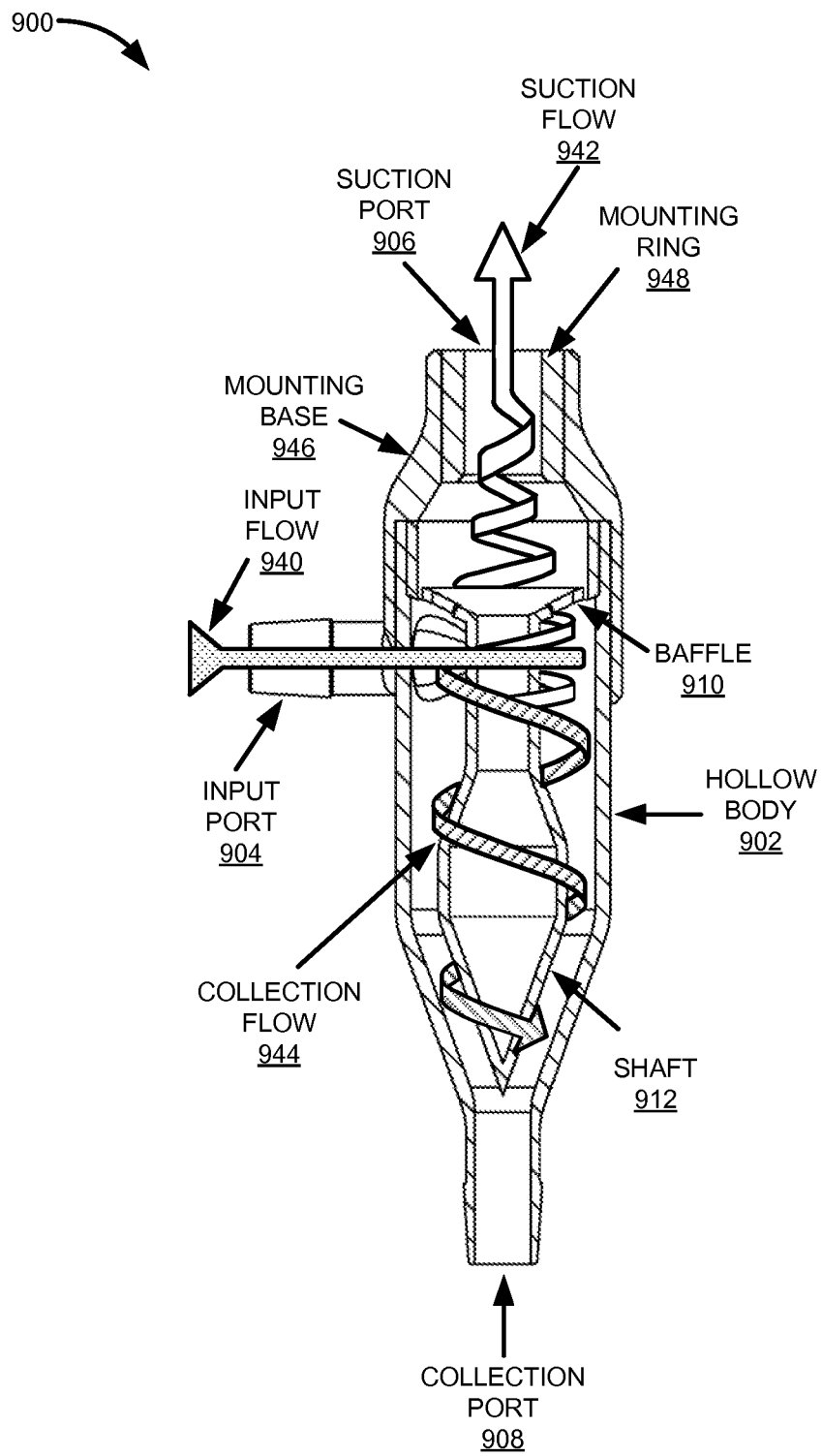
FIG. 9D is a cross-section diagram illustrating the operation of a separator.

FIG. 9D is a cross-section diagram illustrating the operation of separator 900. Separator 900 includes body 902, input port 904, suction port 906, collection port 908, baffle 910, vortex element 912, mounting base 946 and mounting ring 948. The elements in FIG. 9D have been previously described.

In operation, a suction supply is coupled to suction port 906. Suction port 906 is configured to transfer suction from a suction source to input port 904. Suction from a suction source induces input flow 940 to enter input port 904. Baffle 910 includes passageways 950 configured to allow at least gasses included in input flow 940 to exit separator 900 via suction port 906. Baffle 910 does not include passageways 950 immediately proximal to input port 904 forcing input flow 940 to traverse at least a first portion of the interior of body 902. Vortex element 912 forms an annular opening between vortex element 912 and the interior cavity of body 902. A combination of cyclonic flow generated by separator 900 and gravity cause collection flow 944 to separate out of input flow 940. Collection flow 944 may include at least liquids and solids separated from input flow 940. Collection flow 944 is expelled out collection port 908. Separator 900 is configured to separate suction flow 942 from input flow 940. Suction flow 942 is pulled out suction port 906 by a suction source.

Figure 10A:
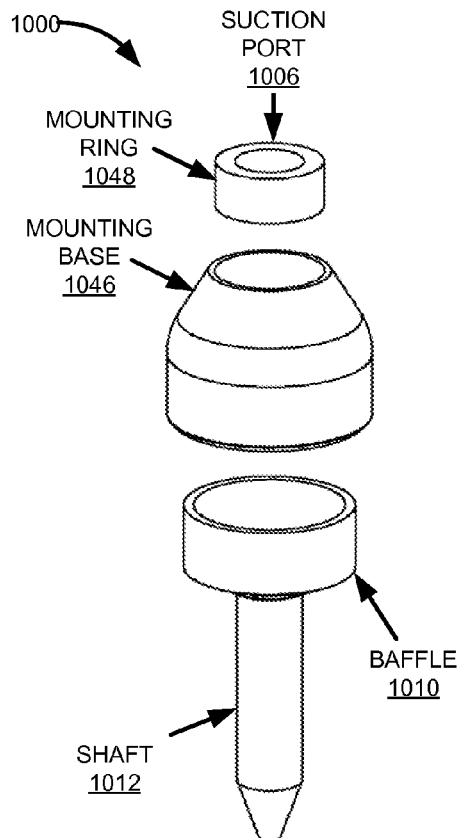
FIG. 10A is an exploded-view diagram illustrating a separator.

FIG. 10A is an exploded-view diagram illustrating separator 1000. Separator 1000 is an example of separator 100, separator 202, separator 402, separator 422 and separator 602; however, separator 1000 may include alternative configurations and methods of operation.

In some embodiments, separator 1000 includes body 1002, input port 1004, suction port 1006, collection port 1008, baffle 1010, vortex element 1012, mounting base 1046 and mounting ring 1048.

Body 1002 includes a cylindrical wall defining a cylindrical cavity. The cylindrical wall includes a first cylindrical cavity end and a second cylindrical cavity end. Body 1002 also forms a conical cavity. The conical cavity has a wide end and a narrow end. The wide end is mated to the second cylindrical cavity end of body 1002. In some embodiments, body 1002 is configured to operate with the first cylindrical cavity end up. Body 1002 is configured to allow gravity to pull at least liquid and solids separated from a flow of matter out collection port 1008, while gasses separated from the flow of matter are pulled by suction out of suction port 1006.

Input port 1004 is configured to receive a flow of matter. The flow of matter may be induced into separator 1000 via suction port 1006 by a suction or vacuum source. Input port 1004 is configured to direct a flow of matter along the cylindrical cavity wall. By directing the flow of matter along the cylindrical cavity wall, liquids and gasses may cling to the wall of the cavity due to the effects of centripetal forces. Input port 1004 is integral to body 1002. Input port 1004 is disposed in the cylindrical cavity wall. Input port 1004 is located off-axis from an axis defined by the longitudinal center of the cylindrical cavity.

Suction port 1006 is configured to couple to a suction source. In certain embodiments, the suction source may include a vacuum pump, aspirator, and/or a positive pressure operated suction source—such as suction sources that take advantage of Venturi or Coanda effect. Suction from a suction source is transferred from suction port 1006 to input port 1004. Input port 1004 is configured to receive a flow of matter. The flow of matter is pulled into input port 1004 by the pressure difference between the ambient air pressure the lower pressure provided by the suction source. The flow of matter may include liquids, solids, and gasses, including combinations thereof in varying ratios. Suction port 1406 is disposed near the first cylindrical cavity end. Suction port 1006 provides suction received from a suction source for operating separator 1000. In some embodiments, suction port 1006 may include fittings configured to attach tubing. For example, barbed or quick-disconnect type fittings may be used to couple tubing to suction port 1006. The tubing may be used to couple suction port 1406 to a suction source or to an input port 1004 of another separator system.

Collection port 1008 is configured to expel a collection flow. The collection flow may comprise at least liquids and solids. Collection port 1008 is disposed at the narrow end of the conical cavity of body 1002. In an embodiment, collection port 1008 may be configured to couple to a collection canister. A collection canister may be used to measure the matter collected from separator 1000. A collection canister may also be used for the safe collection, transportation and disposal of waste received from separator 1000. In some embodiments, collection port 1008 may be coupled to tubing or piping to direct matter to a waste drain. In some embodiments, collection port 1008 may include mounting ring 1048 configured to form a seal between collection port 1008 to tubing or a collection canister.

Baffle 1010 is configured to prevent liquids or solids in the flow from being pulled directly from input port 1004 to suction port 1006 without traversing at least a first portion of a circumference of the cylindrical wall of separator body 1002. Baffle 1010 is disposed between input port 1004 and suction port 1006. Baffle 1010 includes passageways 1050 configured to allow at least gasses in a flow of matter to separate from liquids and solids that maybe included in the flow. Gasses may be pulled through baffle 1010 and out suction port 1006. Baffle 1010 includes a solid surface located proximal to input port 1004 configured to direct the flow to traverse at least a first portion of a circumference of the cylindrical wall of body 1002. The solid surface included in baffle 1010 may to prevent liquids and solids in the flow from being pulled directly from input port 1004 to suction port 1006 by allowing time for gravity to act on the liquids and solids before they reach an opening in baffle 1010. By allowing time for gravity to act on the liquids and solids as they traverse the solid surface of baffle 1010, the liquids and solids can descend towards collection port 1008 and thereby not be suctioned out of the suction port 1006. Baffle 1010 is integral to vortex element 1012.

Vortex element 1012 is configured to form an annular cavity between vortex element 1012 and body 1002. Vortex element 1012 is configured to generate a vortex flow within body 1002. The vortex flow and gravity may cause liquids and solids in a flow of matter received at input port 1004 to separate from gasses. Liquids and gases may be expelled out collection port 1008. Vortex element 1012 includes a cylindrical central member disposed within the generally cylindrical cavity of body 1002. Vortex element 1012 includes a tapered section disposed near the conical cavity of body 1002. Vortex element 1012 is integral to baffle 1010.

Mounting base 1046 is configured to allow separator 1000 to be assembled. Mounting base 1046 is configured to couple to body 1002. Mounting base 1046 is configured to couple to mounting ring 1048.

Mounting ring 1048 is configured to operate as a seal for suction port 1006. Mounting ring 1048 may be made from a flexible material that forms a seal between separator 1000 and a coupling to a suction source.

Figure 10B:
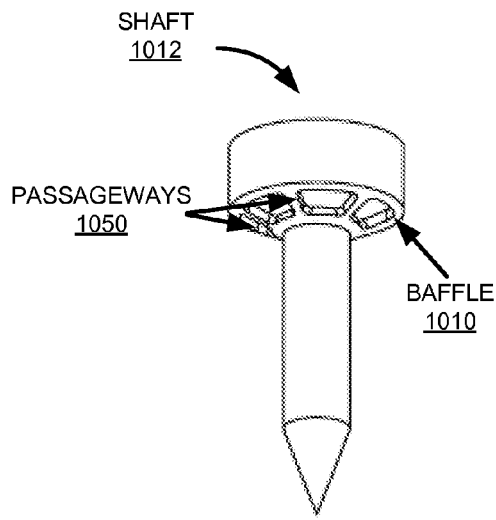
FIG. 10B is a diagram illustrating a shaft (such as a vortex element).

FIG. 10B is a diagram illustrating vortex element 1012. Vortex element 1012 is configured to form an annular cavity between vortex element 1012 and body 1002. Vortex element 1012 is configured to generate a vortex flow within body 1002. The vortex flow and gravity may cause liquids and solids in a flow of matter received at input port 1004 to separate from gasses. Liquids and gases may be expelled out collection port 1008. Vortex element 1012 includes a cylindrical central member disposed within the generally cylindrical cavity of body 1002. Vortex element 1012 includes a tapered section disposed near the conical cavity of body 1002. Baffle 1010 is integral to vortex element 1012.

Figure 10C:
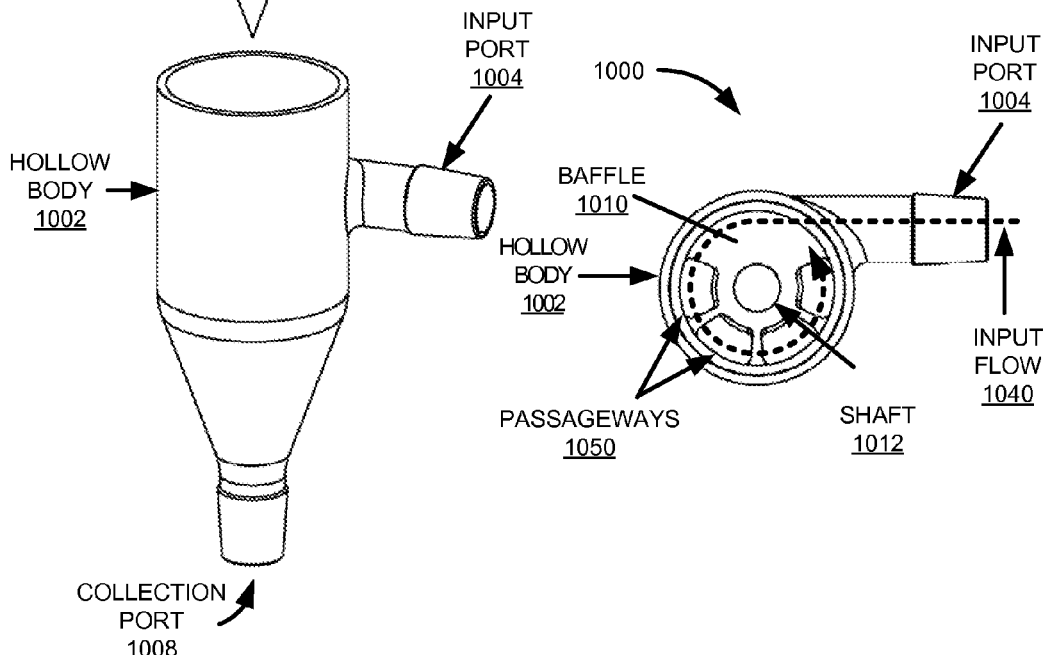
FIG. 10C is a top-view diagram illustrating the operation of a separator.

FIG. 10C is a top-view diagram illustrating the operation of separator 1000. In operation, a suction source coupled to suction port 1006 induces input flow 1040 within separator 1000. Flow 1040 enters separator 1000 through input port 1004. Baffle 1010 includes passageways 1050 configured to allow at least gasses to exit separator 1000 via suction port 1006. Baffle 1010 does not include passageways 1050 immediately proximal to input port 1004 forcing input flow 1040 to traverse at least a first portion of a circumference of the interior of body 1002.

Figure 10D:
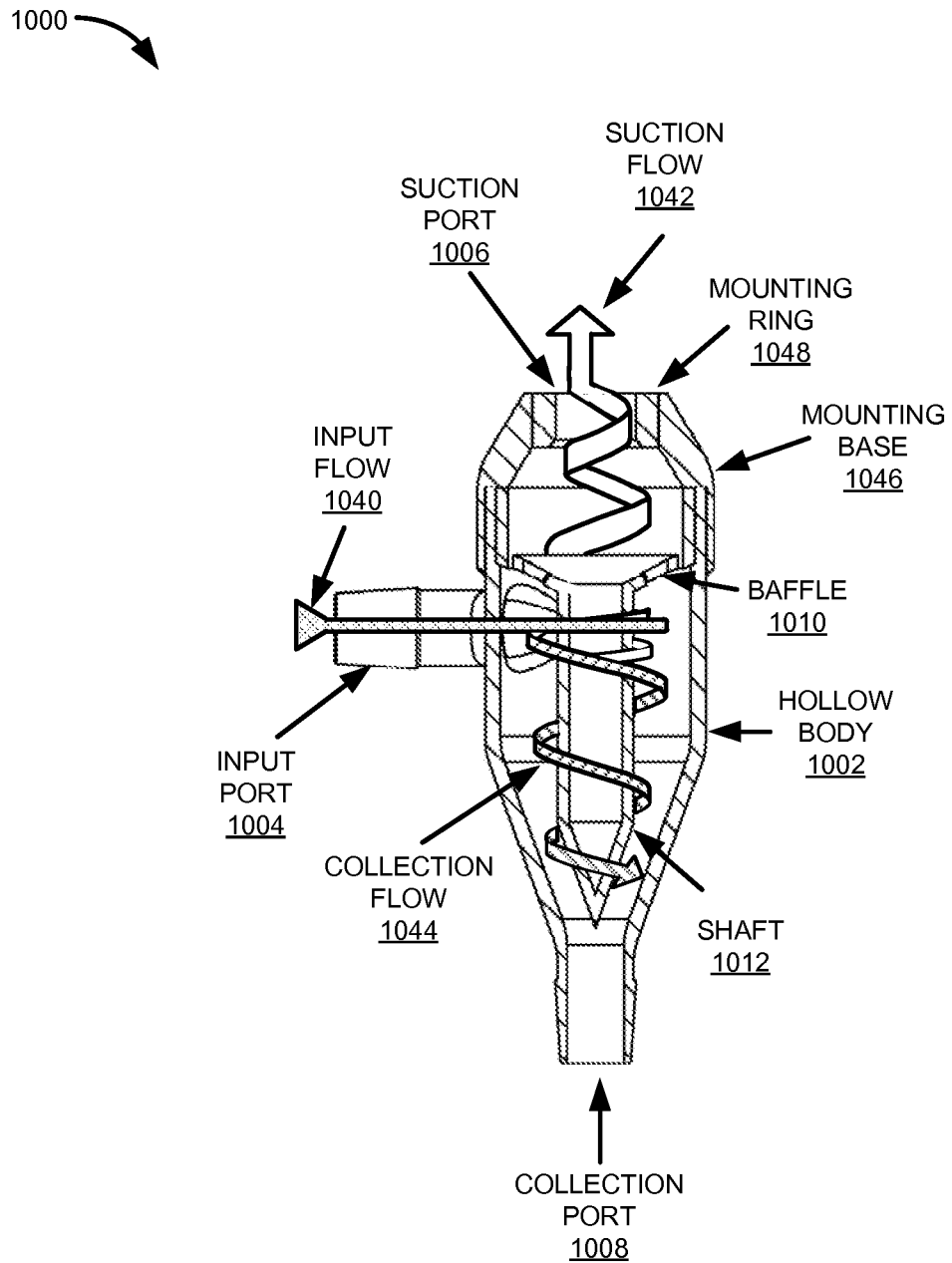
FIG. 10D is a cross-section diagram illustrating the operation of a separator.

FIG. 10D is a cross-section diagram illustrating the operation of separator 1000. Separator 1000 includes body 1002, input port 1004, suction port 1006, collection port 1008, baffle 1010, vortex element 1012, mounting base 1046 and mounting ring 1048. The elements in FIG. 10D have been previously described. FIG. 10D is included for further reference.

In operation, a suction supply is coupled to suction port 1006. Suction port 1006 is configured to transfer suction from a suction source to input port 1004. Suction from a suction source induces input flow 1040 to enter input port 1004. Baffle 1010 includes passageways 1050 configured to allow at least gasses included in input flow 1040 to exit separator 1000 via suction port 1006. Baffle 1010 does not include passageways 1050 immediately proximal to input port 1004 forcing input flow 1040 to traverse at least a first portion of the interior of body 1002. Vortex element 1012 forms an annular opening between vortex element 1012 and the interior cavity of body 1002. A combination of cyclonic flow generated by separator 1000 and gravity cause collection flow 1044 to separate out of input flow 1040. Collection flow 1044 may include at least liquids and solids separated from input flow 1040. Collection flow 1044 is expelled out collection port 1008. Separator 1000 is configured to separate suction flow 1042 from input flow 1040. Suction flow 1042 is pulled out suction port 1006 by a suction source.

FIG. 11A is an exploded-view diagram illustrating separator 1100. Separator 1100 is an example of separator 100, separator 202, separator 402, separator 422 and separator 602; however, separator 1100 may include alternative configurations and methods of operation.

In some embodiments, separator 1100 includes body 1102, input port 1104, suction port 1106, collection port 1108, baffle 1110 and vortex element 1112.

Body 1102 includes a cylindrical wall defining a cylindrical cavity. The cylindrical wall includes a first cylindrical cavity end and a second cylindrical cavity end. Body 1102 also forms a conical cavity. The conical cavity has a wide end and a narrow end. The wide end is mated to the second cylindrical cavity end of body 1102. In some embodiments, body 1102 is configured to operate with the first cylindrical cavity end up. Body 1102 is configured to allow gravity to pull at least liquid and solids separated from a flow of matter out collection port 1108, while gasses separated from the flow of matter are pulled by suction out of suction port 1106.

Input port 1104 is integral to body 1102. Input port 1104 is disposed in the cylindrical cavity wall. Input port 1104 is located off-axis from an axis defined by the longitudinal center of the cylindrical cavity. Input port 1104 is configured to receive a flow of matter. The flow of matter may be induced into separator 1100 via suction port 1106 by a suction or vacuum source. Input port 1104 is configured to direct a flow of matter along the cylindrical cavity wall. By directing the flow of matter along the cylindrical cavity wall, liquids and gasses may cling to the wall of the cavity due to the effects of centripetal forces.

Collection port 1108 is disposed at the narrow end of the conical cavity of body 1102. Collection port 1108 is configured to expel at least liquids and solids. In an embodiment, collection port 1108 may be configured to couple to a collection canister. A collection canister may be used to measure the matter collected from separator 1100. A collection canister may also be used for the safe collection, transportation and disposal of waste received from separator 1100. In some embodiments, collection port 1108 may be coupled to tubing or piping to direct matter to a waste drain. In some embodiments, collection port 1108 may include a mounting ring configured to form a seal between collection port 1108 to tubing or a collection canister.

Baffle 1110 is disposed between input port 1104 and suction port 1106. Baffle 1110 is configured to prevent liquids or solids in the flow from being pulled directly from input port 1104 to suction port 1106 without traversing at least a first portion of a circumference of the cylindrical wall of separator body 1102. Baffle 1110 includes a solid surface located proximal to input port 1104. The solid surface may be used to prevent liquids and solids in the flow from being pulled directly from input port 1104 to suction port 1106 by allowing time for gravity to act on the liquids and solids before they reach an opening in baffle 1110. By allowing time for gravity to act on the liquids and solids as they traverse the solid surface of baffle 1110, the liquids and solids can descend towards collection port 1308 and thereby not be suctioned out of the suction port 1106. Baffle 1110 is integral to vortex element 1112.

Vortex element 1112 includes a tapered cylindrical central member disposed within the generally cylindrical cavity of body 1102. Vortex element 1112 is configured to form an annular cavity between vortex element 1112 and body 1102. Vortex element 1112 is configured to generate a vortex flow within body 1102. The vortex flow and gravity may cause liquids and solids in a flow of matter received at input port 1104 to separate from gasses. Liquids and solids may be expelled out collection port 1108. Vortex element 1112 includes a lumen disposed within the cylindrical central member configured to allow at least gasses to pass through vortex element 1112 to suction port 1106. Baffle 1110 is integral to vortex element 1112.

FIG. 11B is a top-view diagram illustrating the operation of separator 1100. In operation, a suction source coupled to suction port 1106 induces input flow 1140 within separator 1100. Input flow 1140 enters separator 1100 through input port 1104. Baffle 1110 includes suction port 1106 configured to allow at least gasses to exit separator 1100. Baffle 1110 is configured to force input flow 1140 to traverse at least a first portion of a circumference of the interior of body 1102 before exiting suction port 1106.

Figure 11C:
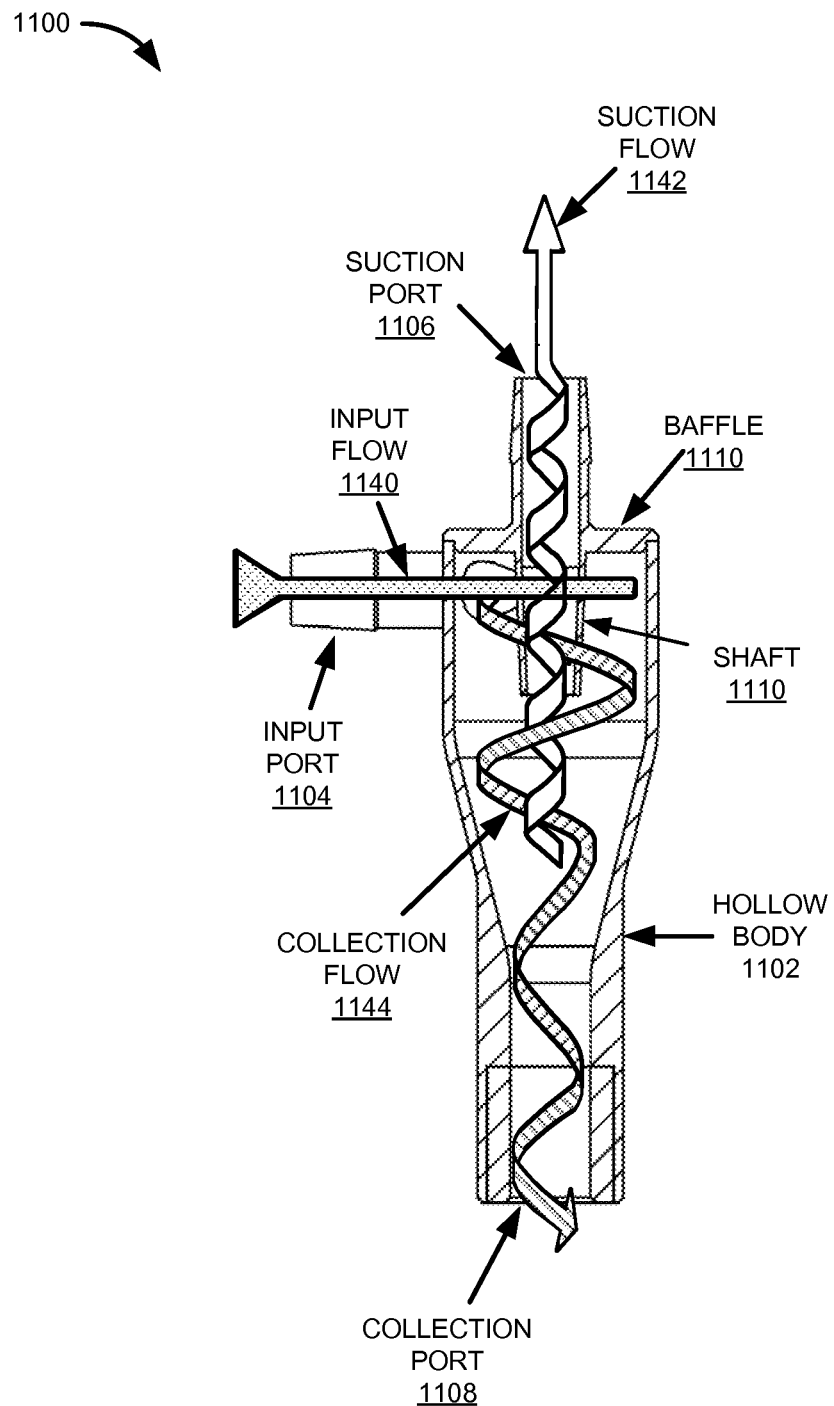
FIG. 11C is a cross-section diagram illustrating the operation of a separator.

FIG. 11C is a cross-section diagram illustrating the operation of separator 1100. Separator 1100 includes body 1102, input port 1104, suction port 1106, collection port 1108, baffle 1110 and vortex element 1112.

In operation, Separator 1100 is configured to separate suction flow 1142 from input flow 1140. A suction source is coupled to suction port 1106. Suction port 1106 is configured to transfer suction from a suction source to input port 1104. Suction from a suction source induces input flow 1140 to enter input port 1104. Baffle 1110 is configured to force input flow 1140 to traverse at least a first portion of the interior of body 1102 before passing out suction port 1106. Vortex element 1112 is configured to allow suction flow 11142 separated from input flow 1140 to exit separator 1100 via suction port 1106. Vortex element 1112 forms an annular opening between vortex element 1112 and the interior cavity of body 1102. A combination of cyclonic flow generated by separator 1100 and gravity may cause collection flow 1144 to separate from input flow 1140. Collection flow 1144 may include at least liquids and solids separated from input flow 1140. Collection flow 1144 is expelled out collection port 1108. Suction flow 1142 is pulled out suction port 1106 by a suction source.

Figure 12:
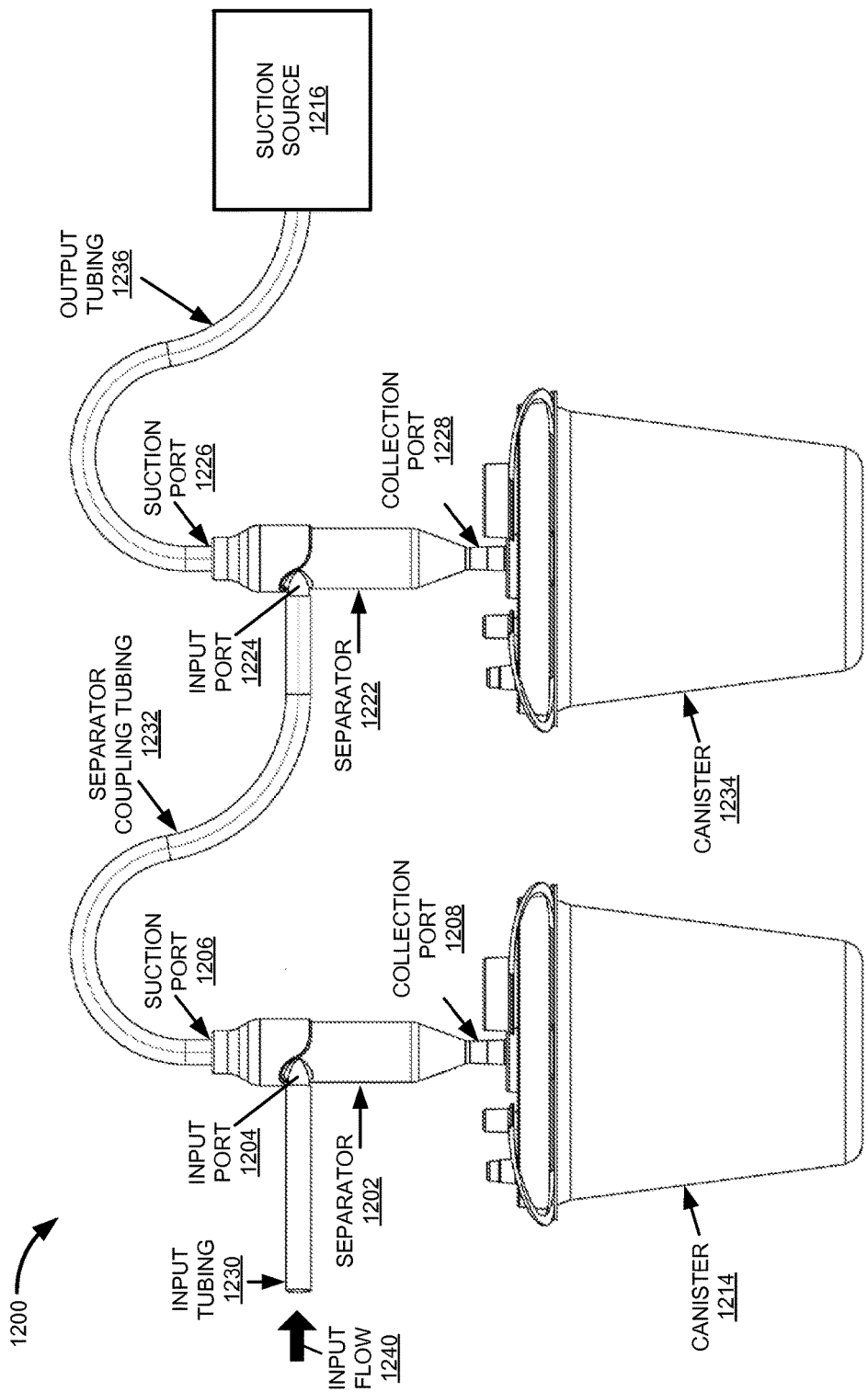
FIG. 12 is a diagram illustrating a separator system.

FIG. 12 is a block diagram illustrating a separator system 1200. Separator 1202 and separator 1222 are examples separator 100, separator 202, separator 402, separator 422 and separator 602, separator 800, separator 900, separator 1000, and separator 1100; however, separator system 1200 may include alternative configurations and methods of operation.

In some embodiments, separator system 1200 includes separator 1202, canister 1214, separator 1222, input tubing 1230, separator coupling tubing 1232, canister 1234 and output tubing 1236.

In some embodiments, separator 1202 includes input port 1204, suction port 1206, collection port 1208, baffle 1210 and vortex element 1212.

Separator 1202 includes a body with a cylindrical cavity having a cylindrical cavity wall, a first cylindrical cavity end, and a second cylindrical cavity end. In some embodiments, separator 1202 may be configured to operate with the first cylindrical end up. The body may include a conical cavity. The conical cavity may include a wide end and a narrow end. The wide end may be coupled to the second cylindrical cavity end.

In some embodiments, input port 1204 may be integral to a body included as part of separator 1202. Input port 1204 may integral to separator 1202. Input port 1204 maybe located off-axis from an axis defined by the longitudinal center of separator 1202. Input port 1204 is configured to direct input flow 1240 of matter along the interior of separator 1202. Input port 1204 is configured to receive input flow 1240. Input flow 1240 may be induced into separator 1202 via suction source 1216. Suction port 1206 is configured to couple to suction source 1216. As illustrated in FIG. 12, suction port 1206 may be configured to receive suction from suction source 1216 after the suction has passed through another device, such as separator 1222. In some embodiments, suction source 1216 may include a vacuum pump, aspirator, and/or a positive pressure operated suction device that takes advantage of the Coanda effect. In some embodiments, input port 1204 may include fittings configured to attach tubing. For example, barbed or quick-disconnect type fittings may be used to couple tubing to input port 1204.

Suction port 1206 is disposed near a first end of separator 1202. Suction port 1206 is configured to couple to suction source 1216 or another separator, such as separator 1222. Suction port 1206 provides suction received from suction source 1216 to operate separator 1202. In some embodiments, suction port 1206 may include fittings configured to attach tubing. For example, barbed or quick-disconnect type fittings may be used to couple tubing to suction port 1206. The tubing may be used to couple suction port 1206 to suction source 1216 or to input port 1224 of separator 1222.

Collection port 1208 may be disposed at a second end of separator 1202. Collection port 1208 is configured to expel at least liquids and solids. Collection port 1208 is configured to couple to canister 1214. Canister 1214 may be used to measure matter collected from separator 1202. Canister 1214 may also be used for the safe collection and disposal of waste received from separator 1202. In some embodiments, collection port 1208 may be coupled to tubing or piping to direct matter to a waste drain. In some embodiments, collection port 1208 may include a mounting ring configured to form a seal between collection port 1208 and canister 1214.

Canister 1214 is configured to receive a collection flow from separator 1202. The collection flow may include liquids and solids separated from input flow 1240 received at input port 1204. The collection flow may include surgical byproducts. Canister 1214 may be used to measure the amount of liquids and/or solids separated from input flow 1240 received at input port 1204. Canister 1214 may be configured to permit the safe collection and disposal of waste. In some embodiments, canister 1214 may include a valve configured to activate when canister 1214 is filled to a pre-determined volume. The valve may be used to prevent waste from leaving canister 1214 during transportation. In some embodiments, canister 1214 may include a commercially available collection canister.

Separator system 1200 includes separator 1222 and collection canister 1234. Separator 1222 may include similar configurations and methods of operation as separator 1202. For the sake of brevity, separator 1222 will not be described further. Likewise collection canister 1234 may include similar configurations and methods of operation as canister 1214. For the sake of brevity, collection canister 1234 will not be described further.

Suction source 1216 may be any device configured to generate a pressure below an ambient air pressure. Suction source 1216 may include a vacuum pump, aspirator or Coanda based positive pressure operated suction device. In some embodiments, suction source 1216 may be configured to take advantage of the Coanda or Venturi effect.

In operation, suction source 1216 supplies a suction flow to suction port 1226 via output tubing 1236. Separator 1222 is configured to transfer the suction flow to separator 1202. Suction flow 1242 creates a pressure near input port 1204 that is below the ambient air pressure. The ambient air pressure overcomes the pressure of the suction flow thereby inducing input flow 1240 into input port 1204. Input port 1204 is configured to receive input flow 1240. Input flow 1240 may comprise liquids, gasses and solids, including combinations thereof in varying ratios. Input flow 1240 may include surgical byproducts. Separator 1202 creates a cyclonic flow from the suction flow. The cyclonic flow and gravity cause a collection flow to separate from input flow 1240. The collection flow may comprise at least liquids and solids. The collection flow is expelled from collection port 1208. Collection port 1208 is configured to direct the collection flow to collection canister 1214.

Separator 1202 separates a suction flow from a collection flow. In a first mode of operation, the suction flow may comprise primarily gasses separated from input flow 1240. The suction flow is pulled from separator 1202 by suction source 1216. The suction flow is passed from suction port 1206 to input port 1224. Separator 1202 continues to operate in the first mode of operation until a fill volume within collection canister 1214 reaches a predetermined volume.

Separators 1202, 1222 may be configured to pass input flow 1240 from input ports 1204, 1224 to suction ports 1206, 1226 unseparated when collection canisters 1214, 1234 reach predetermined fill volumes. In a second mode of operation, separator 1202 may pass input flow 1240 through suction port 1206 to separator 1222 unseparated.

In operation, suction source 1216 supplies a suction flow from suction source 1216 to suction port 1226. Separator 1222 is configured to pass the suction flow to separator 1202. The suction flow pulls input flow 1240 into input port 1204. Separator 1202 passes input flow 1240 from input port 1204 to suction port 1206 unseparated because a predetermined fill volume within collection canister 1214 has been reached. Input flow 1240 is received by input port 1224. A fill volume in collection canister 1234 has not reached a predetermined fill volume. Separator 1222 separates a collection flow from a suction flow. The collection flow may comprise primarily liquids and solids from input flow 1240. Separator 1222 separates a suction flow from a collection flow. The collection flow is expelled out collection port 1228. Collection port 1228 is coupled to collection canister 1234. Collection canister 1234 is configured to receive a collection flow from collection port 1228. A suction flow is pulled out suction port 1226 by suction source 1216.

Figure 13A:
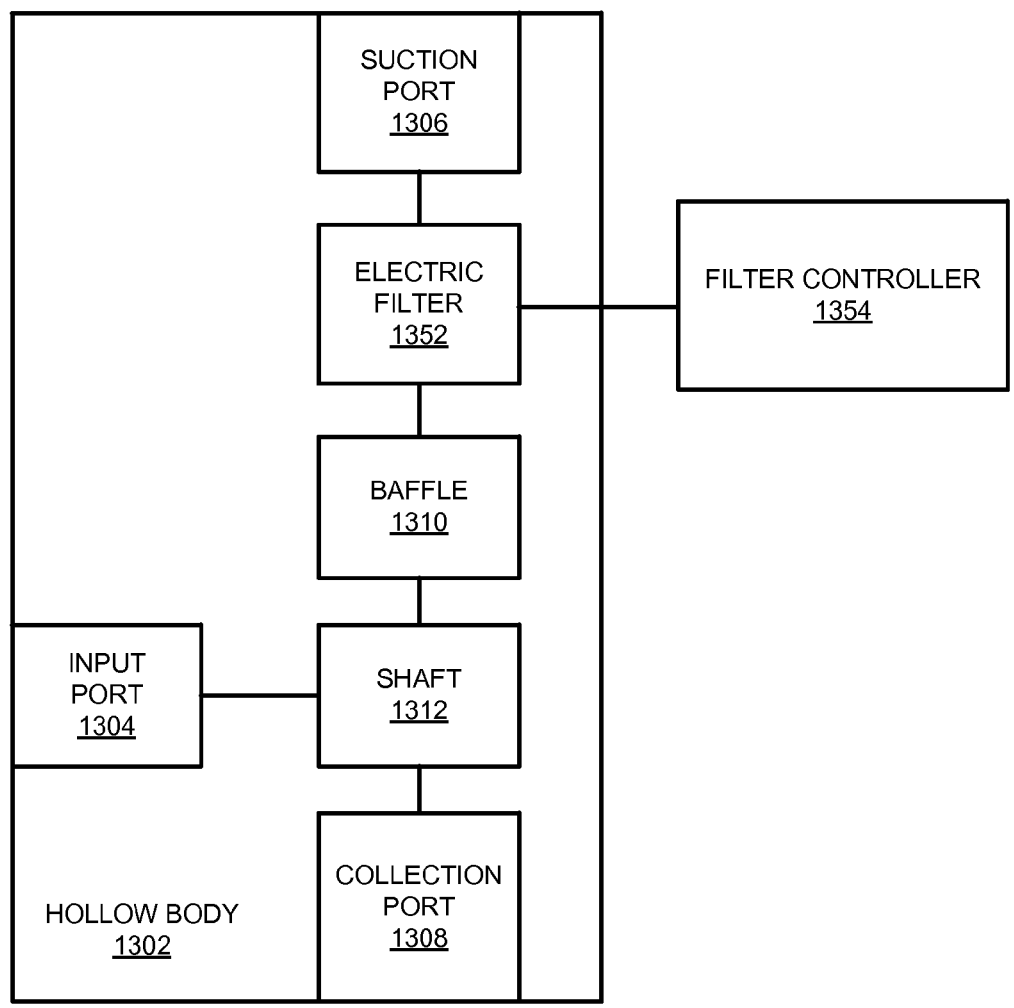
FIG. 13A is a block diagram illustrating a separator with filter.

FIG. 13A is a block diagram illustrating separator with filter 1300. Separator with filter 1300 is an example of separator 100, separator 202, separator 402 and separator 602; however, separator with filter 1300 includes electric filter 1352. In addition, separator with filter 1300 may include alternative configurations and methods of operation than the previously described embodiments.

Separator with filter 1300 includes separator body 1302, input port 1304, suction port 1306, collection port 1308, baffle 1310, vortex element 1312 and electric filter 1352 and filter controller 1354. In operation, separator 1300 is configured to separate liquids, solids and gasses in a flow of matter. Separator 1300 ejects liquids and solids separated from the flow of matter out collection port 1308 while suctioning at least gasses separated from the flow of matter out suction port 1306. Separator 1300 is operated by suction received from a suction source. Separator with filter 1300 is further configured to filter particles from gasses suction from suction port 1306.

Separator with filter 1300 includes separator body 1302. Separator body 1302 includes a cylindrical wall defining a cylindrical cavity. The cylindrical wall includes a first cylindrical cavity end and a second cylindrical cavity end. Separator body 1302 also forms a conical cavity. The conical cavity has a wide end and a narrow end. The wide end is mated to the second cylindrical cavity end of separator body 1302. In some embodiments, separator body 1302 is configured to operate with the first cylindrical cavity end up. Separator body 1302 is configured to allow gravity to pull at least liquid and solids separated from a flow of matter out collection port 1308, while gasses separated from the flow of matter are pulled by suction out of suction port 1306.

Separator with filter 1300 includes input port 1304. Input port 1304 is configured to receive a flow of matter. In some embodiments, input port 1304 may be integral to separator body 1302. Input port 1304 may be disposed in the cylindrical cavity wall. Input port 1304 may be located off-axis from an axis defined by the longitudinal center of the cylindrical cavity. Input port 1304 may be configured to direct a flow of matter along the cylindrical cavity wall. By directing the flow of matter along the cylindrical cavity wall, liquids and gasses may cling to the wall of the cavity due to the effects of centripetal forces. The flow of matter may be induced into separator 1300 by suction received from suction port 1306 by a suction or vacuum source.

Separator with filter 1300 includes suction port 1306. Suction port 1306 is configured to couple to a suction source. In certain embodiments, the suction source may include a vacuum pump, aspirator, and/or a positive pressure operated suction source—such as suction sources that take advantage of Venturi or Coanda effect. Suction from a suction source is transferred from suction port 1306 to input port 1304. Input port 1304 is configured to receive a flow of matter. The flow of matter is pulled into input port 1304 by the pressure difference between the ambient air pressure the lower pressure provided by the suction source. The flow of matter may include liquids, solids, and gasses, including combinations thereof in varying ratios. Suction port 1306 is disposed near the first cylindrical cavity end. Suction port 1306 provides suction received from a suction source for operating separator canister with filter 1300. In some embodiments, suction port 1306 may include fittings configured to attach tubing. For example, barbed or quick-disconnect type fittings may be used to couple tubing to suction port 1306. The tubing may be used to couple suction port 1306 to a suction source or to an input port 1304 of another separator system.

Separator 1300 includes collection port 1308. Collection port 1308 is configured to expel at least liquids and solids. Collection port 1308 is disposed at the narrow end of the conical cavity of separator body 1302. In an embodiment, collection port 1308 may be configured to couple to a collection canister. A collection canister may be used to measure the matter collected from separator 1300. A collection canister may also be used for the safe collection, transportation and disposal of waste received from separator with filter 1300. In some embodiments, collection port 1308 may be coupled to tubing or piping to direct matter to a waste drain. In some embodiments, collection port 1308 may include a mounting ring configured to form a seal between collection port 1308 to tubing or a collection canister.

Separator with filter 1300 includes baffle 1310. Baffle 1310 is disposed between input port 1304 and suction port 1306. Baffle 1310 is configured to prevent liquids or solids in the flow from being pulled directly from input port 1304 to suction port 1306 without traversing at least a first portion of a circumference of the cylindrical wall of separator body 1302. In some embodiments, baffle 1310 may include openings configured to allow at least gasses in a flow of matter to separate from liquids and solids that maybe included in the flow. Gasses may be pulled through baffle 1310 and out suction port 1306. In an embodiment, baffle 1310 may include a solid surface located proximal to input port 1304. The solid surface that may be included in baffle 1310 may be used to prevent liquids and solids in the flow from being pulled directly from input port 1304 to suction port 1306 by allowing time for gravity to act on the liquids and solids before they reach an opening in baffle 1310. By allowing time for gravity to act on the liquids and solids as they traverse the solid surface of baffle 1310, the liquids and solids can descend towards collection port 1308 and thereby not be suctioned out of the suction port 1306.

Separator with filter 1300 includes vortex element 1312. Vortex element 1312 is configured to direct a flow of matter in a cyclonic flow. The cyclonic flow and gravity may cause liquids, solids and gasses included in the flow of matter to separate. Vortex element 1312 includes a cylindrical central member disposed within the cylindrical cavity of separator body 1302. The cylindrical central member forms an annular cavity between vortex element 1312 and separator body 1302. Vortex element 1312 is configured to allow liquids and solids in the flow to pass through the annular cavity before dropping out collection port 1308. In an embodiment, vortex element 1312 may include a tapered section disposed in the conical cavity of separator body 1302. In an embodiment, vortex element 1312 may include a plurality of cylindrical sections having different diameters. The plurality of cylindrical sections may include a first section that defines a first portion of the annular cavity and a second section that defines a second portion of the annular cavity. The tapered and cylindrical sections may be configured to direct the flow within separator body 1302 in a cyclonic flow pattern. In an embodiment, baffle 1310 may be integral to vortex element 1312.

Separator with filter 1300 includes electric filter 1352. Electric filter 1352 is configured to use electrical charge to capture particles that may be included in a flow exiting suction port 1306. Electric filter 1352 may comprise a matrix of conductive elements. In some embodiments, the conductive elements may be iron, steel, copper or some other conductive element. In some embodiments, the matrix may be comprised of stacked screens. In some embodiments, the matrix may be comprised of entwined wire. Electric filter 13552 is coupled to filter controller 1354. Electric filter 1352 is configured to receive power from filter controller 1354.

Separator with filter 1300 includes filter controller 1354. Filter controller 1354 is configured to operate electric filter 1352 in such a manner as to collect particles included in a flow of matter using an electrical charge. Filter controller 1354 is configured to provide electric filter 1352 power at a particular voltage level, current level and possibly frequency. In some embodiments, filter controller 1354 may be configured to provide direct current. In some embodiments, filter controller may include a microcontroller configured to power electric filter 1352.

Figure 13B:
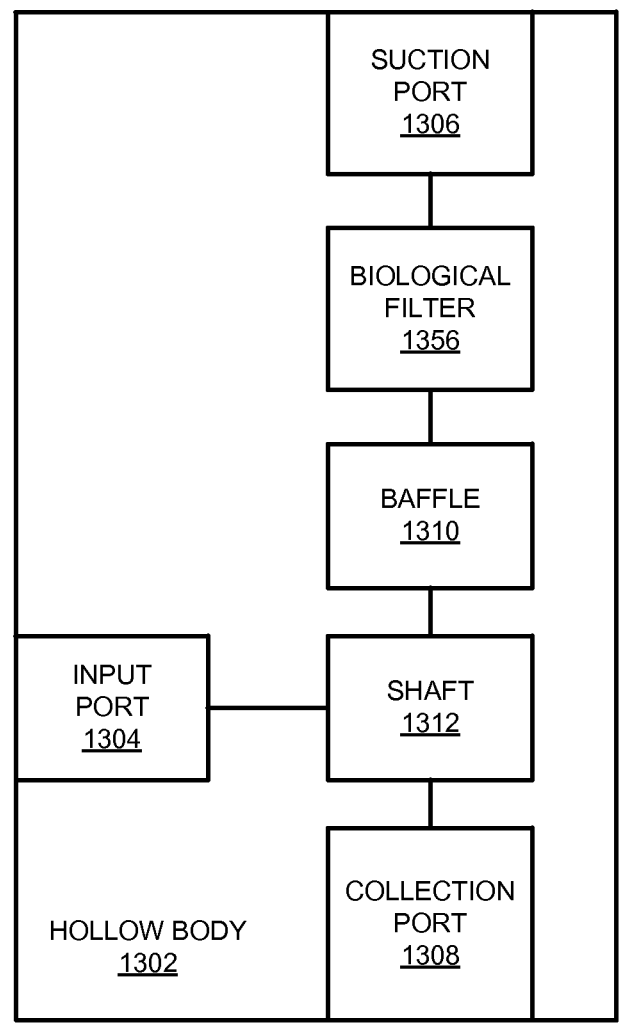
FIG. 13B is a block diagram illustrating a separator with filter.

FIG. 13B is a block diagram illustrating separator with filter 1300. In this embodiment, separator with filter 1300 includes biological filter 1356 rather than electric filter 1352.

Biological filter 1356 is configured to trap biological elements possibly included in a flow to be expelled from suction port 1306. Various embodiments of filter 1352 may be configured to trap specific types of biological elements using different operations.

Biological filter 1356 is disposed within separator body 1302. Biological filter 1356 includes one or more filter inlet ports and one or more filter output ports. The one or more filter inlet ports are configured to receive a flow of matter from baffle 1310. Elements comprising biological filter 1356 are configured to trap biological elements possibly contained in the flow of matter and passes a filtrate to suction port 1306.

Biological filter 1356 may comprise mechanical, biological, chemical or other types of filters including any combination thereof to trap biological elements. Mechanical filtration may include physical barrier or filter media type filters including combinations thereof Filters using a physical barrier or filter media retain biological elements by physically blocking the biological elements from passing through the filter media. Filter media mechanically or physically strains biological elements from the effluent passing through it. Filter media is available in a variety of materials and porosities, which may be selected to limit the size of biological elements they can extract. Combinations of different materials and porosities of filter media may be used to separate specific elements comprising an effluent of the collected matter and the gasses received via input port 11304 out suction port 1306.

Biological filter 1356 may be configured to use living microorganisms, such as bacteria and fungi, to capture and biologically degrade pollutants, harmful chemicals and other undesirable content from an effluent. Biological filtration can be used with gases and liquids. Biological filters comprise a filter media on which beneficial microorganisms grow. Biological filter media can be made from sand, plastic, metals, ceramics and other materials. Materials having a large surface area to volume ratio typically provide the best performance in biological filters.

Biological filter 1356 may be configured to use chemical filtration media to removes dissolved particulates from an effluent via activated carbons, resins, and other adsorbents. Chemical filtration media causes unwanted dissolved matter to adhere to it. Two popular forms of chemical media include activated carbon and resins. Activated carbon has microscopic pores that allow certain organic or inorganic materials to stick to them. Carbon removes many harmful elements from an effluent. Ion exchange resins work by attracting a specific molecule to adhere to them. Resins can be combined with carbon. The resins often strengthen the filtering ability of the carbon. Protein foam skimming or oxidation with ozone may also be used for chemical filtration.

Figure 13C:
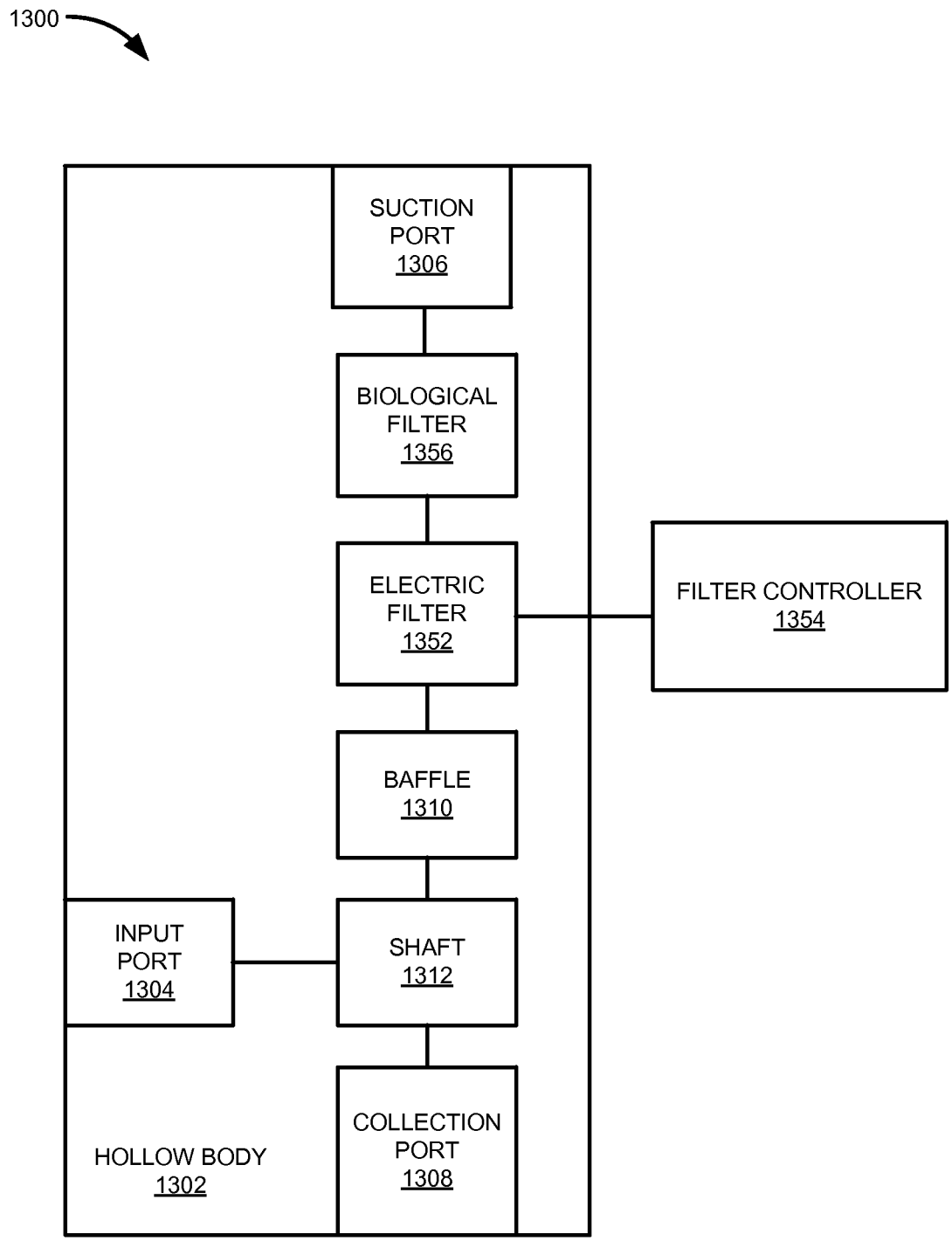
FIG. 13C is a block diagram illustrating a separator with filter.

FIG. 13C is a block diagram illustrating separator with filter 1300. Separator with filter 1300 is an embodiment of separator with filter 1300 which includes electric filter 1352 and biological filter 1356. The elements included in FIG. 13C have been previously described in FIGS. 13A and 13B. For the sake of brevity, these elements will not be discussed further.

The system may comprise one of more filters. In some embodiments, the one or more filters is positioned within a surgical instrument, within a separator, between a surgical instrument and a separator, within a suction source, between a separator and a suction source, within a filtration unit, between a separator and a filtration unit, within a canister, between a separator and a canister, or any combination thereof. In some embodiments, the one or more filters may collect one or more solids. In some embodiments, the one or more filters may sample a portion of a flow of matter than comprises solids. In some embodiments, the one or more filters may substantially remove an entire portion of solids from a flow of matter. In some embodiments, the one or more filters may remove a portion, such as about 60%, 70%, 80% 90%, 95% or more, of solids from a flow of matter. In some embodiments, the one or more filters may separate solids by size. In some embodiments, the one or more filters may remove solids of a particular size from the flow of matter. In some embodiments, the one or more solids collected on the one or more filters are analyzed in a diagnostic laboratory. In some embodiments, the one or more solids is a bacterium, a bacterial fragment, a bacterial particle, a virus, a viral fragment, a viral particle, a cell, a cell fragment, a tissue fragment, a non-biological material such as polymeric fragments or metallic fragments, or any combination thereof In some embodiments, a pore size of the one or more filters is less than about 500, 450, 400, 350, 300, 250, 200, 150, 100, 90, 80, 70, 60, 50, 40, 30, 20, 10, 9, 8, 7, 6, 5, 4, 3, 2, 1, 0.5, 0.25 microns or less. In some embodiments, a pore size of one or more filters is less than about 500 microns. In some embodiments, a pore size of one or more filters is less than about 400 microns. In some embodiments, a pore size of one or more filters is less than about 300 microns. In some embodiments, a pore size of one or more filters is less than about 200 microns. In some embodiments, a pore size of one or more filters is less than about 100 microns. In some embodiments, a pore size of one or more filters is less than about 75 microns. In some embodiments, a pore size of one or more filters is less than about 50 microns. In some embodiments, a pore size of one or more filters is less than about 25 microns. In some embodiments, a pore size of one or more filters is less than about 10 microns. In some embodiments, a pore size of one or more filters is less than about 5 microns. In some embodiments, a pore size of one or more filters is less than about 1 micron. In some embodiments, a pore size of one or more filters is less than about 0.5 micron. In some embodiments, a pore size of one or more filters is less than about 0.25 micron.

The system may comprise one or more charged matrices, such as one or more positively charged matrices, one or more negatively charged matrices, or any combination thereof. The one or more charged matrices are operatively coupled to the surgical instrument, the separator, the suction source, or any combination thereof. The one or more charged matrices are operative coupled to a suction port of the separator. The one or more charged matrices may surround a portion of the suction port or a portion of the tubing operatively coupled to the suction port, such as 25%, 50%, 75%, 90% or more surrounded.

The one or more positively charged matrices is hydrogen, sodium, potassium, lithium, rubidium, cesium, copper, silver, ammonium, calcium, barium, magnesium, zinc, iron, cobalt, manganese, aluminum, or any combination thereof. The one or more positively charged matrices are $Fe^{2+}$ or $Fe^{3+}$ or a combination thereof. The one or more negatively charged matrices is chloride, bromide, iodide, hydroxide, nitrate, nitrite, hydrogencarbonate, hydrogensulphate, sulphate, sulphite, sulphide, oxide, carbonate, copper, phosphate, or any combination thereof.

Figure 14:
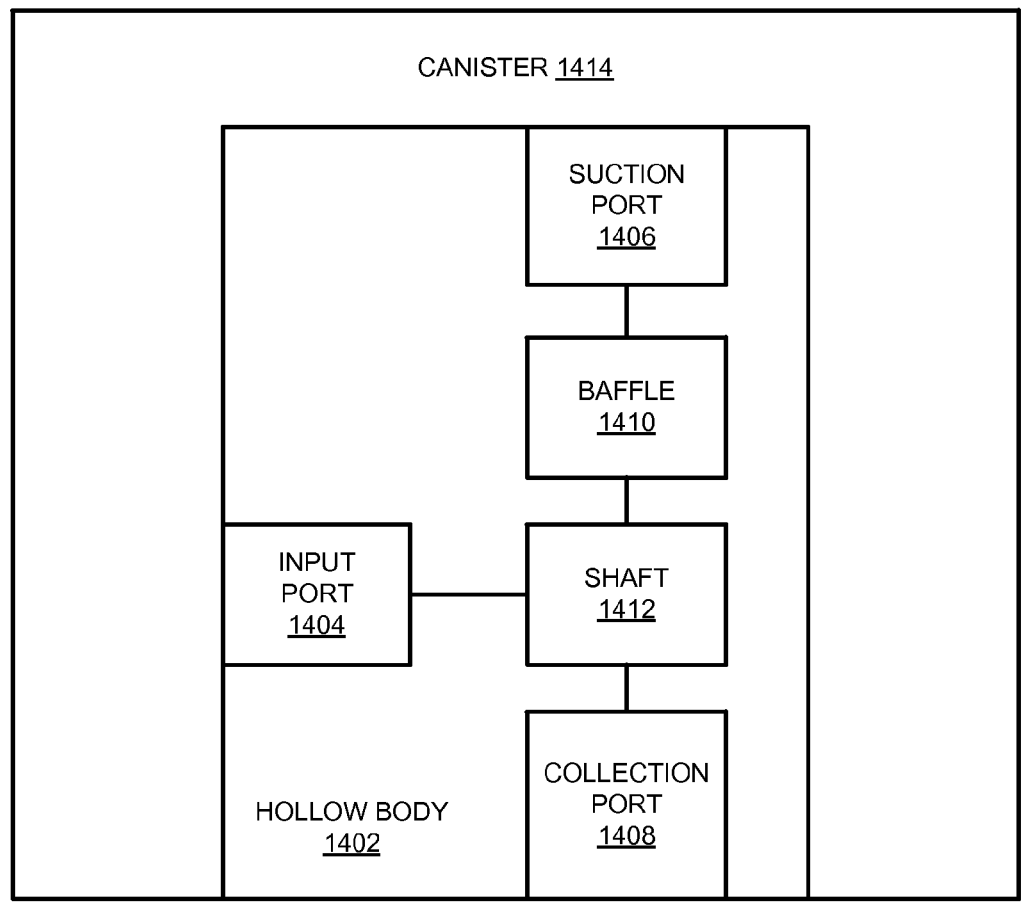
FIG. 14 is a block diagram illustrating a separator canister system.

FIG. 14 is a block diagram illustrating separator canister system 1400. In operation, separator canister system 1400 is configured to separate liquids, solids and gasses in a flow of matter. Separator canister system 1400 ejects liquids and solids separated from the flow of matter out collection port 1408 while suctioning at least gasses separated from the flow of matter out suction port 1406. Separator canister system 1400 is operated by suction received from a suction source. It should be understood that the terms "suction" and "vacuum" as used herein refer to a pressure below the surrounding ambient air pressure.

In some embodiments, separator canister system 1400 includes separator body 1402, input port 1404, suction port 1406, collection port 1408, baffle 1410, vortex element 1412 and collection canister 1414.

Separator body 1402 includes a cylindrical wall defining a cylindrical cavity. The cylindrical wall includes a first cylindrical cavity end and a second cylindrical cavity end. Separator body 1402 also forms a conical cavity. The conical cavity has a wide end and a narrow end. The wide end is mated to the second cylindrical cavity end of separator body 1402. In some embodiments, separator body 1402 is configured to operate with the first cylindrical cavity end up. Separator body 1402 is configured to allow gravity to pull at least liquid and solids separated from a flow of matter out collection port 1408, while gasses separated from the flow of matter are pulled by suction out of suction port 1406.

Separator body 1402 is configured to be integrated with collection canister 1414. Collection canister 1414 may represent a canister or a lid for a canister. In some embodiments, separator body 1402 may be integrated into the interior of collection canister 1414. In some embodiments, separator body 1402 may be integrated into a lid for collection canister 1414. In some embodiments, separator body 1402 and collection canister 1414 may be a single article of manufacture. In some embodiments, separator body 1402 may be configured to couple to canister 1414. For some forms of manufacturing, it may be desirable to manufacture separator body 1402 from a different process than used for collection canister 1414 and integrate the separator body 1402 and collection canister 1414 as part of an assembly process.

Input port 1404 is configured to receive a flow of matter. In some embodiments, input port 1404 may be integral to separator body 1402. Input port 1404 may be disposed in the cylindrical cavity wall. Input port 1404 may be located off-axis from an axis defined by the longitudinal center of the cylindrical cavity. Input port 1404 may be configured to direct a flow of matter along the cylindrical cavity wall. By directing the flow of matter along the cylindrical cavity wall, liquids and gasses may cling to the wall of the cavity due to the effects of centripetal forces. The flow of matter may be induced into separator canister system 1400 by suction received from suction port 1406 by a suction or vacuum source.

Suction port 1406 is configured to couple to a suction source. In certain embodiments, the suction source may include a vacuum pump, aspirator, and/or a positive pressure operated suction source—such as suction sources that take advantage of Venturi or Coanda effect. Suction from a suction source is transferred from suction port 1406 to input port 1404. Input port 1404 is configured to receive a flow of matter. The flow of matter is pulled into input port 1404 by the pressure difference between the ambient air pressure the lower pressure provided by the suction source. The flow of matter may include liquids, solids, and gasses, including combinations thereof in varying ratios. Suction port 1406 is disposed near the first cylindrical cavity end. Suction port 1406 provides suction received from a suction source for operating separator canister system 1400. In some embodiments, suction port 1406 may include fittings configured to attach tubing. For example, barbed or quick-disconnect type fittings may be used to couple tubing to suction port 1406. The tubing may be used to couple suction port 1406 to a suction source or to an input port 1404 of another separator system.

Collection port 1408 is configured to expel at least liquids and solids. Collection port 1408 is disposed at the narrow end of the conical cavity of separator body 1402. Collection port 1408 is configured to expel at least liquids and solids into collection canister 1414. Collection canister 1414 may be used to measure the matter collected from separator canister system 1400. Collection canister 1414 may also be used for the safe collection, transportation and disposal of waste received from collection port 1408.

Baffle 1410 is disposed between input port 1404 and suction port 1406. Baffle 1410 is configured to prevent liquids or solids in the flow from being pulled directly from input port 1404 to suction port 1406 without traversing at least a first portion of a circumference of the cylindrical wall of separator body 1402. In some embodiments, baffle 1410 may include openings configured to allow at least gasses in a flow of matter to separate from liquids and solids that maybe included in the flow. Gasses may be pulled through baffle 1410 and out suction port 1406. In an embodiment, baffle 1410 may include a solid surface located proximal to input port 1404. The solid surface that may be included in baffle 1410 may be used to prevent liquids and solids in the flow from being pulled directly from input port 1404 to suction port 1406 by allowing time for gravity to act on the liquids and solids before they reach an opening in baffle 1410. By allowing time for gravity to act on the liquids and solids as they traverse the solid surface of baffle 1410, the liquids and solids can descend towards collection port 108 and thereby not be suctioned out of the suction port 1406.

Vortex element 1412 is configured to direct a flow of matter in a cyclonic flow. The cyclonic flow and gravity may cause liquids, solids and gasses included in the flow of matter to separate. Vortex element 1412 includes a cylindrical central member disposed within the cylindrical cavity of separator body 1402. The cylindrical central member forms an annular cavity between vortex element 1412 and separator body 1402. Vortex element 1412 is configured to allow liquids and solids in the flow to pass through the annular cavity before dropping out collection port 1408. In an embodiment, vortex element 1412 may include a tapered section disposed in the conical cavity of separator body 1402. In an embodiment, vortex element 1412 may include a plurality of cylindrical sections having different diameters. The plurality of cylindrical sections may include a first section that defines a first portion of the annular cavity and a second section that defines a second portion of the annular cavity. The tapered and cylindrical sections may be configured to direct the flow within separator body 1402 in a cyclonic flow pattern. In an embodiment, baffle 1410 may be integral to vortex element 1412. In an embodiment, vortex element 1412 may include a lumen disposed within the cylindrical central member configured to allow at least gasses to pass through vortex element 1412 to suction port 1406.

Collection canister 1414 represents any portion of a collection canister. For example, collection canister 1414 may be a canister, canister wall, a lid or some other portion of a collection canister. Collection canister 1414 is configured to receive matter from collection port 1408. Collection canister 1414 may be used to measure the volume of matter received from collection port 1408. Collection canister 1414 may be used for the safe collection, transportation and disposal of collected waste.

Figure 15:
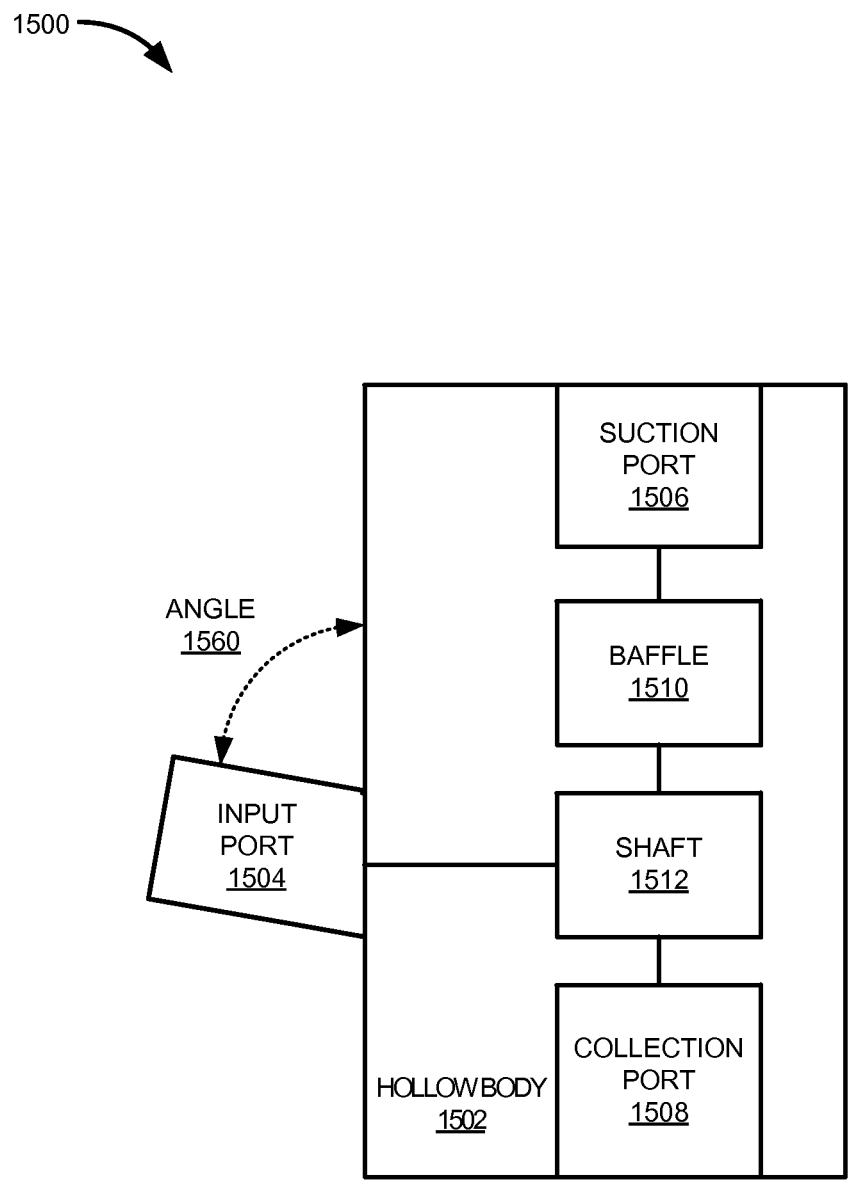
FIG. 15 is a block diagram illustrating a separator.

FIG. 15 is a block diagram illustrating separator 1500. In operation, separator 1500 is configured to separate liquids, solids and gasses in a flow of matter. Separator 1500 ejects liquids and solids separated from the flow of matter out collection port 1508 while suctioning at least gasses separated from the flow of matter out suction port 1506. Separator 1500 is operated by suction received from a suction source. It should be understood that the terms "suction" and "vacuum" as used herein refer to a pressure below the surrounding ambient air pressure.

In some embodiments, separator 1500 includes separator body 1502, input port 1504, suction port 1506, collection port 1508, baffle 1510 and vortex element 1512.

Separator body 1502 includes a cylindrical wall defining a cylindrical cavity. The cylindrical wall includes a first cylindrical cavity end and a second cylindrical cavity end. Separator body 1502 also forms a conical cavity. The conical cavity has a wide end and a narrow end. The wide end is mated to the second cylindrical cavity end of separator body 1502. In some embodiments, separator body 1502 is configured to operate with the first cylindrical cavity end up. Separator body 1502 is configured to allow gravity to pull at least liquid and solids separated from a flow of matter out collection port 1508, while gasses separated from the flow of matter are pulled by suction out of suction port 1506.

Input port 1504 is configured to receive a flow of matter. In some embodiments, input port 1504 may be integral to separator body 1502. Input port 1504 may be disposed in the cylindrical cavity wall. Input port 1504 may be located off-axis from an axis defined by the longitudinal center of the cylindrical cavity. Input port 1504 may be configured to direct a flow of matter along the cylindrical cavity wall. By directing the flow of matter along the cylindrical cavity wall, liquids and gasses may cling to the wall of the cavity due to the effects of centripetal forces. The flow of matter may be induced into separator 1500 by suction received from suction port 1506 by a suction or vacuum source.

Input port 1504 includes angle 1560. Angle 1560 represents an angle between a longitudinal axis located at the center in input port 1504 and a longitudinal axis located at the center of separator body 1502. In some embodiments, angle 1560 may equal 90°. In some embodiments, angle 1560 may be an acute angle. When angle 1560 is an acute angle, a flow of matter entering input port 1504 is directed away from baffle 1510 and towards collection port 1508. Angle 1560 may improve the operating efficiency of separator 1500 by directing the flow of matter. Angle 1560 may prevent liquids and solids from exiting suction port 1506 without first traversing at least a portion of an inner circumference of separator body 1502.

Suction port 1506 is configured to couple to a suction source. In certain embodiments, the suction source may include a vacuum pump, aspirator, and/or a positive pressure operated suction source—such as suction sources that take advantage of Venturi or Coanda effect. Suction from a suction source is transferred from suction port 1506 to input port 1504. Input port 1504 is configured to receive a flow of matter. The flow of matter is pulled into input port 1504 by the pressure difference between the ambient air pressure the lower pressure provided by the suction source. The flow of matter may include liquids, solids, and gasses, including combinations thereof in varying ratios. Suction port 1506 is disposed near the first cylindrical cavity end. Suction port 1506 provides suction received from a suction source for operating separator 1500. In some embodiments, suction port 1506 may include fittings configured to attach tubing. For example, barbed or quick-disconnect type fittings may be used to couple tubing to suction port 1506. The tubing may be used to couple suction port 1506 to a suction source or to an input port 1504 of another separator system.

Collection port 1508 is configured to expel at least liquids and solids. Collection port 1508 is disposed at the narrow end of the conical cavity of separator body 1502. In an embodiment, collection port 1508 may be configured to couple to a collection canister. A collection canister may be used to measure the matter collected from separator 1500. A collection canister may also be used for the safe collection, transportation and disposal of waste received from separator 1500. In some embodiments, collection port 1508 may be coupled to tubing or piping to direct matter to a waste drain. In some embodiments, collection port 1508 may include a mounting ring configured to form a seal between collection port 1508 to tubing or a collection canister.

Baffle 1510 is disposed between input port 1504 and suction port 1506. Baffle 1510 is configured to prevent liquids or solids in the flow from being pulled directly from input port 1504 to suction port 1506 without traversing at least a first portion of a circumference of the cylindrical wall of separator body 1502. In some embodiments, baffle 1510 may include openings configured to allow at least gasses in a flow of matter to separate from liquids and solids that maybe included in the flow. Gasses may be pulled through baffle 1510 and out suction port 1506. In an embodiment, baffle 1510 may include a solid surface located proximal to input port 1504. The solid surface that may be included in baffle 1510 may be used to prevent liquids and solids in the flow from being pulled directly from input port 1504 to suction port 1506 by allowing time for gravity to act on the liquids and solids before they reach an opening in baffle 1510. By allowing time for gravity to act on the liquids and solids as they traverse the solid surface of baffle 1510, the liquids and solids can descend towards collection port 1508 and thereby not be suctioned out of the suction port 1506.

Vortex element 1512 is configured to direct a flow of matter in a cyclonic flow. The cyclonic flow and gravity may cause liquids, solids and gasses included in the flow of matter to separate. Vortex element 1512 includes a cylindrical central member disposed within the cylindrical cavity of separator body 1502. The cylindrical central member forms an annular cavity between vortex element 1512 and separator body 1502. Vortex element 1512 is configured to allow liquids and solids in the flow to pass through the annular cavity before dropping out collection port 1508. In an embodiment, vortex element 1512 may include a tapered section disposed in the conical cavity of separator body 1502. In an embodiment, vortex element 1512 may include a plurality of cylindrical sections having different diameters. The plurality of cylindrical sections may include a first section that defines a first portion of the annular cavity and a second section that defines a second portion of the annular cavity. The tapered and cylindrical sections may be configured to direct the flow within separator body 1502 in a cyclonic flow pattern. In an embodiment, baffle 1510 may be integral to vortex element 1512. In some embodiments, vortex element 1512 may include a lumen disposed in the cylindrical central member configured to allow at least gasses to pass through vortex element 1512 to suction port 1506.

Figure 16:
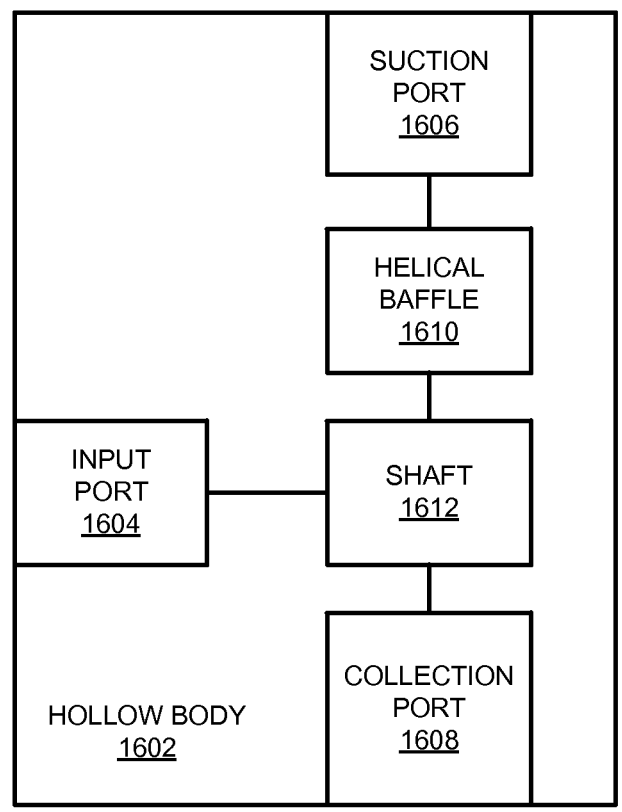
FIG. 16 is a block diagram illustrating a separator.

FIG. 16 is a block diagram illustrating separator 1600. In operation, separator 1600 is configured to separate liquids, solids and gasses in a flow of matter. Separator 1600 ejects liquids and solids separated from the flow of matter out collection port 1608 while suctioning at least gasses separated from the flow of matter out suction port 1606. Separator 1600 is operated by suction received from a suction source. It should be understood that the terms "suction" and "vacuum" as used herein refer to a pressure below the surrounding ambient air pressure.

In some embodiments, separator 1600 includes separator body 1602, input port 1604, suction port 1606, collection port 1608, helical baffle 1610 and vortex element 1612.

Separator body 1602 includes a cylindrical wall defining a cylindrical cavity. The cylindrical wall includes a first cylindrical cavity end and a second cylindrical cavity end. Separator body 1602 also forms a conical cavity. The conical cavity has a wide end and a narrow end. The wide end is mated to the second cylindrical cavity end of separator body 1602. In some embodiments, separator body 1602 is configured to operate with the first cylindrical cavity end up. Separator body 1602 is configured to allow gravity to pull at least liquid and solids separated from a flow of matter out collection port 1608, while gasses separated from the flow of matter are pulled by suction out of suction port 1606.

Input port 1604 is configured to receive a flow of matter. In some embodiments, input port 1604 may be integral to separator body 1602. Input port 1604 may be disposed in the cylindrical cavity wall. Input port 1604 may be located off-axis from an axis defined by the longitudinal center of the cylindrical cavity. Input port 1604 may be configured to direct a flow of matter along the cylindrical cavity wall. By directing the flow of matter along the cylindrical cavity wall, liquids and gasses may cling to the wall of the cavity due to the effects of centripetal forces. The flow of matter may be induced into separator 1600 by suction received from suction port 1606 by a suction or vacuum source.

Suction port 1606 is configured to couple to a suction source. In certain embodiments, the suction source may include a vacuum pump, aspirator, and/or a positive pressure operated suction source—such as suction sources that take advantage of Venturi or Coanda effect. Suction from a suction source is transferred from suction port 1606 to input port 1604. Input port 1604 is configured to receive a flow of matter. The flow of matter is pulled into input port 1604 by the pressure difference between the ambient air pressure the lower pressure provided by the suction source. The flow of matter may include liquids, solids, and gasses, including combinations thereof in varying ratios. Suction port 1606 is disposed near the first cylindrical cavity end. Suction port 1606 provides suction received from a suction source for operating separator 1600. In some embodiments, suction port 1606 may include fittings configured to attach tubing. For example, barbed or quick-disconnect type fittings may be used to couple tubing to suction port 1606. The tubing may be used to couple suction port 1606 to a suction source or to an input port 1604 of another separator system.

Collection port 1608 is configured to expel at least liquids and solids. Collection port 1608 is disposed at the narrow end of the conical cavity of separator body 1602. In an embodiment, collection port 1608 may be configured to couple to a collection canister. A collection canister may be used to measure the matter collected from separator 1600. A collection canister may also be used for the safe collection, transportation and disposal of waste received from separator 1600. In some embodiments, collection port 1608 may be coupled to tubing or piping to direct matter to a waste drain. In some embodiments, collection port 1608 may include a mounting ring configured to form a seal between collection port 1608 to tubing or a collection canister.

Helical baffle 1610 is disposed between input port 1604 and suction port 1606. Helical baffle 1610 is configured to prevent liquids or solids in the flow from being pulled directly from input port 1604 to suction port 1606 without traversing at least a first portion of a circumference of the cylindrical wall of separator body 1602. Helical baffle 1610 includes a helical portion with a start point near input port 1604 and an end point below input port 1604. The helical portion of helical baffle 1610 prevents a flow of matter traveling within separator body 1602 from intersecting with a flow of matter entering input port 1604. Helical baffle 1610 may include a second baffle disposed above input port 1604. In some embodiments, the second baffle may include openings configured to allow at least gasses in a flow of matter to separate from liquids and solids that maybe included in the flow. In an embodiment, the second baffle may include a solid surface located proximal to input port 1604. The solid surface that may be included in the second baffle may be used to prevent liquids and solids in the flow from being pulled directly from input port 1604 to suction port 1606 by allowing time for gravity to act on the liquids and solids before they reach an opening in the second baffle. By allowing time for gravity to act on the liquids and solids as they traverse the solid surface of the second baffle, the liquids and solids can descend towards collection port 1608 and thereby not be suctioned out of the suction port 1606.

Vortex element 1612 is configured to direct a flow of matter in a cyclonic flow. The cyclonic flow and gravity may cause liquids, solids and gasses included in the flow of matter to separate. Vortex element 1612 includes a cylindrical central member disposed within the cylindrical cavity of separator body 1602. The cylindrical central member forms an annular cavity between vortex element 1612 and separator body 1602. Vortex element 1612 is configured to allow liquids and solids in the flow to pass through the annular cavity before dropping out collection port 1608. In an embodiment, vortex element 1612 may include a tapered section disposed in the conical cavity of separator body 1602. In an embodiment, vortex element 1612 may include a plurality of cylindrical sections having different diameters. The plurality of cylindrical sections may include a first section that defines a first portion of the annular cavity and a second section that defines a second portion of the annular cavity. The tapered and cylindrical sections may be configured to direct the flow within separator body 1602 in a cyclonic flow pattern. In an embodiment, baffle 1610 may be integral to vortex element 1612. In some embodiments, vortex element 1612 may include a lumen passing through the center configured to allow at least gasses to be evacuated via suction port 1606. In an embodiment, vortex element 1612 may include a lumen disposed within the cylindrical central member configured to allow at least gasses to pass through vortex element 1612 to suction port 1606.

Figure 17:
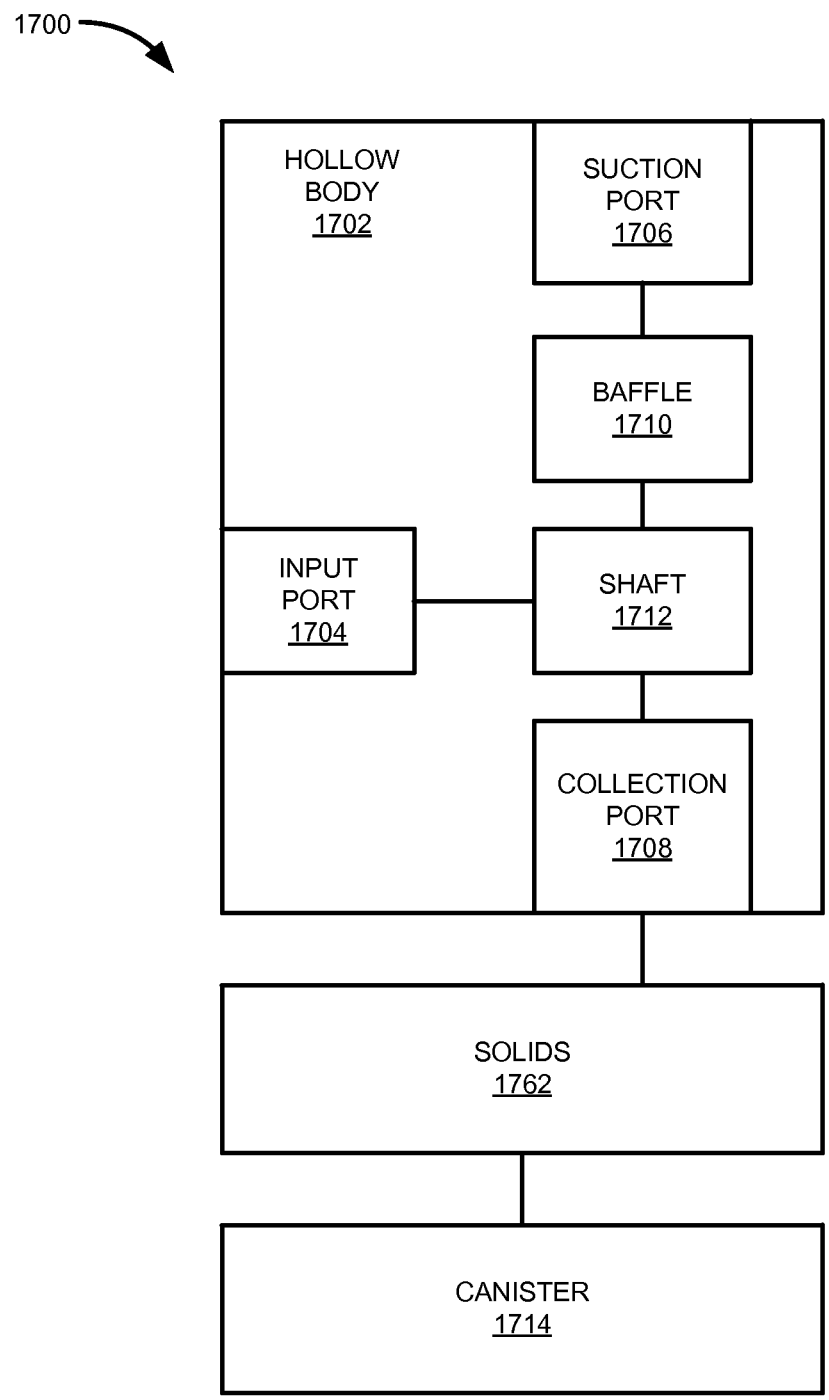
FIG. 17 is a block diagram illustrating a separator system.

FIG. 17 is a block diagram illustrating separator system 1700. In operation, separator system 1700 is configured to separate liquids, solids and gasses in a flow of matter. Separator system 1700 ejects liquids and solids separated from the flow of matter out collection port 1708 while suctioning at least gasses separated from the flow of matter out suction port 1706. Tissue trap 1762 is configured to collect solids that may be included in a flow received from collection port 1706. Tissue trap 1762 is configured to allow liquids to pass through to collection canister 1714. Separator system 1700 is operated by suction received from a suction source. It should be understood that the terms "suction" and "vacuum" as used herein refer to a pressure below the surrounding ambient air pressure.

In some embodiments, separator system 1700 includes separator body 1702, input port 1704, suction port 1706, collection port 1708, baffle 1710, vortex element 1712, collection canister 1714 and tissue trap 1762.

Separator body 1702 includes a cylindrical wall defining a cylindrical cavity. The cylindrical wall includes a first cylindrical cavity end and a second cylindrical cavity end. Separator body 1702 also forms a conical cavity. The conical cavity has a wide end and a narrow end. The wide end is mated to the second cylindrical cavity end of separator body 1702. In some embodiments, separator body 1702 is configured to operate with the first cylindrical cavity end up. Separator body 1702 is configured to allow gravity to pull at least liquid and solids separated from a flow of matter out collection port 1708, while gasses separated from the flow of matter are pulled by suction out of suction port 1706.

Input port 1704 is configured to receive a flow of matter. In some embodiments, input port 1704 may be integral to separator body 1702. Input port 1704 may be disposed in the cylindrical cavity wall. Input port 1704 may be located off-axis from an axis defined by the longitudinal center of the cylindrical cavity. Input port 1704 may be configured to direct a flow of matter along the cylindrical cavity wall. By directing the flow of matter along the cylindrical cavity wall, liquids and gasses may cling to the wall of the cavity due to the effects of centripetal forces. The flow of matter may be induced into separator system 1700 by suction received from suction port 1706 by a suction or vacuum source.

Suction port 1706 is configured to couple to a suction source. In certain embodiments, the suction source may include a vacuum pump, aspirator, and/or a positive pressure operated suction source—such as suction sources that take advantage of Venturi or Coanda effect. Suction from a suction source is transferred from suction port 1706 to input port 1704. Input port 1704 is configured to receive a flow of matter. The flow of matter is pulled into input port 1704 by the pressure difference between the ambient air pressure the lower pressure provided by the suction source. The flow of matter may include liquids, solids, and gasses, including combinations thereof in varying ratios. Suction port 1706 is disposed near the first cylindrical cavity end. Suction port 1706 provides suction received from a suction source for operating separator system 1700. In some embodiments, suction port 1706 may include fittings configured to attach tubing. For example, barbed or quick-disconnect type fittings may be used to couple tubing to suction port 1706. The tubing may be used to couple suction port 1706 to a suction source or to an input port 1704 of another separator system.

Collection port 1708 is configured to expel at least liquids and solids separated from a flow of matter received by input port 1704. Collection port 1708 is disposed near the narrow end of the conical cavity of separator body 1702. Collection port 1708 is coupled to tissue trap 1762.

Baffle 1710 is disposed between input port 1704 and suction port 1706. Baffle 1710 is configured to prevent liquids or solids in the flow from being pulled directly from input port 1704 to suction port 1706 without traversing at least a first portion of a circumference of the cylindrical wall of separator body 1702. In some embodiments, baffle 1710 may include openings configured to allow at least gasses in a flow of matter to separate from liquids and solids that maybe included in the flow. Gasses may be pulled through baffle 1710 and out suction port 1706. In an embodiment, baffle 1710 may include a solid surface located proximal to input port 1704. The solid surface that may be included in baffle 1710 may be used to prevent liquids and solids in the flow from being pulled directly from input port 1704 to suction port 1706 by allowing time for gravity to act on the liquids and solids before they reach an opening in baffle 1710. By allowing time for gravity to act on the liquids and solids as they traverse the solid surface of baffle 1710, the liquids and solids can descend towards collection port 1708 and thereby not be suctioned out of the suction port 1706.

Vortex element 1712 is configured to direct a flow of matter in a cyclonic flow. The cyclonic flow and gravity may cause liquids, solids and gasses included in the flow of matter to separate. Vortex element 1712 includes a cylindrical central member disposed within the cylindrical cavity of separator body 1702. The cylindrical central member forms an annular cavity between vortex element 1712 and separator body 1702. Vortex element 1712 is configured to allow liquids and solids in the flow to pass through the annular cavity before dropping out collection port 1708. In an embodiment, vortex element 1712 may include a tapered section disposed in the conical cavity of separator body 1702. In an embodiment, vortex element 1712 may include a plurality of cylindrical sections having different diameters. The plurality of cylindrical sections may include a first section that defines a first portion of the annular cavity and a second section that defines a second portion of the annular cavity. The tapered and cylindrical sections may be configured to direct the flow within separator body 1702 in a cyclonic flow pattern. In an embodiment, baffle 1710 may be integral to vortex element 1712. In an embodiment, vortex element 1712 may include a lumen disposed in the cylindrical central member configured to allow at least gasses to pass through the lumen to suction port 1706.

Collection canister 1714 is configured to receive waste from separator 1702. The waste may include at least liquids and solids separated from a flow of matter received at input port 1704. Collection canister 1714 may be used to measure the amount of liquids and/or solids separated from the flow of matter received at input port 1704. Collection canister 1714 may be configured to permit the safe collection, transportation and disposal of waste. In some embodiments, collection canister 1714 may include a valve configured to activate when collection canister 1714 is filled to a predetermined volume. The valve may be used to prevent waste from leaving collection canister 1714. In some embodiments, collection canister 1714 may include a commercially available collection canister.

Tissue trap 1762 is configured to trap solids that may be included in a combined flow expelled from collection port 1706. Liquids included in the combined flow are allowed to pass through tissue trap 1762 to collection canister 1714. The solids may include tissue, blood clots, foreign objects or other solid forms of matter. Tissue trap 1762 includes a means for mechanical filtration of solids that may be included in a combined flow expelled from collection port 1706. Solids collected by tissue trap 1762 may be saved for analysis or safely disposed of.

Figure 18:
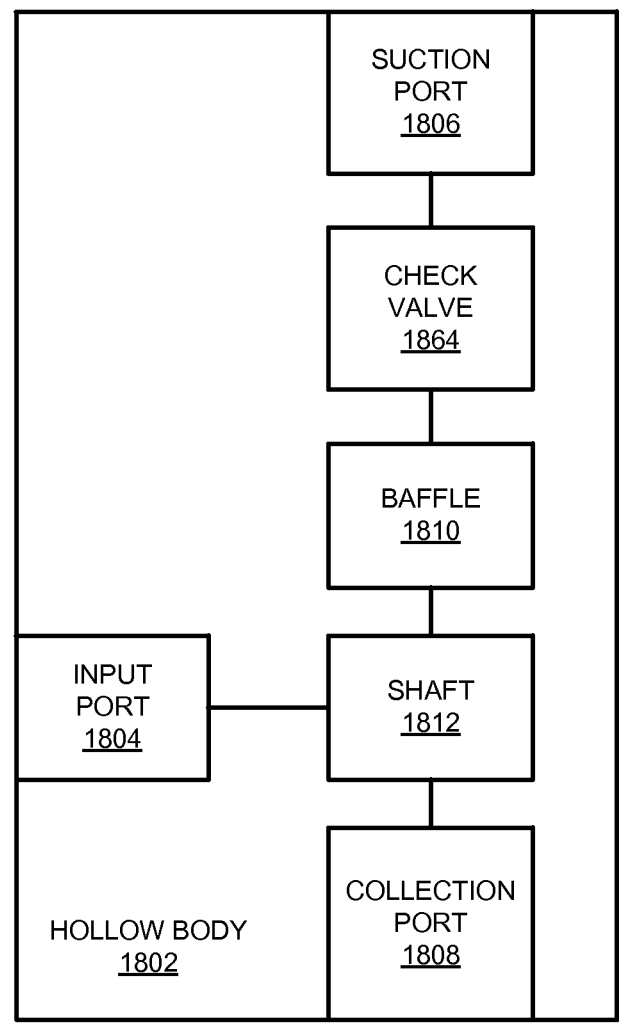
FIG. 18 is a block diagram illustrating a separator with check valve.

FIG. 18 is a block diagram illustrating separator with check valve 1800. In operation, separator with check valve 1800 is configured to separate liquids, solids and gasses in a flow of matter. Separator with check valve 1800 ejects liquids and solids separated from the flow of matter out collection port 1808 while suctioning at least gasses separated from the flow of matter out suction port 1806. Separator with check valve 1800 is operated by suction received from a suction source. It should be understood that the terms "suction" and "vacuum" as used herein refer to a pressure below the surrounding ambient air pressure. Separator with check valve is configured to prevent a flow of matter from passing through suction port 1806 when check valve 1864 is activated.

In some embodiments, separator with check valve 1800 includes separator body 1802, input port 1804, suction port 1806, collection port 1808, baffle 1810, vortex element 1812 and check valve 1864.

Separator body 1802 includes a cylindrical wall defining a cylindrical cavity. The cylindrical wall includes a first cylindrical cavity end and a second cylindrical cavity end. Separator body 1802 also forms a conical cavity. The conical cavity has a wide end and a narrow end. The wide end is mated to the second cylindrical cavity end of separator body 1802. In some embodiments, separator body 1802 is configured to operate with the first cylindrical cavity end up. Separator body 102 is configured to allow gravity to pull at least liquid and solids separated from a flow of matter out collection port 1808, while gasses separated from the flow of matter are pulled by suction out of suction port 1806.

Input port 1804 is configured to receive a flow of matter. In some embodiments, input port 1804 may be integral to separator body 1802. Input port 1804 may be disposed in the cylindrical cavity wall. Input port 1804 may be located off-axis from an axis defined by the longitudinal center of the cylindrical cavity. Input port 1804 may be configured to direct a flow of matter along the cylindrical cavity wall. By directing the flow of matter along the cylindrical cavity wall, liquids and gasses may cling to the wall of the cavity due to the effects of centripetal forces. The flow of matter may be induced into separator with check valve 1800 by suction received from suction port 1806 by a suction or vacuum source.

Suction port 1806 is configured to couple to a suction source. In certain embodiments, the suction source may include a vacuum pump, aspirator, and/or a positive pressure operated suction source—such as suction sources that take advantage of Venturi or Coanda effect. Suction from a suction source is transferred from suction port 1806 to input port 1804. Suction port 1806 is disposed near the first cylindrical cavity end. Suction port 1806 provides suction received from a suction source for operating separator with check valve 1800. In some embodiments, suction port 1806 may include fittings configured to attach tubing. For example, barbed or quick-disconnect type fittings may be used to couple tubing to suction port 1806. The tubing may be used to couple suction port 1806 to a suction source or to an input port 1804 of another separator.

Collection port 1808 is configured to expel at least liquids and solids. Collection port 1808 is disposed near the narrow end of the conical cavity of separator body 1802. In an embodiment, collection port 1808 may be configured to couple to a collection canister. A collection canister may be used to measure the matter collected from separator with check valve 1800. A collection canister may also be used for the safe collection, transportation and disposal of waste received from separator with check valve 1800. In some embodiments, collection port 1808 may be coupled to tubing or piping to direct matter to a waste drain. In some embodiments, collection port 1808 may include a mounting ring configured to form a seal between collection port 1808 to tubing or a collection canister.

Baffle 1810 is configured to prevent liquids or solids in the flow from being pulled directly from input port 1804 to suction port 1806 without traversing at least a first portion of a circumference of the cylindrical wall of separator body 1802. Baffle 1810 is disposed between input port 1804 and suction port 1806. In some embodiments, baffle 1810 may include openings configured to allow at least gasses in a flow of matter to separate from liquids and solids that maybe included in the flow. Gasses may be pulled through baffle 1810 and out suction port 1806. In an embodiment, baffle 1810 may include a solid surface located proximal to input port 1804. The solid surface that may be included in baffle 1810 may be used to prevent liquids and solids in the flow from being pulled directly from input port 1804 to suction port 1806 by allowing time for gravity to act on the liquids and solids before they reach an opening in baffle 1810. By allowing time for gravity to act on the liquids and solids as they traverse the solid surface of baffle 1810, the liquids and solids can descend towards collection port 1808 and thereby not be suctioned out of the suction port 1806.

Vortex element 1812 is configured to direct a flow of matter in a cyclonic flow. The cyclonic flow and gravity may cause liquids, solids and gasses included in the flow of matter to separate. Vortex element 1812 includes a cylindrical central member disposed within the cylindrical cavity of separator body 1802. The cylindrical central member forms an annular cavity between vortex element 1812 and separator body 1802. Vortex element 1812 is configured to allow liquids and solids in the flow to pass through the annular cavity before dropping out collection port 1808. In an embodiment, vortex element 1812 may include a tapered section disposed in the conical cavity of separator body 1802. In an embodiment, vortex element 1812 may include a plurality of cylindrical sections having different diameters. The plurality of cylindrical sections may include a first section that defines a first portion of the annular cavity and a second section that defines a second portion of the annular cavity. The tapered and cylindrical sections may be configured to direct the flow within separator body 1802 in a cyclonic flow pattern. In an embodiment, baffle 1810 may be integral to vortex element 1812. In an embodiment, vortex element 1812 may include a lumen disposed in the cylindrical central member to allow at least gasses to be pulled through the cylindrical central member and out suction port 1806.

Check valve 1864 is configured to prevent matter from passing through suction port 1806 when activated. Some events that may activate check valve 1864 include: a collection canister filling to a predetermined volume, a blockage of collection port 1808, liquids flowing directly from input port 1804 to suction port 1806 or some other event wherein it becomes undesirable for matter to pass through suction port 1806. In some embodiments, check valve 1864 may comprise a spring-operate valve. In some embodiments, check valve 1864 may include a floating member that activates when liquids fill separator body 1802 to a predetermined level. In some embodiments, check valve 1864 may include a diaphragm-operated valve. In some embodiments, check valve 1864 may include a shuttle valve.

The flow of matter may comprise a gas, a liquid, a solid, or any combination thereof. The flow of matter may comprise one or more gases. The flow of matter may comprise one or more liquids. The flow of matter may comprise one or more solids. The flow of matter may comprise biological material, such as blood, extracellular fluid, lymph fluid, urine, bile, semen, fecal matter, sweat, cells, cell fragments, tissues, tissue fragments or particulates, amniotic fluid, aqueous humour, vitreous humour, bile, breast milk, cerebrospinal fluid, chyle, exudates, gastric juice, pericardial fluid, peritoneal fluid, pleural fluid, pus, rheum, saliva, sebum, serous fluid, sputum, synovial fluid, tears, vomit, or others. The flow of matter may comprise a salt solution, saline, an electrolyte-based fluid, sugar-containing fluids, or carbon dioxide gas. The flow of matter may comprise surgical waste, such as lavage fluids. The flow of matter may comprise gases, liquids, or solids generated from a surgical procedure.

One or more components of the system are disposable. One or more surgical instruments, one or more flow separation devices, one or more canisters, or any combination thereof is disposable. A surgical instrument is disposable. A flow separation device is disposable. A canister is disposable.

One or more components of the system are suitable for more than a single use. One or more surgical instruments, one or more flow separation devices, one or more canisters, or any combination thereof is suitable for more than a single use. A surgical instrument is suitable for more than a single use. A flow separation device is suitable for more than a single use. A canister is suitable for more than a single use.

One or more components of the system are sterilized. One or more surgical instruments, one or more flow separation devices, one or more canisters, or any combination thereof is sterilized. A surgical instrument is sterilized. A flow separation device is sterilized. A canister is sterilized.

Figure 19:
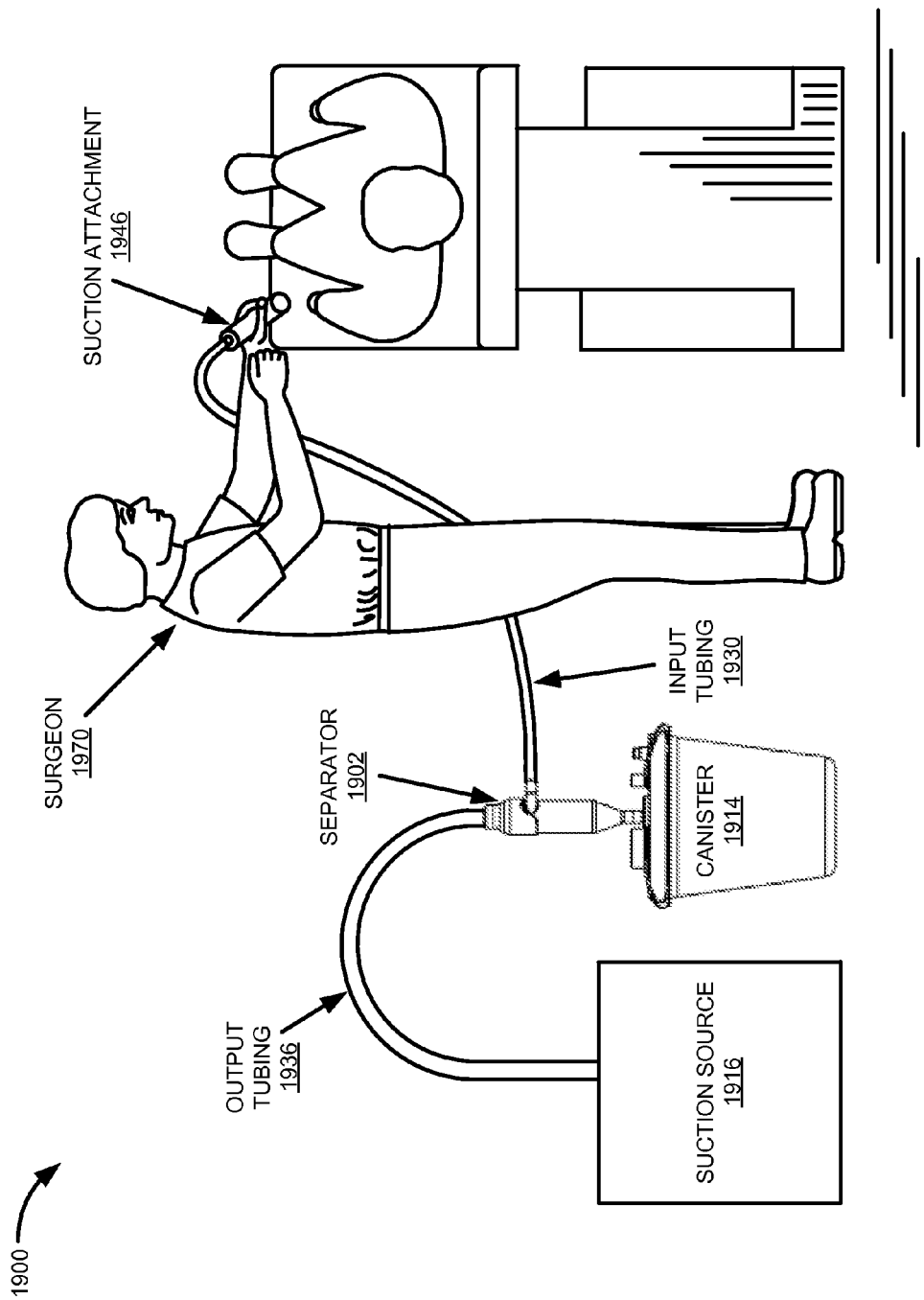
FIG. 19 is a diagram illustrating the system in a surgical use setting.

FIG. 19 shows a separator 1902 as an element of a surgical system 1900. In some embodiments, surgical system 1900 comprises suction source 1916, tubing 1936, separator 1902, canister 1914, tubing 1930, and suction attachment 1946.

In system 1900 a suction source 1916 applies suction to a separator 1902 as described herein. The suction provided by the suction source 1916 facilitates separation of a gas from a solid and/or liquid suction flow within the separator 1902 as described herein. In some embodiments, the gas comprises surgical smoke generated by an electrocautery instrument. In some embodiments, surgical smoke that is separated with separator 1902 is evacuated into a trap. In some embodiments, surgical smoke that is separated with separator 1902 is passed through a filter or series of filters configured to trap toxic particles and or biological elements (e.g. viruses) within the smoke. Suction attachment 1946 may comprise, for example, a suction tip such as for example, a Yankauer tip. Suction attachment 1946 is used by a surgeon to suction material from a surgical field which includes, for example, blood, fat, pus, irrigation fluid, bone, surgical smoke, and other similar organic and inorganic materials. Materials suctioned from the surgical field are transmitted to the separator 1902 through input tubing 1930. As described herein, the material suctioned through the surgical suction instrument is separated in the separator 1902 so that a gas (e.g. surgical smoke) is drawn out through the top of the separator 1902 and any liquid and/or solid material is drawn by gravity (and/or suction) into the canister 1914. It should be understood that while one canister and separator are shown, surgical system 1900 may also be configured for use with two or more separators either in series or in parallel as described herein.

A system may comprise a surgical instrument, a suction source, and one or more separators. The one or more separators may be operatively connected in series, such as connected via tubing. In some cases, the system may also comprise collection canisters attachable to each of the one or more separators. In some cases, at least one of the one or more separators comprises a canister formed therein. A system comprising one or more separators in series may permit filling a volume of a first canister in the series with a liquid of the flow of matter followed by filling a volume of a second canister in the series with a liquid of the flow of matter followed by filling a volume of a third canister in the series and so on.

A second canister may not be filled with a liquid from the flow of matter until at least a portion of the volume of the first canister is filled. A third canister may not be filled with a liquid until at least a portion of the volume of the second canister and the first canister are filled. The portion filled with liquid may be about 70%, about 75%, about 80%, about 85%, about 90%, about 95%, about 96%, about 97%, about 98%, about 99%, or 100% of the total canister volume. The portion filled with liquid may be at least about 70% of the total canister volume. The portion filled may be at least about 80% of the total canister volume. The portion filled may be at least about 80% of the total canister volume. The portion filled may be at least about 90% of the total canister volume. The portion filled may be at least about 95% of the total canister volume.

When a portion of the volume of a first canister, such as about 90%, is filled with liquid, the flow of matter may be automatically directed to the second separator in the series to fill the second canister. When a portion of the volume of the first canister and the second canister is filled with liquid, the flow of matter may be automatically directed to the third separator in the series to separate gas and liquid from the flow of matter and to fill the third canister. A system of separators in series may permit the collection of liquids from a flow of matter into a series of canisters and separation of gas from the flow of matter during continuous suction use of the surgical instrument. A system of separators in series permits continuous suction use of the surgical instrument with a greater liquid collection volume compared to a single separator.

Figure 20A:
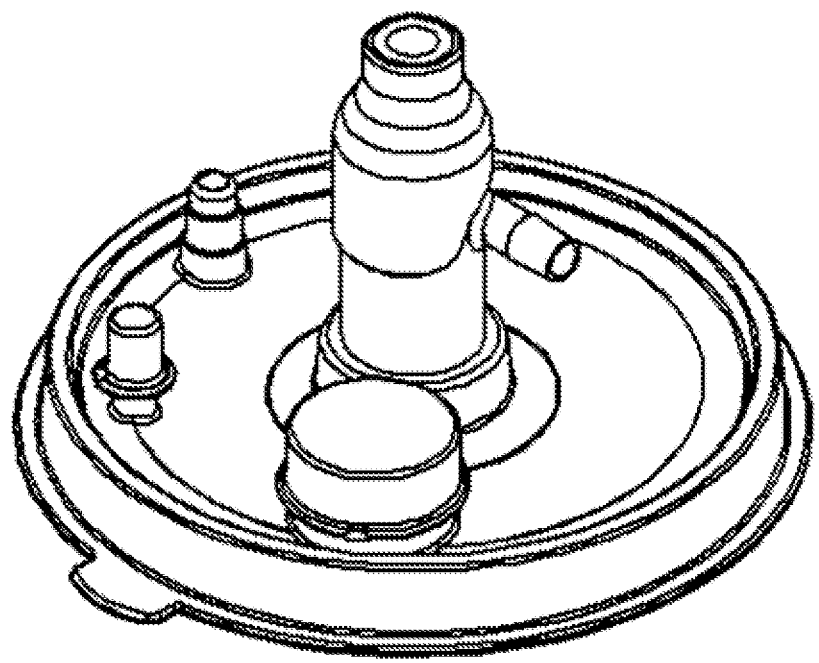
FIG. 20A is a diagram illustrating a flow separation device attachable or formed therein a canister lid.

FIG. 20A shows an embodiment of a separator coupled with a canister top. In the shown embodiment, the separator interface with the canister top provides for forgoing the convergence at the bottom of the separator, so that the separator maintains its widest diameter and empties directly into the canister at its widest diameter (i.e. without tapering of separator to form a smaller exit port). In some embodiments, the canister top is configured to receive and couple with a wider diameter exit (i.e. opening) of a separator as shown. In some embodiments, the canister top and the separator are fused to form one continuous piece.

Figure 20B:
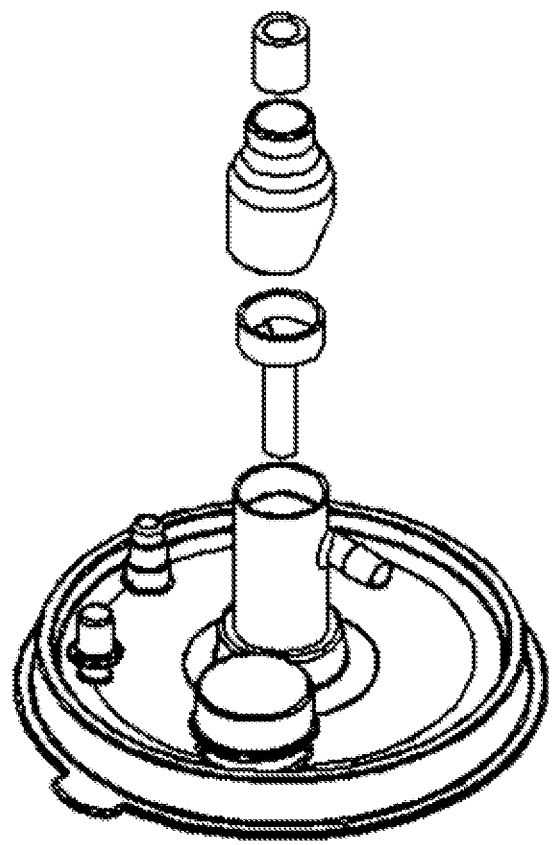
FIG. 20B is a diagram illustrating a flow separation device attachable or formed therein a canister lid.

FIG. 20B shows an exploded view of the separator components as described herein. It should be understood that the embodiment of the separator and canister top shown in FIGS. 20A and 20B are configured to be used with any and all devices, systems, and methods described herein.

In some embodiments, a flow separation device (i.e. a separator) is operatively coupled to a canister. In some embodiments, a flow separation device is retrofitted to an existing canister. In some embodiments, a flow separation device is integrated into a canister.

A flow separation device is operatively coupled to a surgical instrument. A flow separation device is operatively coupled to a surgical instrument via an input port. A flow separation device is in fluid communication with a surgical instrument via a tubing. A flow separation device is attachable to a surgical instrument. A flow separation device is retrofitted to an existing surgical instrument. A flow separation device is an accessory, such as an optional accessory, to a surgical instrument.

In some embodiments, a flow separation device is operatively coupled to a smoke filtration canister. In some embodiments, a flow separation device is operatively coupled to a smoke filtration canister via a port, such as a suction port. In some embodiments, a flow separation device is in fluid communication with a smoke filtration canister via a tubing. In some embodiments, a flow separation device is attachable to a smoke filtration canister. In some embodiments, a flow separation device is retrofitted to an existing smoke filtration canister. In some embodiments, a flow separation device is formed therein a smoke filtration canister. In some embodiments, a flow separation device is integrated into a smoke filtration canister. In some embodiments, a flow separation device is an accessory, such as an optional accessory, to a smoke filtration canister.

In some embodiments, a flow of matter enters the flow separation device from the surgical instrument at the input port. The flow of matter may comprise a gas, a liquid, a solid, or any combination thereof. The flow separation device enhances the suction capacity of the surgical instrument compared to a surgical instrument without a flow separation device operatively coupled. The flow separation device enhances the suction capacity of a suction source, such as a passive suction source, compared to a system without a flow separation device operatively coupled. The flow separation device is configured to separate the gas, the liquid, the solid, or any combination thereof. The gas exits the flow separation device from a different port that the liquid exits. For example, the gas exits the suction port and the fluid exits the collection port. In some embodiments, a liquid exiting the collection port of the flow separation device is collected in a canister, such as a collection canister, that is operatively coupled to the flow separation device. The solid is collected in one or more filters of the flow separation device. In some embodiments, the solid also exits the collection port with the liquid.

The system may include one or more valves, such as a shut off valve, a ball valve, a butterfly valve, a clapper valve, a check valve, a choke valve, a diaphragm valve, a gate valve, a pinch valve, a piston valve, a plug valve, a poppet valve, a safety valve, or any combination thereof. The one or more valves is operatively coupled to the flow separation device, the surgical instrument, the suction source, or any combination thereof. One or more valves are included as a safety feature of the system. One or more valves are included to optimize performance of the system. For example, a shut off valve may shut off the system if a volume of liquid within the flow separation device exceeds a specified volume, such as a volume greater than 70%, 75%, 80%, 85%, 90%, 95%, 96%, 97%, 98%, 99% or greater the total inner volume of the hollow body of the flow separation device. A shut off valve may shut off the system if a volume of liquid within the flow separation device exceeds a volume greater than 70% the total inner volume of the hollow body of the flow separation device. A shut off valve may shut off the system if a volume of liquid within the flow separation device exceeds a volume greater than 80% the total inner volume of the hollow body of the flow separation device. A shut off valve may shut off the system if a volume of liquid within the flow separation device causes the liquid to begin to exit all ports of the flow separation device.

The system may include one or more alerts. The one or more alerts are operatively coupled to the flow separation device, the surgical instrument, the suction source, or any combination thereof. One or more alerts are included as a safety feature of the system. One or more alerts are included to optimize performance of the system. One or more alerts are a visual alert, an audible alert, a mechanical alert, or any combination thereof. A visual alert is a constant light, a flashing light, a strobing light, a light of a particular color (such as red =system off and green =system on), or any combination thereof. An audible alert is a ring, buzz, chime, bell, horn, vibration or other audible sound. An alert is a mechanical alert such as a pop-out button or flip tab.

Figure 21C:
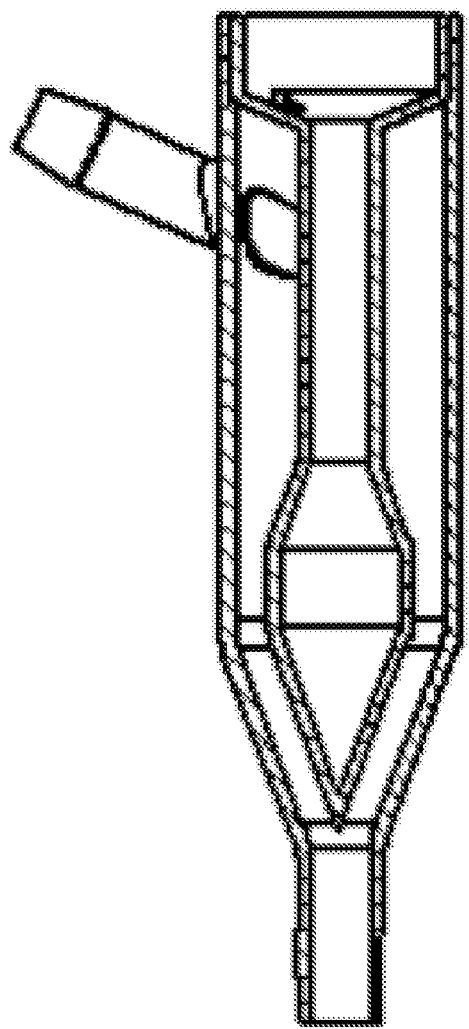
FIG. 21C is a cross-section of a flow separation device with an angled input port.

FIGS. 21A, 21B, and 21C show an embodiment of the separator wherein the input port of the separator at an angle relative to a central axis of the hollow body that is less than 90 degrees. In some embodiments, the input port is angled relative to the central axis at about 85°, 80°, 75°, 70°, 65°, 60°, 55°, 50°, 45°, 40°, 35°, 30°, 25°, 20° or less. In some embodiments, the input port is angled at about 70° or less. In some embodiments, he input port is angled at about 60° or less. The input port is angled at about 50° or less. In some embodiments, the input port is angled at about 40° or less. In some embodiments, the input port is angled at about 30° or less. In some embodiments, the input port is angled from about 20° to about 50°. In some embodiments, the input port is angled from about 40° to about 70°. In some embodiments, the input port of the separator is angled to enhance entry of the flow of matter into the input port, enhance a cyclonic pattern of flow along an inner surface of the hollow body, or enhance movement of liquid towards the collection port, or any combination thereof. In some embodiments, the cyclonic pattern of flow along an inner surface of the hollow body may aid in separation of a gas from a liquid of the flow of matter. In some embodiments, the input port of the separator is configured to direct a flow entering the separator against the wall of the separator as the flow enters the separator.

Figure 21D:
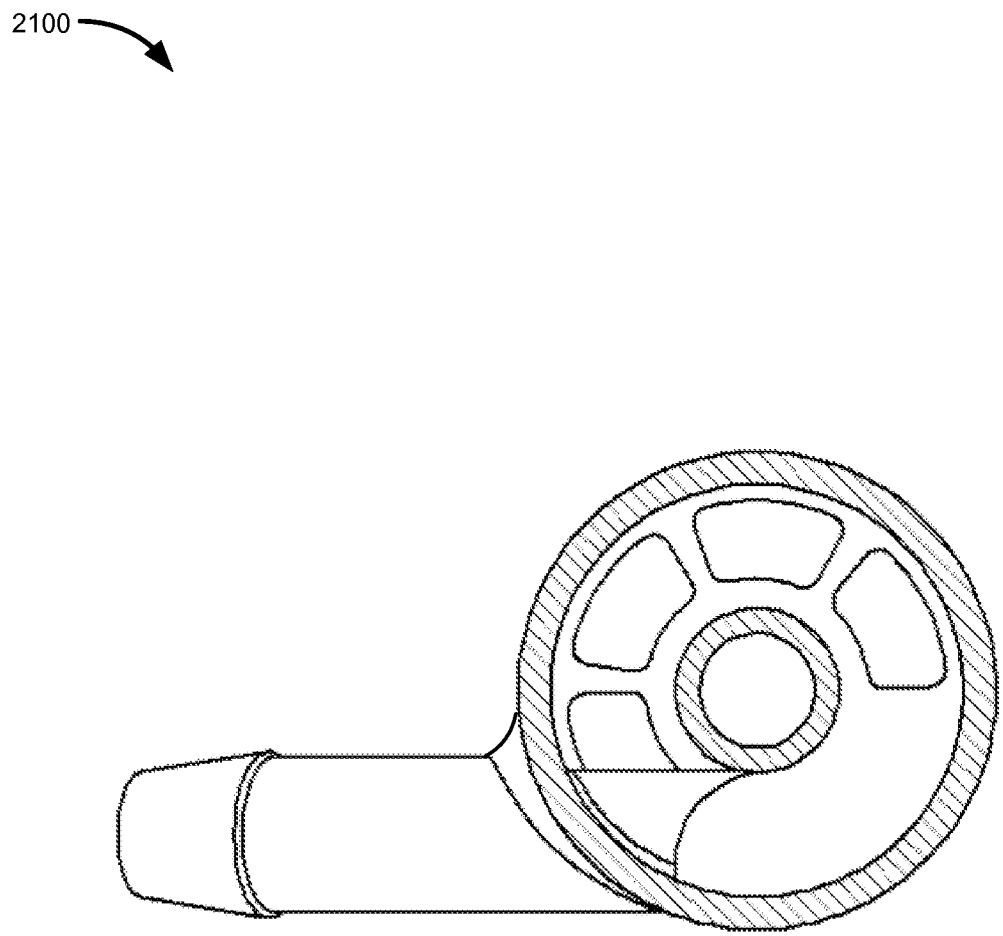
FIG. 21D is a top view of a flow separation device showing the relation between the input port and the baffle within the hollow body.

FIG. 21D shows a bottom view of an embodiment wherein an input port opening enters the separator and contacts the central column (or shaft) of the separator. Typically fluid traveling from a smaller diameter conduit into a larger diameter conduit tends to expand at the point of intersection of the smaller conduit with the larger conduit. Here, as shown the opening of the input port enters into the larger diameter interior of the separator so that fluid expansion is decreased (as compared to, for example, an input port that opens directly into a larger conduit). Also shown, the opening of the input port is shaped so that a side of the input port opening extends and contacts the central column (or shaft) while the opening gradually curves away from that point so that the edge of the opening tapers away from the point at which the opening of the input port contacts the central column. This configuration directs flow of liquid and/or solid suction material against the inner surface of the separator while the contact of the input port with the column tends to draw the flow of gaseous components in the suction flow around the central column due to a Coanda effect. The initial separation of the gas and fluid due to the shape and positon of the input port as shown in FIG. 21D enhances the separation as described herein.

Figure 22A:
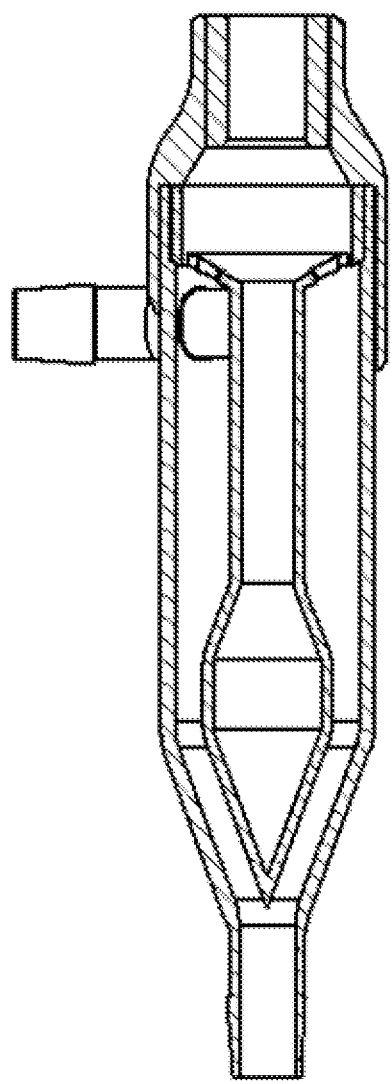
FIG. 22A is a cross-section of the flow separation device.
Figure 22B:
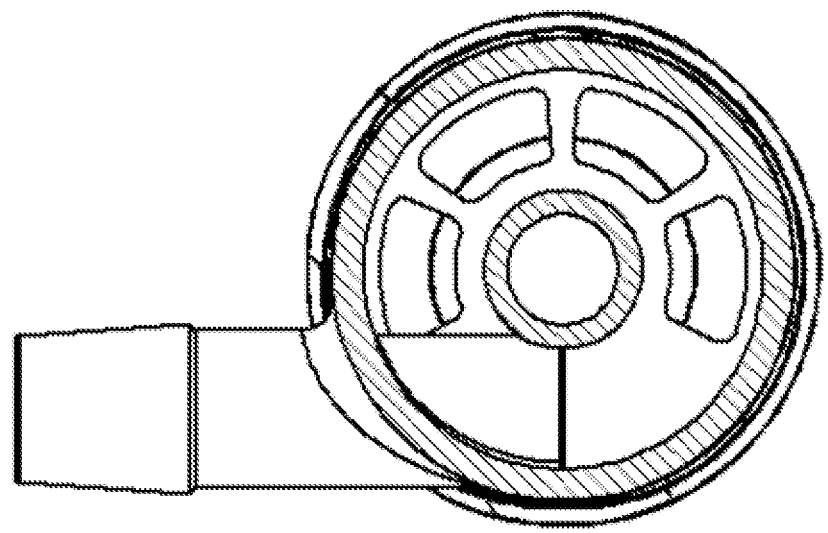
FIG. 22B is a top view of a flow separation device showing the relation between the input port and the baffle within the hollow body.
Figure 23D:
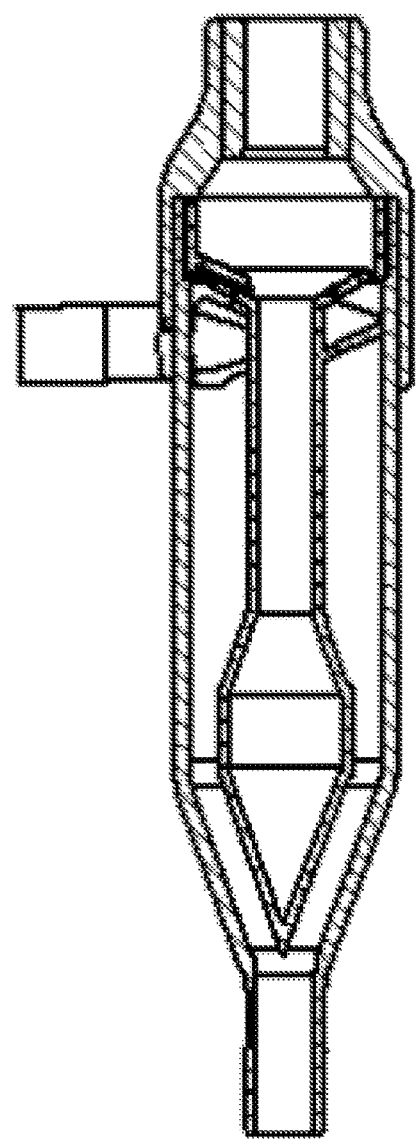
FIG. 23D is a cross-section of the flow separation device illustrating the helical baffle.

FIGS. 22A and 22B show a side view and bottom view respectively of an input port opening into a separator wherein the opening contacts the central column (or shaft). Unlike the embodiment shown in FIG. 21D the opening of the input port is essentially flat without any taper. Similar to the embodiment shown in FIG. 21D, a gaseous component of a suction flow will tend to be drawn to around the central column of the separator when the suction flow enters the separator due to the Coanda effect. Because the opening of the input port opens into the separator, as in FIG. 21D, there will be a decrease or prevention of expansion of the suction flow as it leaves the input port.

Also shown in FIGS. 21D, and 22B, a baffle comprises a solid surface that is proximal to the opening of the input port. Thus, openings in the baffle do not extend around the entire circumference of the baffle. The solid surface of the baffle and its position immediately proximal to the opening of the input port blocks liquids and or/solids entering the separator so that the liquids and/or solids are not immediately drawn up and out of the suction port of the separator. Rather blocking the initial escape of solid and/or liquid components of the suction flow by the solid portion of the baffle allows for gravity (and/or suction from the direction of the canister) to draw the liquids and/or solids down towards the bottom of the separator. The gaseous components of the mixture are also initially blocked by the solid component of the baffle but these components are affected more strongly by the suction force through the suction port (i.e. more strongly than gravity and/or a suction force from the direction of the canister) which draws the gaseous components up and out of the separator through the holes in the baffle which are positioned past the solid portion of the baffle.

It should be understood that embodiments of baffles with a solid portion near an input port may be used with any and all devices, systems, and methods described herein.

In some embodiments, the separator comprises one or more baffles. The one or more baffles may individually comprise a plurality of openings. The plurality of openings may comprise 3, 4, 5, 6, 7, 8, 9, 10, or more openings. In some embodiments, the plurality of openings is 3. In some embodiments, the plurality of openings is 4. In some embodiments, the plurality of openings is 5. In some embodiments, the plurality of openings is 6. In some embodiments, the plurality of openings is 7. In some embodiments, the plurality of openings is 8. In some embodiments, the plurality of openings is 9. In some embodiments, the plurality of openings is 10. In some embodiments, the plurality of openings is positioned on the one or more baffles such that they are distal to the input port. In some embodiments, the one or more baffles is positioned on a first end of the shaft that is adjacent a second conical end. In some embodiments, the one or more baffles are configured to receive at least a portion of the flow of matter to pass through the one or more openings. In some embodiments, the one or more baffles are configured to aid in the separation of gas from liquid of the flow of matter entering the separator.

FIG. 23A-23D show different views of a baffle coupled with helical surface. In some embodiments, a baffle may be shaped or coupled with a helix. The helix is configured to guide the flow of the liquid and/or solid components within the suction flow along a helical track down towards the bottom (i.e. the exit port) of the separator. A helical baffle may be right-handed or left-handed. The helical baffle may be a conical helix, a circular helix, a cylindrical helix, or other. A helical baffle may form a single complete rotation about the shaft. A helical baffle may form a single complete rotation about the hollow body. A helical baffle may form more than one complete rotation about the shaft. A helical baffle may form rotations along a portion of the shaft. A helical baffle may form rotations along a portion of the hollow body. A helical baffle may form rotations about a shaft or the hollow body along a portion of the shaft or hollow body between the suction port and the input port.

The shaft may comprise one or more helical structures, such as indentations or protrusions. A helical structure may be right-handed or left-handed. The helical structure may be a conic helix, a circular helix, a cylindrical helix, or other. A helical structure may form a single complete rotation about the shaft. A helical structure may form more than one complete rotation about the shaft. A helical structure may form rotations along a portion of the shaft. A helical structure may form rotations about a shaft along a portion of the shaft between the suction port and the input port. A helical structure may form rotations about a shaft along a portion of the shaft between the input port and the collection port. A helical structure may form rotations about a shaft along the entire length of the shaft.

Figure 24A:
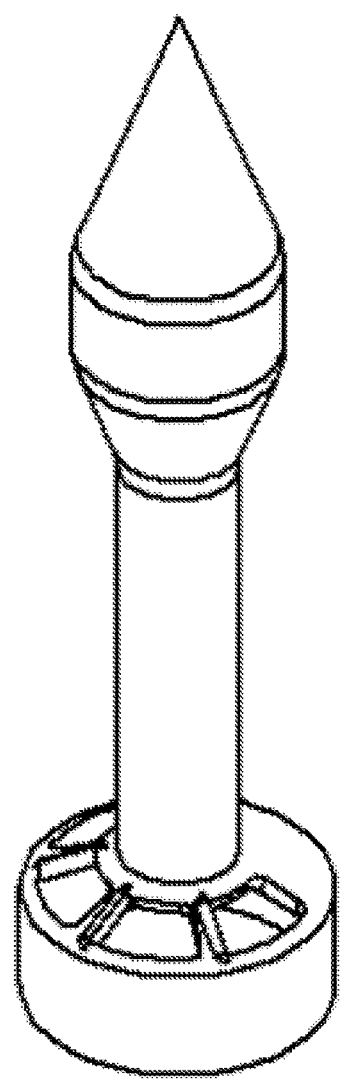
FIG. 24A is a diagram illustrating the shaft with a bulbous end.

FIG. 24A shows an embodiment of a shaft and a baffle of a separator. In the shown embodiment, the shaft comprises a bulbous portion with the top most portion shaped comprising a cone. A shaft may be integrated into a separator or attachable thereto an inner portion of the hollow body of the separator.

A shaft may comprise one or more openings. An opening in a shaft may permit one or more gases to exit the hollow body, such as via the hollow lumen of the shaft towards the suction port. An opening on the shaft may be a circumferential gap space, such as an annular opening. An opening on the shaft may be positioned distal to the input port. An opening on the shaft may be positioned on a portion of the bulbous end.

The shaft may be an elongate shaft. The shaft may be a cylindrical shaft. The shaft may comprise a hollow lumen. The shaft may comprise one or more circumferential cross-section areas along the length of the shaft. Circumferential cross-section areas along the length of the shaft may be the same. Circumferential cross-section areas along the length of the shaft may vary. For example, the varied circumferential cross-section areas may form a shaft with a bulbous end, a protruding end, a spherical end, or other. Varying the circumferential cross-section areas along the shaft may enhance laminar flow within the hollow body, may reduce eddy currents, may prevent flow convergence, may prevent flow divergence, or any combination thereof. For example, a shaft comprising a bulbous end positioned adjacent to a port, such as a collection port, having a circumferential cross-section area that is different than the circumferential cross-section area of the hollow body, may enhance laminar flow within the hollow body, may reduce eddy currents, may prevent flow convergence, may prevent flow divergence, or any combination thereof.

A bulbous end of a shaft may form an initial angle of circumferential expansion and a secondary angle of circumferential contraction. The initial angle and the secondary angle may be the same. The initial angle and the secondary angle may be different.

The initial angle may be about 5 degrees, 10 degrees, 15 degrees, 20 degrees, 25 degrees, 30 degrees, 35 degrees, 40 degrees, 45 degrees, 50 degrees, 55 degrees, 60 degrees, 65 degrees, 70 degrees, 75 degrees, or 80 degrees relative a central axis of the shaft. The initial angle may be about 25 degrees relative a central vertical axis of the shaft. The initial angle may be about 30 degrees relative a central vertical axis of the shaft. The initial angle may be about 35 degrees relative a central vertical axis of the shaft. The initial angle may be about 40 degrees relative a central vertical axis of the shaft. The initial angle may be about 40 degrees relative a central vertical axis of the shaft.

The secondary angle may be about 5 degrees, 10 degrees, 15 degrees, 20 degrees, 25 degrees, 30 degrees, 35 degrees, 40 degrees, 45 degrees, 50 degrees, 55 degrees, 60 degrees, 65 degrees, 70 degrees, 75 degrees, or 80 degrees relative a central vertical axis of the shaft. The secondary angle may be about 25 degrees relative a central vertical axis of the shaft. The secondary angle may be about 30 degrees relative a central vertical axis of the shaft. The secondary angle may be about 35 degrees relative a central vertical axis of the shaft. The secondary angle may be about 40 degrees relative a central vertical axis of the shaft. The secondary angle may be about 40 degrees relative a central vertical axis of the shaft.

The separator may comprise one or more baffles within the hollow body. A baffle may direct a flow of matter, such as a flow of matter entering an inner volume of a hollow body. In some cases, the flow of matter may enter the inner volume via an input port. A baffle may direct a flow of liquid entering an input port towards a collection port, such as a cyclonic flow. The baffle may direct the flow of liquid away from a suction port. The baffle may encourage separation of a flow of matter into a liquid flow stream and a gas flow stream.

A baffle may be angled relative to a central vertical axis of the shaft. A baffle may be angled at about 20 degrees, 25 degrees, 30 degrees, 35 degrees, 40 degrees, 45 degrees, 50 degrees, 55 degrees, 60 degrees, 65 degrees, 70 degrees, or about 75 degrees relative to a central vertical axis of the shaft. A baffle may be angled at about 25 degrees relative to a central vertical axis of the shaft. A baffle may be angled at about 30 degrees relative to a central vertical axis of the shaft. A baffle may be angled at about 35 degrees relative to a central vertical axis of the shaft. A baffle may be angled at about 40 degrees relative to a central vertical axis of the shaft.

One or more baffles may be attachable thereto the shaft. The one or more baffles may be formed therein the shaft. A baffle may be positioned along the shaft at a location that is distal to the collection port and adjacent to a suction port. A baffle may be positioned along the shaft at a location that is distal to the collection port and between the suction port and the input port. A baffle may prevent liquids entering the hollow body via the input port from exiting the suction port. A baffle may be a physical barrier to prevent liquids entering the hollow body via the input port from exiting the suction port. A baffle may direct liquids entering the hollow body via the input port to flow towards a collection port.

A baffle may comprise one or more openings. A baffle may be perforated. Perforations or openings in a baffle may permit one or more gases to exit the hollow body, such as via the suction port. A baffle may comprise at least 1 opening. A baffle may comprise at least 2 openings. A baffle may comprise at least 3 openings. A baffle may comprise at least 4 openings. A baffle may comprise at least 5 openings. A baffle may comprise at least 6 openings. An opening on a baffle may circular shaped, rectangular shaped, oval shaped, square shaped, square shaped with rounded edges, or others. An opening on a baffle may be a circumferential gap space, such as an annular opening. An annular opening on a baffle may be positioned adjacent to the shaft and distal from the outer surface of the hollow body. An opening on a baffle may be positioned distal to the input port.

Figure 24B:
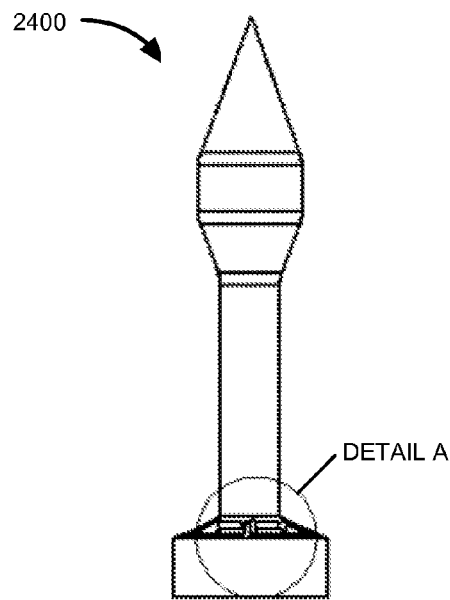
FIG. 24B-C are diagrams illustrating the openings on a baffle of the device.
Figure 24C:
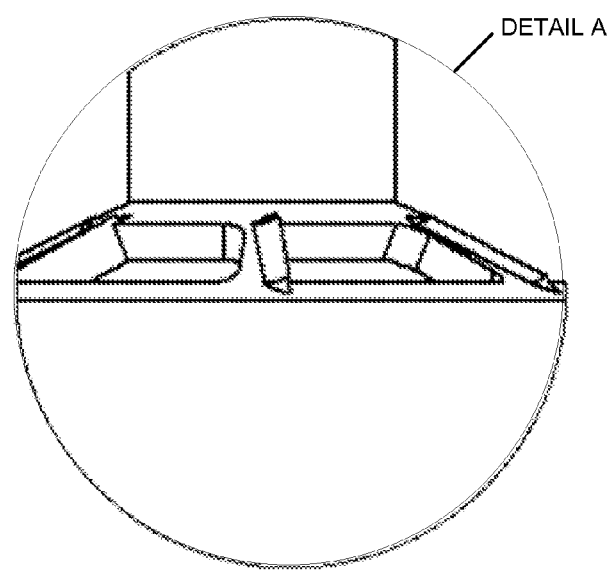

FIG. 24A-24C shows different views of embodiments of baffles including direction wings or fins on the openings in the baffle. In these embodiments, the wings or fins further block fluid and/or solids in the suction mixture from passing out through the openings in the baffle. The wings or fins are positioned so that they are directly between the direction of flow and the openings in the baffle and shield the openings by both physically blocking liquid and/or solid flow into the openings and redirecting the liquid and/or solid components downwards. In some embodiments the wings or fins have a ramp shape so that they direct the flow of a liquid and/or solid away from the opening in the baffle. The wings or fins are configured to not block gas entry into the openings.

EXAMPLE

|  | TIME (seconds) | SUCTION |
|---|---|---|
| Yankauer (no SLS) | 18 | Strong |
| Yankauer (1 SLS) | 11 | Strong |
| FIRST (no SLS) | 133 | Minimal |
| FIRST (1 SLS) | 70 | Minimal |
| FIRST (2 SLS + return loop) | 50 | Minimal |

Table 1 is a chart illustrating test results of a separator. The chart illustrates data relating to two different types of suction devices with and without a separator in use. The first type of suction device listed in the chart is a Yankauer suction tip. A Yankauer suction tip is an oral suctioning tool typically comprised of a firm plastic suction tip with a large opening surrounded by a bulbous head and is designed to allow effective suction without damaging surrounding tissues. The second type of suction device (FIRST) listed in the chart is a suction device designed for use in various surgical procedures and may include ports that is variably opened and closed to adjust a ratio of liquids, solids and gasses suctioned by the FIRST device. The term "SLS" refers to the separator disclosed herein.

The test setup included four collection canisters coupled in series, as is used in a common operating room setup. FIG. 12 illustrates an example of two collection canisters 1214, 1234 including two separators 1202, 1222 coupled in series. The canisters were coupled to a CONMED® System 1200™ Smoke Evacuation System (SES). The chart illustrates the time taken to suction 500 cc of 35% glycerol solution at room temperature. In addition, the chart illustrates data pertaining to the suction strength of the two suction devices.

As illustrated in Table 1, the Yankauer device provided strong suction with and without a separator in use. However, suction time decreased from 18 seconds to 11 seconds with the use of a separator system, such as the separator examples described herein. The FIRST device was able to suction 500 cc of 35% glycerol in 133 seconds without the use of a separator. Adding one separator to the system decreased the suction time to 70 seconds. Performance of the FIRST device was improved even further by adding a second separator to the system. The suction time of the FIRST device in conjunction with two separators decreased to 50 seconds. The data shows that the use of a separator, the examples as described herein, may reduce the suction time of various suction times by nearly one-half.

The foregoing description of the invention has been presented for purposes of illustration and description. It is not intended to be exhaustive or to limit the invention to the precise form disclosed, and other modifications and variations is possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. A flow separation device, comprising:
a separator body having a cylindrical cavity having a cylindrical wall and first cylindrical cavity end and a second cylindrical cavity end, configured to operate with the first cylindrical cavity end up;
a conical cavity having a narrow end and a wide end, the wide end mated to the second cylindrical cavity end;
an input port disposed in the cylindrical cavity wall, configured to receive a flow of matter;
a suction port mated to the first cylindrical cavity end and configured to couple to a suction source;
a collection port mated to the narrow end of the conical cavity and configured to couple to a waste deposit;
a baffle disposed between the input port and the suction port, wherein the baffle comprises a plurality of openings to allow passage of the flow of matter, comprising separated portions thereof, out of the suction port, the baffle being configured to prevent the flow of matter from passing directly from the input port to the suction port without first traversing at least a portion of a circumference of an interior of the cylindrical wall; and
a cylindrical shaft disposed within a center of the cylindrical cavity and configured to direct the flow of matter within the cylindrical cavity.

2. The separator of claim 1, wherein the input port is located off-axis of an axis defined by the longitudinal center of the separator body.

3. The separator of claim 1, wherein the input port is located closer to the first cylindrical cavity end than the second cylindrical cavity end.

4. The separator of claim 1, wherein the suction source comprises a vacuum pump.

5. The separator of claim 1, wherein the suction source comprises a positive pressure operated suction generator that utilizes a Coanda effect.

6. The separator of claim 1, wherein the suction source comprises a positive pressure operated suction generator that utilizes a Venturi effect.

7. The separator of claim 1, wherein the baffle comprises a solid surface located proximal to the input port and distal to the plurality of openings, configured to prevent the flow of matter, comprising separated portions thereof, from passing directly from the input port to the suction port without first traversing at least a portion of a circumference of the cylindrical cavity wall.

8. The separator of claim 1, wherein the baffle is integral to the cylindrical shaft.

9. The separator of claim 1, wherein the cylindrical shaft comprises a plurality of conic sections each comprising a wide end and a narrow end of varying diameters and a plurality of cylindrical sections of varying diameter configured to direct the flow of matter within the cylindrical cavity.

10. The separator of claim 1, further configured to allow passage of the flow of matter, unseparated, from the input port to the suction port when the flow of matter is no longer able to be expelled out of the collection port.

11. A liquid-gas flow separator, comprising:
a cylindrical cavity comprising a cylindrical cavity wall, a first cylindrical cavity end, and a second cylindrical cavity end, the separator configured to operate with the first cylindrical cavity end being up;
a suction port coupled to a suction source, the suction port being in the first cylindrical cavity end;
a conical cavity, the conical cavity comprising a wide end and a narrow end, the wide end being mated to the second cylindrical cavity end;
a collection port at the narrow end of the conical cavity;
an input port to receive a flow of matter comprising a mixture of liquid and gas, the input port being in the cylindrical cavity wall, the flow of matter induced into the separator by the suction source, the input port configured to direct liquids in the flow the matter to cling to the cylindrical cavity wall;
a baffle disposed between the input port and the suction port, wherein the baffle comprises a plurality of openings to allow the gasses in the flow of matter to be pulled out of the separator via the suction port, the baffle being configured to prevent liquids in the flow of matter from being pulled directly from the input port to the suction port without traversing at least a first portion of a circumference of the cylindrical cavity wall, the baffle configured to allow gasses in the flow of matter to separate from the liquids in the flow of matter and be pulled out of the separator via the suction port; and
a cylindrical central member disposed within the cylindrical cavity, the central member disposed to form an annular cavity between the cylindrical central member and the cylindrical cavity wall, the liquids in the flow of matter pass through the annular cavity before dropping out the collection port.

12. The separator of claim 11, wherein the baffle comprises a solid portion that prevents liquids in the flow of matter from being pulled directly from the input port to the suction port, the solid portion corresponding to at least the first portion of the circumference.

13. The separator of claim 11, wherein the central member comprises a tapered section disposed in the conical cavity.

14. The separator of claim 11, wherein the central member comprises a plurality of cylindrical sections comprising different diameters.

15. The separator of claim 14, wherein a plurality of cylindrical sections include a first section that defines a first portion of the annular cavity and a second section that defines a second portion of the annular cavity.

16. The separator of claim 15, wherein the first portion is disposed between the baffle and the second portion, the second portion is disposed between the first portion and the conical cavity.

17. The separator of claim 16, wherein the central member further comprises a tapered section disposed in the conical cavity thereby forming a hollow cone shaped cavity, the hollow cone shaped cavity disposed between the second portion and the second port.

* * * * *

UNITED STATES PATENT AND TRADEMARK OFFICE
CERTIFICATE OF CORRECTION

| | |
|---|---|
| PATENT NO. | : 10,420,867 B2 |
| APPLICATION NO. | : 15/296894 |
| DATED | : September 24, 2019 |
| INVENTOR(S) | : Noah Mark Minskoff |

It is certified that error appears in the above-identified patent and that said Letters Patent is hereby corrected as shown below:

In the Claims

Column 63, Line 23, Claim 13, please replace "the" with "of" between "flow" and "matter"

Signed and Sealed this
First Day of August, 2023

*Katherine Kelly Vidal*

Katherine Kelly Vidal
*Director of the United States Patent and Trademark Office*